US008548600B2

(12) United States Patent
Deem et al.

(10) Patent No.: US 8,548,600 B2
(45) Date of Patent: Oct. 1, 2013

(54) APPARATUSES FOR RENAL NEUROMODULATION AND ASSOCIATED SYSTEMS AND METHODS

(75) Inventors: Mark Deem, Mountain View, CA (US); Hanson Gifford, III, Woodside, CA (US); Denise Demarais, Saratoga, CA (US); Douglas Sutton, Pacifica, CA (US); Erik Thai, Mountain View, CA (US); Mark Gelfand, New York, NY (US); Howard R. Levin, Teaneck, NJ (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 13/619,851

(22) Filed: Sep. 14, 2012

(65) Prior Publication Data

US 2013/0012866 A1 Jan. 10, 2013

Related U.S. Application Data

(60) Continuation of application No. 12/777,892, filed on May 11, 2010, which is a continuation of application No. 11/782,451, filed on Jul. 24, 2007, now abandoned, which is a division of application No. 11/129,765, filed on May 13, 2005, now Pat. No. 7,653,438, and a continuation-in-part of application No. 10/408,665, filed on Apr. 8, 2003, now Pat. No. 7,162,303.

(60) Provisional application No. 60/616,254, filed on Oct. 5, 2004, provisional application No. 60/624,793, filed on Nov. 2, 2004, provisional application No. 60/370,190, filed on Apr. 8, 2002, provisional application No. 60/415,575, filed on Oct. 3, 2002, provisional application No. 60/442,970, filed on Jan. 29, 2003.

(51) Int. Cl.
*A61F 2/00* (2006.01)
*A61N 1/00* (2006.01)
*A61N 1/30* (2006.01)
*A61M 31/00* (2006.01)
*A61B 18/18* (2006.01)

(52) U.S. Cl.
USPC .......... 607/101; 607/44; 604/21; 604/103.01; 606/41

(58) Field of Classification Search
USPC ................ 604/21, 103.01; 607/44, 101, 116; 606/41
See application file for complete search history.

(56) References Cited

U.S. PATENT DOCUMENTS 2,130,758 A 9/1938 Rose
2,276,995 A 3/1942 Milinowski
(Continued)

FOREIGN PATENT DOCUMENTS

DE 3151180 8/1982
DE 29909082 U1 7/1999
(Continued)

OTHER PUBLICATIONS

U.S. Appl. No. 95/002,110, filed Aug. 29, 2012, Demarais et al.
(Continued)

*Primary Examiner* — Mark W Bockelman

(57) ABSTRACT

Methods and apparatus are provided for renal neuromodulation using a pulsed electric field to effectuate electroporation or electrofusion. It is expected that renal neuromodulation (e.g., denervation) may, among other things, reduce expansion of an acute myocardial infarction, reduce or prevent the onset of morphological changes that are affiliated with congestive heart failure, and/or be efficacious in the treatment of end stage renal disease. Embodiments of the present invention are configured for percutaneous intravascular delivery of pulsed electric fields to achieve such neuromodulation.

28 Claims, 12 Drawing Sheets

(56) References Cited

U.S. PATENT DOCUMENTS

| | | |
|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault |
| 4,674,482 A | 6/1987 | Waltonen et al. |
| 4,692,147 A | 9/1987 | Duggan |
| 4,715,852 A | 12/1987 | Reinicke et al. |
| 4,774,967 A | 10/1988 | Zanakis |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,300,068 A | 4/1994 | Rosar et al. |
| 5,304,120 A | 4/1994 | Crandell et al. |
| 5,304,206 A | 4/1994 | Baker |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,345,936 A | 9/1994 | Pomeranz et al. |
| 5,351,394 A | 10/1994 | Weinberg |
| 5,358,514 A | 10/1994 | Schulman et al. |
| 5,368,591 A | 11/1994 | Lennox et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,423,744 A | 6/1995 | Gencheff et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,791 A | 4/1996 | Sit'ko |
| 5,531,778 A | 7/1996 | Maschino et al. |
| 5,540,730 A | 7/1996 | Terry, Jr. et al. |
| 5,540,734 A | 7/1996 | Zabara |
| 5,553,611 A | 9/1996 | Budd et al. |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,584,863 A | 12/1996 | Rauch et al. |
| 5,589,192 A | 12/1996 | Okabe et al. |
| 5,599,345 A | 2/1997 | Edwards et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,672,174 A | 9/1997 | Gough et al. |
| 5,688,266 A | 11/1997 | Edwards et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,722,401 A | 3/1998 | Pietroski et al. |

| Patent | Kind | Date | Inventor |
|---|---|---|---|
| 5,723,001 | A | 3/1998 | Pilla et al. |
| 5,725,563 | A | 3/1998 | Klotz et al. |
| 5,728,396 | A | 3/1998 | Peery et al. |
| 5,747,060 | A | 5/1998 | Sackler et al. |
| 5,755,750 | A | 5/1998 | Petruska et al. |
| 5,756,115 | A | 5/1998 | Moo-Young et al. |
| 5,772,590 | A | 6/1998 | Webster, Jr. |
| 5,792,187 | A | 8/1998 | Adams |
| 5,800,464 | A | 9/1998 | Kieval |
| 5,807,306 | A | 9/1998 | Shapland et al. |
| 5,810,802 | A | 9/1998 | Panescu et al. |
| 5,814,079 | A | 9/1998 | Kieval |
| 5,824,087 | A | 10/1998 | Aspden et al. |
| 5,836,935 | A | 11/1998 | Ashton et al. |
| RE35,987 | E | 12/1998 | Harris et al. |
| 5,843,069 | A | 12/1998 | Butler et al. |
| 5,861,021 | A | 1/1999 | Thorne et al. |
| 5,865,787 | A | 2/1999 | Shapland et al. |
| 5,871,449 | A | 2/1999 | Brown |
| 5,891,181 | A | 4/1999 | Zhu |
| 5,893,885 | A | 4/1999 | Webster et al. |
| 5,906,636 | A | 5/1999 | Casscells, III et al. |
| 5,906,817 | A | 5/1999 | Moullier et al. |
| 5,913,876 | A | 6/1999 | Taylor et al. |
| 5,916,154 | A | 6/1999 | Hobbs et al. |
| 5,916,239 | A | 6/1999 | Geddes et al. |
| 5,919,187 | A | 7/1999 | Guglielmi et al. |
| 5,924,997 | A | 7/1999 | Campbell |
| 5,928,272 | A | 7/1999 | Adkins et al. |
| 5,935,075 | A | 8/1999 | Casscells et al. |
| 5,944,710 | A | 8/1999 | Dev et al. |
| 5,954,719 | A | 9/1999 | Chen et al. |
| 5,983,131 | A | 11/1999 | Weaver et al. |
| 5,983,141 | A | 11/1999 | Sluijter et al. |
| 6,006,134 | A | 12/1999 | Hill et al. |
| 6,009,877 | A | 1/2000 | Edwards |
| 6,010,613 | A | 1/2000 | Walters et al. |
| 6,026,326 | A | 2/2000 | Bardy |
| 6,041,252 | A | 3/2000 | Walker et al. |
| 6,051,017 | A | 4/2000 | Loeb et al. |
| 6,058,328 | A | 5/2000 | Levine et al. |
| 6,058,331 | A | 5/2000 | King |
| 6,066,134 | A | 5/2000 | Eggers et al. |
| 6,073,048 | A | 6/2000 | Kieval et al. |
| 6,077,227 | A | 6/2000 | Miesel et al. |
| 6,086,527 | A | 7/2000 | Talpade |
| 6,117,101 | A | 9/2000 | Diederich et al. |
| 6,122,548 | A | 9/2000 | Starkebaum et al. |
| 6,123,718 | A | 9/2000 | Tu et al. |
| 6,135,999 | A | 10/2000 | Fanton et al. |
| 6,146,380 | A | 11/2000 | Racz et al. |
| 6,161,048 | A | 12/2000 | Sluijter et al. |
| 6,171,306 | B1 | 1/2001 | Swanson |
| 6,178,349 | B1 | 1/2001 | Kieval |
| 6,190,353 | B1 | 2/2001 | Makower et al. |
| 6,192,889 | B1 | 2/2001 | Morrish |
| 6,205,361 | B1 | 3/2001 | Kuzma et al. |
| 6,208,894 | B1 | 3/2001 | Schulman et al. |
| 6,214,032 | B1 | 4/2001 | Loeb et al. |
| 6,219,577 | B1 | 4/2001 | Brown, III et al. |
| 6,224,592 | B1 | 5/2001 | Eggers et al. |
| 6,238,702 | B1 | 5/2001 | Berde et al. |
| 6,245,026 | B1 | 6/2001 | Campbell et al. |
| 6,246,912 | B1 | 6/2001 | Sluijter et al. |
| 6,251,130 | B1 | 6/2001 | Dobak, III et al. |
| 6,254,598 | B1 | 7/2001 | Edwards et al. |
| 6,258,087 | B1 | 7/2001 | Edwards et al. |
| 6,259,952 | B1 | 7/2001 | Sluijter et al. |
| 6,269,269 | B1 | 7/2001 | Ottenhoff et al. |
| 6,272,377 | B1 | 8/2001 | Sweeney et al. |
| 6,272,383 | B1 | 8/2001 | Grey et al. |
| 6,273,886 | B1 | 8/2001 | Edwards |
| 6,280,377 | B1 | 8/2001 | Talpade |
| 6,287,304 | B1 | 9/2001 | Eggers et al. |
| 6,287,608 | B1 | 9/2001 | Levin et al. |
| 6,292,695 | B1 | 9/2001 | Webster, Jr. et al. |
| 6,304,777 | B1 | 10/2001 | Ben-Haim et al. |
| 6,304,787 | B1 | 10/2001 | Kuzma et al. |
| 6,306,423 | B1 | 10/2001 | Donovan et al. |
| 6,314,325 | B1 | 11/2001 | Fitz |
| 6,322,558 | B1 | 11/2001 | Taylor et al. |
| 6,322,559 | B1 | 11/2001 | Daulton et al. |
| 6,326,020 | B1 | 12/2001 | Kohane et al. |
| 6,326,177 | B1 | 12/2001 | Schoenbach et al. |
| 6,328,699 | B1 | 12/2001 | Eigler et al. |
| 6,334,069 | B1 | 12/2001 | George et al. |
| 6,347,247 | B1 | 2/2002 | Dev et al. |
| 6,353,763 | B1 | 3/2002 | George et al. |
| 6,356,786 | B1 | 3/2002 | Rezai et al. |
| 6,356,787 | B1 | 3/2002 | Rezai et al. |
| 6,366,808 | B1 | 4/2002 | Schroeppel et al. |
| 6,366,815 | B1 | 4/2002 | Haugland et al. |
| 6,393,324 | B2 | 5/2002 | Gruzdowich et al. |
| 6,400,982 | B2 | 6/2002 | Sweeney et al. |
| 6,405,079 | B1 | 6/2002 | Ansarinia |
| 6,405,732 | B1 | 6/2002 | Edwards et al. |
| 6,413,255 | B1 | 7/2002 | Stern |
| 6,415,183 | B1 | 7/2002 | Scheiner et al. |
| 6,415,187 | B1 | 7/2002 | Kuzma et al. |
| 6,438,423 | B1 | 8/2002 | Rezai et al. |
| 6,442,424 | B1 | 8/2002 | Ben-Haim et al. |
| 6,449,507 | B1 | 9/2002 | Hill et al. |
| 6,450,942 | B1 | 9/2002 | Lapanashvili et al. |
| 6,461,314 | B1 | 10/2002 | Pant et al. |
| 6,464,687 | B1 | 10/2002 | Ishikawa et al. |
| 6,473,644 | B1 | 10/2002 | Terry, Jr. et al. |
| 6,482,619 | B1 | 11/2002 | Rubinsky et al. |
| 6,488,679 | B1 | 12/2002 | Swanson et al. |
| 6,500,174 | B1 | 12/2002 | Maguire et al. |
| 6,506,189 | B1 | 1/2003 | Rittman et al. |
| 6,508,774 | B1 | 1/2003 | Acker et al. |
| 6,514,226 | B1 | 2/2003 | Levin et al. |
| 6,516,211 | B1 | 2/2003 | Acker et al. |
| 6,517,811 | B2 | 2/2003 | John et al. |
| 6,522,926 | B1 | 2/2003 | Kieval et al. |
| 6,522,932 | B1 | 2/2003 | Kuzma et al. |
| 6,524,607 | B1 | 2/2003 | Goldenheim et al. |
| 6,534,081 | B1 | 3/2003 | Goldenheim et al. |
| 6,536,949 | B1 | 3/2003 | Heuser |
| 6,564,096 | B2 | 5/2003 | Mest |
| 6,571,127 | B1 | 5/2003 | Ben-Haim et al. |
| 6,592,567 | B1 | 7/2003 | Levin et al. |
| 6,599,256 | B1 | 7/2003 | Acker et al. |
| 6,600,954 | B2 | 7/2003 | Cohen et al. |
| 6,600,956 | B2 | 7/2003 | Maschino et al. |
| 6,601,459 | B1 | 8/2003 | Jenni |
| 6,605,084 | B1 | 8/2003 | Acker et al. |
| 6,613,045 | B1 | 9/2003 | Laufer et al. |
| 6,615,071 | B1 | 9/2003 | Casscells, III et al. |
| 6,616,624 | B1 | 9/2003 | Kieval |
| 6,620,151 | B2 | 9/2003 | Blischak et al. |
| 6,622,041 | B2 | 9/2003 | Terry, Jr. et al. |
| 6,622,731 | B2 | 9/2003 | Daniel et al. |
| 6,635,054 | B2 | 10/2003 | Fjield et al. |
| 6,654,636 | B1 | 11/2003 | Dev et al. |
| 6,666,845 | B2 | 12/2003 | Hooper et al. |
| 6,669,655 | B1 | 12/2003 | Acker et al. |
| 6,671,556 | B2 | 12/2003 | Osorio et al. |
| 6,672,312 | B2 | 1/2004 | Acker |
| 6,676,657 | B2 | 1/2004 | Wood |
| 6,681,136 | B2 | 1/2004 | Schuler et al. |
| 6,684,105 | B2 | 1/2004 | Cohen et al. |
| 6,690,971 | B2 | 2/2004 | Schauerte et al. |
| 6,692,490 | B1 | 2/2004 | Edwards |
| 6,692,738 | B2 | 2/2004 | MacLaughlin et al. |
| 6,697,670 | B2 | 2/2004 | Chornenky et al. |
| 6,718,208 | B2 | 4/2004 | Hill et al. |
| 6,735,471 | B2 | 5/2004 | Hill et al. |
| 6,738,663 | B2 | 5/2004 | Schroeppel et al. |
| 6,749,598 | B1 | 6/2004 | Keren et al. |
| 6,780,183 | B2 | 8/2004 | Jimenez, Jr. et al. |
| 6,786,904 | B2 | 9/2004 | Doscher et al. |
| 6,795,728 | B2 | 9/2004 | Chornenky et al. |
| 6,845,267 | B2 | 1/2005 | Harrison et al. |
| 6,850,801 | B2 | 2/2005 | Kieval et al. |
| 6,862,479 | B1 | 3/2005 | Whitehurst et al. |
| 6,865,416 | B2 | 3/2005 | Dev et al. |
| 6,869,431 | B2 | 3/2005 | Maguire et al. |

| Patent/Pub No. | Date | Name |
|---|---|---|
| 6,885,888 B2 | 4/2005 | Rezai |
| 6,916,656 B2 | 7/2005 | Walters et al. |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,958,060 B2 | 10/2005 | Mathiesen et al. |
| 6,969,388 B2 | 11/2005 | Goldman et al. |
| 6,972,013 B1 | 12/2005 | Zhang et al. |
| 6,978,174 B2 | 12/2005 | Gelfand |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,155,284 B1 | 12/2006 | Whitehurst et al. |
| 7,162,303 B2 | 1/2007 | Levin et al. |
| 7,191,015 B2 | 3/2007 | Lamson et al. |
| 7,373,204 B2 | 5/2008 | Gelfand et al. |
| 7,444,183 B2 | 10/2008 | Knudson et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,756,583 B2 | 7/2010 | Demarais et al. |
| 8,131,371 B2 | 3/2012 | Demarais et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,295,902 B2 | 10/2012 | Salahieh et al. |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0139379 A1 | 10/2002 | Edwards et al. |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry, Jr. et al. |
| 2003/0045909 A1 | 3/2003 | Gross et al. |
| 2003/0050681 A1 | 3/2003 | Pianca et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0233099 A1 | 12/2003 | Danaek et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2006/0004417 A1 | 1/2006 | Rossing et al. |
| 2006/0004430 A1 | 1/2006 | Rossing et al. |
| 2006/0025821 A1 | 2/2006 | Gelfand |
| 2006/0030814 A1 | 2/2006 | Valencia et al. |
| 2006/0036218 A1 | 2/2006 | Goodson et al. |
| 2006/0041277 A1 | 2/2006 | Deem |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0095029 A1 | 5/2006 | Young et al. |
| 2006/0100667 A1 | 5/2006 | Machado et al. |

| | | |
|---|---|---|
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0288070 A1 | 12/2007 | Libbus et al. |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0091255 A1 | 4/2008 | Caparso et al. |
| 2008/0140150 A1 | 6/2008 | Zhou et al. |
| 2008/0213331 A1 | 9/2008 | Gelfand |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2010/0010567 A1 | 1/2010 | Deem et al. |
| 2010/0057150 A1 | 3/2010 | Demarais et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2011/0060324 A1 | 3/2011 | Wu et al. |
| 2011/0112400 A1 | 5/2011 | Emery et al. |
| 2011/0137298 A1 | 6/2011 | Nguyen et al. |
| 2011/0178570 A1 | 7/2011 | Demarais et al. |
| 2011/0200171 A1 | 8/2011 | Beetel et al. |
| 2011/0202098 A1 | 8/2011 | Demarais et al. |
| 2011/0257564 A1 | 10/2011 | Demarais et al. |
| 2011/0257622 A1 | 10/2011 | Salahieh et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2012/0029500 A1 | 2/2012 | Jenson |
| 2012/0029511 A1 | 2/2012 | Smith et al. |
| 2012/0029512 A1 | 2/2012 | Willard et al. |
| 2012/0071870 A1 | 3/2012 | Salahieh et al. |
| 2012/0157992 A1 | 6/2012 | Smith et al. |
| 2012/0157993 A1 | 6/2012 | Jenson et al. |
| 2012/0184952 A1 | 7/2012 | Jenson et al. |
| 2013/0012867 A1 | 1/2013 | Demarais et al. |

FOREIGN PATENT DOCUMENTS

| | | |
|---|---|---|
| DE | 10252325 A1 | 5/2004 |
| DE | 10257146 A1 | 6/2004 |
| EP | 0811395 | 6/1997 |
| EP | 1009303 B1 | 6/2009 |
| EP | 2092957 | 8/2009 |
| WO | WO/85/01213 | 3/1985 |
| WO | WO/91/04725 | 4/1991 |
| WO | WO/92/20291 | 11/1992 |
| WO | WO/93/02740 | 2/1993 |
| WO | WO/93/07803 | 4/1993 |
| WO | WO/94/00188 | 1/1994 |
| WO | WO/94/11057 | 5/1994 |
| WO | WO/95/25472 | 9/1995 |
| WO | WO-9525472 A1 | 9/1995 |
| WO | WO/95/33514 | 12/1995 |
| WO | WO/96/00039 | 1/1996 |
| WO | WO/96/04957 | 2/1996 |
| WO | WO/96/11723 | 4/1996 |
| WO | WO/97/13463 | 4/1997 |
| WO | WO/97/13550 | 4/1997 |
| WO | WO-9736548 A1 | 10/1997 |
| WO | WO/97/49453 | 12/1997 |
| WO | WO/98/37926 | 9/1998 |
| WO | WO/98/42403 | 10/1998 |
| WO | WO/98/43700 | 10/1998 |
| WO | WO/98/43701 | 10/1998 |
| WO | WO/98/48888 | 11/1998 |
| WO | WO/99/33407 | 7/1999 |
| WO | WO/99/51286 | 10/1999 |
| WO | WO/99/52424 | 10/1999 |
| WO | WO-9962413 A1 | 12/1999 |
| WO | WO-0122897 A1 | 4/2001 |
| WO | WO0126729 | 4/2001 |
| WO | WO0170114 | 9/2001 |
| WO | WO-0170114 A1 | 9/2001 |
| WO | WO/02/09808 | 2/2002 |
| WO | WO/02/26314 | 4/2002 |
| WO | WO/02/053207 | 7/2002 |
| WO | WO/02/070039 | 9/2002 |
| WO | WO/02/070047 | 9/2002 |
| WO | WO/02/085448 | 10/2002 |
| WO | WO/02085192 | 10/2002 |
| WO | WO/03/018108 | 3/2003 |
| WO | WO/03/028802 | 4/2003 |
| WO | WO/03/063692 | 8/2003 |
| WO | WO/03/071140 | 8/2003 |
| WO | WO/03/076008 | 9/2003 |
| WO | WO/03/082080 | 10/2003 |
| WO | WO/03/082403 | 10/2003 |
| WO | WO/2004/026370 | 4/2004 |
| WO | WO/2004/026371 | 4/2004 |
| WO | WO/2004/026374 | 4/2004 |
| WO | WO/2004/030718 | 4/2004 |
| WO | WO/2004/032791 | 4/2004 |
| WO | WO/2004/107965 | 12/2004 |
| WO | WO/2005/014100 | 2/2005 |
| WO | WO/2005/016165 | 2/2005 |
| WO | WO/2005/032646 | 4/2005 |
| WO | WO-2005/041748 A2 | 5/2005 |
| WO | WO/2005/065284 | 7/2005 |
| WO | WO/2005/084389 | 9/2005 |
| WO | WO/2005/097256 | 10/2005 |
| WO | WO/2005/110528 | 11/2005 |
| WO | WO-2005110528 A1 | 11/2005 |
| WO | WO/2005/123183 | 12/2005 |
| WO | WO/2006/007048 | 1/2006 |
| WO | WO/2006/018528 | 2/2006 |
| WO | WO/2006/022790 | 3/2006 |
| WO | WO/2006/031899 | 3/2006 |
| WO | WO/2006/041847 | 4/2006 |
| WO | WO/2006/041881 | 4/2006 |
| WO | WO-2006041881 A2 | 4/2006 |
| WO | WO-2007008954 A2 | 1/2007 |
| WO | WO/2007/035537 | 3/2007 |

| | | |
|---|---|---|
| WO | WO/2007/078997 | 7/2007 |
| WO | WO/2007/086965 | 8/2007 |
| WO | WO/2007/103879 | 9/2007 |
| WO | WO/2007/103881 | 9/2007 |
| WO | WO/2007/121309 | 10/2007 |
| WO | WO/2007/146834 | 12/2007 |
| WO | WO/2008/003058 | 1/2008 |
| WO | WO/2008/061150 | 5/2008 |
| WO | WO/2008/061152 | 5/2008 |
| WO | WO/2008/070413 | 6/2008 |
| WO | WO/2010/078175 | 7/2010 |
| WO | WO-2011082279 A2 | 7/2011 |
| WO | WO-2011119857 A2 | 9/2011 |
| WO | WO-2011130534 A2 | 10/2011 |
| WO | WO-2012016135 A1 | 2/2012 |
| WO | WO-2012075156 A1 | 6/2012 |

OTHER PUBLICATIONS

U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Benito, F., et al., "Radiofrequency catheter ablation of accessory pathways in infants." Heart, 78:160-162 (1997).
Curtis, John J. et al., "Surgical Therapy for Persistent Hypertension After Renal Transplantation" Transplantation, 31:125-128 (1981).
Dubac, M., et al., "Feasibility of cardiac cryoablation using a transvenous steerable electrode catheter." J Interv Cardiac Electrophysiol, 2:285-292 (1998).
Han, Y-M., et al., "Renal artery embolization with diluted hot contrast medium: An experimental study." J Vasc Interv Radiol. 12:862-868 (2001).
Kompanowska, E. et al., "Early effects of renal denervation in the anaesthetised rat: Natriuresis and increased cortical blood flow." J Physiol, 531.2:527-534 (2001).
Lee, S.-J., et al., "Ultrasonic energy in endoscopic surgery." Yonsei Med J 40:545-549 (1999).
Lustgarten, D.L., et al., "Cryothermal ablation: Mechanism of tissue injury and current experience in the treatment of tachyarrhythmias." Progr Cardiovasc Dis, 41:481-498 (1999).
Oliverira, V., et al., "Renal denervation normalizes pressure and baroreceptor reflex in high renin hypertension in conscious rats." Hypertension, 19:II-17-II21 (1992).
Peet, M., "Hypertension and its Surgical treatment by bilateral supradiaphyragmatic Splanchnicectomy," Am J. Surgery (1949) pp. 48-68.
Stella, A., et al., "Effects of reversible renal denervation on haemodynamic and excretory functions of the ipsilateral and contralateral kidney in the cat." J Hypertension, 4:181-188 (1986).
Swartz, J.F. et al., "Radiofrequency endocardial catheter ablation of accessory atrioventricular pathway artrial insertion sites." Circulation, 87:487-799 (1993).
Uchida, F., et al. "Effect of radiofrequency catheter ablation on parasympathetic denervation: A comparison of three different ablation sites." PACE, 21:2517-2521 (1998).
Weinstock, M., et al., "Renal denervation prevents sodium retention and hypertension in salt-sensitive rabbits with genetic baroreflect impairment." Clinical Science, 90: 287-293 (1996).
Avitall et al., "The Creation of Linear Contiguous Lesions in the Atria with an Expandable Loop Catheter"; Journal of the American College of Cardiology, 1999; vol. 33, No. 4; pp. 972-984, located online at: http://content/onlinejacc.org/cgi/content/full/33/4/972.
Excerpt of Operator's Manual, 110V; Boston Scientific's EPT-1000 XP Cardiac Ablation Controller & Accessories, Version of Apr. 2003, (6 pages).
Excerpt of Operator's Manual, 150; Boston Scientific, "Maestro 3000 Cardiac Ablation System", Version of Oct. 17, 2005, Ref. Catalog No. 21020, (4 pages).

Opposition to European Patent No. EP2092957, Granted Jan. 5, 2011, Date of Opposition Oct. 5, 2011 (26 pages).
Opposition to European Patent No. EP2037840, Granted Dec. 7, 2011, Date of Opposition Sep. 7, 2012 (25 pages).
Opposition to European Patent No. EP1802370, Granted Jan. 5, 2011, Date of Opposition Oct. 5, 2011 (20 pages).
Wittkampf et al., "Control of Radiofrequency Lesion Size by Power Regulation"; Circulation: Journal of the American Heart Association; 1989, vol. 80: pp. 962-968, located online at: http://circ.ahajournals.org/content/80/4/962.
Zheng et al., "Comparison of the temperature profile and pathological effect at unipolar, bipolar and phased radiofrequency current configurations," Journal of Interventional Cardian Electrophysiology, 2001, pp. 401-410.
European Search Report dated May 3, 2012; European Patent Application No. 11192511.1; Applicant: Ardian, Inc. (6 pages).
U.S. Appl. No. 60/813,589, filed Dec. 29, 2005, Demarais et al.
2003 European Society of Hypertension—European Society of Cardiology guidelines for the management of arterial hypertension, Guidelines Committee, Journal of Hypertension 2003, vol. 21, No. 6, pp. 1011-1053.
Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.
Abramov, G.S. et al., Alteration in sensory nerve function following electrical shock, Burns vol. 22, No. 8, 1996 Elsevier Science Ltd., pp. 602-606.
Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.
Advanced Neuromodulation Systems' Comparison Chart, 1 page, Dec. 16, 2008.
Advances in the role of the sympathetic nervous system in cardiovascular medicine, 2001 SNS Report, No. 3, Springer, Published with an educational grant from Servier, pp. 1-8.
Aggarwal, A. et al., Regional sympathetic effects of low-dose clonidine in heart failure. Hypertension. 2003;41:553-7.
Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.
Ahadian, Farshad M., M.D., Pulsed Radiofrequency Neurotomy: Advances in Pain Medicine, Current Pain and Headache Reports 2004, vol. 8, 2004 Current Science Inc., pp. 34-40.
Alexander, B.T. et al., Renal denervation abolishes hypertension in low-birth-weight offspring from pregnant rats with reduced uterine perfusion, Hypertension, 2005; 45 (part 2): 754-758.
Alford, J. Winslow, M.D. and Paul D. Fadale, M.D., Evaluation of Postoperative Bupivacaine Infusion for Pain Management After Anterior Cruciate Ligament Reconstruction, The Journal of Arthroscopic and Related Surgery, vol. 19, No. 8, Oct. 2003 Arthroscopy Association of North America, pp. 855-861.
Allen, E.V., Sympathectomy for essential hypertension, Circulation, 1952, 6:131-140.
Amersham Health. Hypaque-Cysto 6 pgs. 2003.
Andrews, B.T. et al., The use of surgical sympathectomy in the treatment of chronic renal pain. Br J Urol. 1997;80:6-10.
Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.
Archer, Steffen et al., Cell Reactions to Dielectrophoretic Manipulation, Mar. 1, 1999, Biochemical and Biophysical Research Communications, 1999 Academic Press, pp. 687-698.
Arentz, T. et al., Incidence of pulmonary vein stenosis 2 years after radiofrequency catheter ablation of refractory atrial fibrillation. European Heart Journal. 2003. 24; pp. 963-969.
Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.

Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.

Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.

Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.

Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.

Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.

Badyal, D. K., H. Lata and A.P. Dadhich, Animal Models of Hypertension and Effect of Drugs, Aug. 19, 2003, Indian Journal of Pharmacology 2003, vol. 35, pp. 349-362.

Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.

Balazs, Tibor, Development of Tissue Resistance to Toxic Effects of Chemicals, Jan. 26, 1974, Toxicology, 2 (1974), Elsevier/North-Holland, Amsterdam, pp. 247-255.

Barajas, L. Innervation of the renal cortex. Fex Proc. 1978;37:1192-201.

Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.

Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.

Bassett, C. Andrew L. et al., Augmentation of Bone Repair by Inductively Coupled Electromagnetic Fields, May 3, 1974, Science, vol. 184, pp. 575-577.

Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.

Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.

Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.

Bello-Reuss, E. et al., Acute unilateral renal denervation in rats with extracellular volume expansion, Departments of Medicine and Physiology, University of North Carolina School of Medicine. F26-F32 Jul. 1975.

Bello-Reuss, E. et al., Effect of renal sympathetic nerve stimulation on proximal water and sodium reabsorption, J Clin Invest, 1976;57:1104-1107.

Bello-Reuss, E. et al., Effects of Acute Unilateral Renal Denervation in the Rat, J Clin Invest, 1975;56:208-217.

Berde, C. et al., Local Anesthetics, Anesthesia, Chapter 13, 5th addition, Churchill-Livingston, Philadelphia 2000, pp. 491-521.

Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.

Bhandari, A. and Ellias, M., Loin pain hematuria syndrome: Pain control with RFA to the Splanchanic plexus, The Pain Clinic, 2000, vol. 12, No. 4, pp. 323-327.

Bhatt, Deepak L. et al., Rhabdomyolysis Due to Pulsed Electric Fields, May 11, 1989, Plastic and Reconstructive Surgery Jul. 1990, pp. 1-11.

Bichet, D., et al., Renal intracortical blood flow and renin secretion after denervation by 6-hydrmdopamine. Can J Physiol Pharmacol. 1982;60:184-92.

Bigler, D. et al., Tachyphylaxis during postoperative epidural analgesia—new insights, Apr. 15, 1987, Letter to the Editor, Acta Anaesthesiol Scand. 1987, vol. 31, pp. 664-665.

Binder, Allan et al., Pulsed Electromagnetic Field Therapy of Persistent Rotator Cuff Tendinitis, The Lancet, Saturday Mar. 31, 1984, The Lancet Ltd., pp. 695-698.

Black, M.D., Henry R., Resistant Hypertension 2004, presentation at Rush University Medical Center, Jul. 15, 2004, 40 pages.

Blad, B., et al., An Electrical Impedance index to Assess Electroporation in Tissue, Tissue and Organ (Therapy), 2001, Oslo, pp. 31-34, www.bl.uk <http://www.bl.uk> British Library, 2001, Oslo.

Blair, M. L. et al, Sympathetic activation cannot fully account for increased plasma renin levels during water deprivation, Sep. 23, 1996, Am. J. Physiol., vol. 272, 1997, the American Physiological Society 1997, pp. R1197-R1203.

Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.

Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005. 31 slides.

Bourge, R.C., Heart Failure Monitoring Devices: Rationale and Status 28 pages, Feb. 2001.

Braunwald, E., Heart Disease, A Textbook of Cardiovascular Medicine, 5th Ed., vol. 2, 1997, pp. 480-481, 824-825, 1184-1288 and 1923-1925, W.B. Saunders Company.

Bravo, E.L., et al., Renal denervation for resistant hypertension, American Journal of Kidney Diseases, 2009, 3 pgs.

Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. Pages 1318-1325. Dec. 2005.

Burkhoff, D., Interventional Device-Based Therapy for CHF Will Redefine Current Treatment Paradigms. Columbia University. 2004. 32 slides.

Burns, J. et al., Relationship between central sympathetic drive and magnetic resonance imaging-determined left ventricular mass in essential hypertension. Circulation. 2007;115:1999-2005.

Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.

Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.

Calaresu, F.R. et al., Haemodynamic Responses and Renin Release During Stimulation of Afferent Renal Nerves in the Cat, Aug. 12, 1975, J. Physiol. 1976, vol. 255, pp. 687-700.

Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.

Campese, V.M. et al., Renal afferent denervation prevents hypertension in rats with chronic renal failure. Hypertension. 1995;25:878-82.

Campese, V.M. et al., Renal Afferent Denervation Prevents the Progression of Renal Disease in the Renal Ablation Model of Chronic Renal Failure in the Rat, Am J Kidney Dis. 1995;26:861-5.

Campese, V.M., A new model of neurogenic hypertension caused by renal injury: pathophysiology and therapeutic implications, Clin Exp Nephrol (2003) 7: 167-171, Japanese Society of Nephrology 2003.

Campese, V.M., Neurogenic factors and hypertension in chronic renal failure, Journal of Nephrology, vol. 10, No. 4, 1997, Societa Italiana di Nefrologia, pp. 184-187.

Campese, V.M., Neurogenic factors and hypertension in renal disease. Kidney Int. 2000;57 Suppl 75:S2-3.

Canbaz, S. et al., Electrophysiological evaluation of phrenic nerve injury during cardiac surgery—a prospective, controlled clinical study. BioMed Central. 5 pgs. 2004.

Cardiac Glycosides, Heart Disease—A Textbook of Cardiovascular Medicine vol. 2, Edited by Eugene Braunwald, 5th Edition, WB Saunders Company, pp. 480-481, 1997.

Carls, G. et al., Electrical and magnetic stimulation of the intercostal nerves: a comparative study, Electromyogr, clin. Neurophysiol. 1997, vol. 37, pp. 509-512.

Carlson, Scott H. And J. Michael Wyss, e-Hypertension—Opening New Vistas, Introductory Commentary, Hypertension 2000, vol. 35, American Heart Association, Inc. 2000, p. 538.

Carson, P., Device-based Treatment for Chronic Heart Failure: Electrical Modulation of Myocardial Contractility. Transcatheter Cardiovascular Therapeutics 2005. 21 slides.

Chang, Donald C., Cell poration and cell fusion using an oscillating electric field, Biophysical Journal, vol. 56, Oct. 1989, Biophysical Society, pp. 641-652.

Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.

Chin, J.L. et al., Renal autotransplantation for the loin pain-hematuria syndrome: long term follow up of 26 cases, J Urol, 1998, vol. 160, pp. 1232-1236.

Chiou, C.W. et al., Efferent Vagal Innervation of the Canine Atria and Sinus and Atrioventricular Nodes. Circulation. Jun. 1997. 95(11):2573-2584. Abstract only. 2 pgs.

Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.

*Clinical Trials in Hypertension and Renal Diseases*, Slide Source www.hypertensiononline.org, 33 pages Aug. 13, 2001.

Conradi, E. and Ines Helen Pages, Effects of Continous and Pulsed Microwave Irradiation on Distribution of Heat in the Gluteal Region of Minipigs, Scand J Rehab Med, vol. 21, 1989, pp. 59-62.

Converse, R.L., Jr. et al., Sympathetic Overactivity in Patients with Chronic Renal Failure, N Engl J Med. Dec. 31, 1992, vol. 327 (27), pp. 1912-1918.

Cosman, E.R., Jr. et al., Electric and Thermal Field Effects in Tissue Around Radiofrequency Electrodes, Pain Medicine, vol. 6, No. 6, 2005, American Academy of Pain Medicine, pp. 405-424.

Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.

Crawford, William H. et al., Pulsed Radio Frequency Therapy of Experimentally Induced Arthritis in Ponies, Dec. 18, 1989, Can. J. Vet. Res. 1991, vol. 55, pp. 76-85.

Curtis, J.J. et al., Surgical theray for persistent hypertension after renal transplantation, Transplantation, 1981, 31(2):125-128.

Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.

Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.

Dang, Nicholas C. et al., A Novel Approach to Increase Total Urine Output in Heart Failure: Renal Nerve Blockade, ACC 2005 poster; 1 page.

Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.

Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.

Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.

De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.

Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.

Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.

Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.

Dev, Nagendu B., Ph.D. et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.

Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.

Dibona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.

Dibona, Gerald F. and Susan Y. Jones, Dynamic Analysis of Renal Nerve Activity Responses to Baroreceptor Denervation in Hypertensive Rats, Sep. 19, 2000, Hypertension Apr. 2001, American Heart Association, Inc. 2001, pp. 1153-1163.

Dibona, Gerald F. and Ulla C. Kopp, Neural Control of Renal Function, Physiological Reviews, vol. 77, No. 1, Jan. 1997, the American Physiological Society 1997, pp. 75-197.

Dibona, Gerald F. and Ulla C. Kopp, Role of the Renal Sympathetic Nerves in Pathophysiological States, Neural Control of Renal Function, vol. 77, pp. 142-197 Jan. 1997.

Dibona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.

Dibona, Gerald F., L.L. Sawin, Effect of renal nerve stimulation on NaCl and H2O transport in Henle's loop of the rat,: 1982, American Physiological Society, F576-F580, 5 pgs.

Dibona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.

Dibona, Gerald F., Neural Control of the Kidney—Past, Present and Future, Nov. 4, 2002, Novartis Lecture, Hypertension 2003, 41 part 2, 2002 American Heart Association, Inc., pp. 621-624.

Dibona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.

Dibona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.

Dibona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.

Dibona, Gerald F., Sympathetic Nervous System and the Kidney in Hypertension, Current Opinion in Nephrology and Hypertension 2002, vol. 11, 2002 Lippincott Williams & Wilkins, pp. 197-200.

Dibona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.

Dibona, Gerald, LL Sawin, Effect of renal denervation on dynamic autoregulation of renal blood flow, Feb. 12, 2004, AmJ Physiol Renal Physiol 286, pp. F1209-F1218.

Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. Pages 845-852.

Dorros, Gerald, M.D., Renal Artery Stenting State of the Art, presentation, TCT, Washington D.C., Sep. 2003, 27 pages.

Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.

Dunn, Matthew D. et al., Laparoscopic Nephrectomy in Patients With End-Stage Renal Disease and Autosomal Dominant Polycystic Kidney Disease,Oct. 25, 1999, American Journal of Kidney Diseases, vol. 35, No. 4 (April) 2000, National Kidney Foundation, Inc. 2000, pp. 720-725.

Durand, D.M., Electric Field Effects in Hyperexcitable Neural Tissue: A Review, Radiation Protection Dosimetry, vol. 106, No. 4, 2003 Nuclear Technology Publishing, pp. 325-331.

Effects of Renal Failure on the Cardiovascular System, 5th Edition Heart Disease, A Textbook of Cardiovascular Medicine, vol. 2, Edited by Eugene Braunwald, W.B. Saunders Company, pp. 1923-1925 1997.

Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.

Electropermeabilization (Electroporation), Cyto Pulse Sciences, Inc., http://www.cytopulse.com/electroporation.html (last accessed Mar. 3, 2005), 3 pgs.

Electroporation based Technologies and Treatments, ESPE Newsletter No. 6, QLK 02002-2003, Jan. 2005, www.cliniporator.com, 4 pgs.

End-stage renal disease payment policies in traditional Medicare, Chapter 8, Report to the Congress: Medicare Payment Policy, Mar. 2001, Medpac, pp. 123-138.

Epidemiology of Renal Disease in Hypertension, slide presentation by hypertensiononline.org, 21 pages Mar. 30, 2001.

Erdine, Serap and Alev Arat-Ozkan, Resistant Hypertension, European Society of Hypertension Scientific Newsletter: Update on Hypertension Management 2003, vol. 4, No. 15, 2 pages.

Esler, M. et al., Mechanism of elevated plasma noradrenaline in the course of essential hypertension. J Cardiovasc Pharmacol. 1986;8:S39-43.

Esler, M. et al., Noradrenaline release and the pathophysiology of primary human hypertension. Am J Hypertens. 1989; 2:140S-146S.

Esler, M. et al., Sympathetic nerve biology in essential hypertension, Clin and Exp Pharmacology and Physiology, 2001, 28:986-989.

European Examination Report; European Patent Application No. 07799148.7; Applicant: Ardian, Inc.; Date of Mailing: Jan. 19, 2010, 4 pgs.

European Examination Report; European Patent Application No. 09156661.2; Applicant: Ardian, Inc.; Date of Mailing: Jan. 19, 2010, 6 pgs.

European Search Report; European Patent Application No. 05806045.0; Applicant: Ardian, Inc.; Date of Mailing: Sep. 22, 2009, 8 pgs.

European Search Report; European Patent Application No. 05811851.4; Applicant: Ardian, Inc.; Date of Mailing: Oct. 1, 2009, 7 pgs.

European Search Report; European Patent Application No. 06847926.0; Applicant: Ardian, Inc.; Date of Mailing: Feb. 10, 2010, 6 pgs.

European Search Report; European Patent Application No. 0775925.8; Applicant: Ardian, Inc.; Date of Mailing: Apr. 29, 2010, 9 pgs.

European Search Report; European Patent Application No. 07798341.9; Applicant: Ardian, Inc.; Date of Mailing Aug. 4, 2011; 6 pgs.

European Search Report; European Patent Application No. 07799148.7; Applicant: Ardian, Inc.; Date of Mailing: Jul. 23, 2009, 6 pgs.

European Search Report; European Patent Application No. 07868755.5; Applicant: Ardian, Inc.; Date of Mailing: Jul. 28, 2010, 7 pgs.

European Search Report; European Patent Application No. 09156661.2; Applicant: Ardian, Inc.; Date of Mailing: Jul. 23, 2009, 6 pgs.

European Search Report; European Patent Application No. 09167937.3; Applicant: Ardian, Inc.; Date of Mailing: Nov. 11, 2009, 6 pgs.

European Search Report; European Patent Application No. 09168202.1; Applicant: Ardian, Inc.; Date of Mailing: Nov. 11, 2009, 5 pgs.

European Search Report; European Patent Application No. 09168204.7; Applicant: Ardian, Inc.; Date of Mailing: Nov. 19, 2009, 6 pgs.

Evelyn, K.A. et al., Effect of thoracolumbar sympathectomy on the clinical course of primary (essential) hypertension, Am J Med, 1960;28:188-221.

Ex parte Quayle Office Action; U.S. Appl. No. 11/144,173; Mailed on May 28, 2009, 4 pgs.

Fact Book Fiscal Year 2003, National Institutes of Health National Heart, Lung, and Blood Institute, Feb. 2004, 197 pgs.

Fajardo, J. et al., Effect of chemical sympathectomy on renal hydroelectrolytic handling in dogs with chronic caval constriction. Clin Physiol Biochem. 1986;4:252-6.

Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.

Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.

Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.

Fields, Larry E. et al., The Burden of Adult Hypertension in the United States 1999 to 2000—A Rising Tide, May 18, 2004, American Heart Association 2004, Hypertension Oct. 2004, pp. 1-7.

Final Office Action; U.S. Appl. No. 11/233,814; Mailed on Jan. 29, 2009, 11 pgs.

Final Office Action; U.S. Appl. No. 11/266,993; Mailed on Jan. 8, 2010, 7 pgs.

Final Office Action; U.S. Appl. No. 11/363,867; Mailed on May 1, 2009, 8 pgs.

Final Office Action; U.S. Appl. No. 11/451,728; Mailed on Jan. 13, 2009, 7 pgs.

Final Office Action; U.S. Appl. No. 11/599,649; Mailed on Jan. 15, 2009, 10 pgs.

Final Office Action; U.S. Appl. No. 11/599,723; Mailed on Apr. 5, 2010, 17 pgs.

Final Office Action; U.S. Appl. No. 11/599,890; Mailed on Apr. 29, 2009, 9 pgs.

Fischell, Tim A. et al., Ultrasonic Energy: Effects on Vascular Function and Integrity, Circulation: Journal of the American Heart Association. 1991. 84;pp. 1783-1795.

Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.

Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.

Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.

Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.

Gattone II, Vincent H. et al., Contribution of Renal Innervation to Hypertension in Polycystic Kidney Disease in the Rat, University of Chicago Section of Urology, 16 pages, Mar. 17, 2008.

Gaylor, D.C. et al., Significance of Cell Size and Tissue Structure in Electrical Trauma, Jan. 26, 1988, J. theor. Biol. 1988, vol. 133, 1988 Academic Press Limited, pp. 223-237.

Gazdar, A.F. and G.J. Dammin, Neural degeneration and regeneration in human renal transplants, NEJM, Jul. 30, 1970, 283:222-244.

Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba <http:www.elsevier.com/locate/bba>.

Getts, R.T. et al., Regression of left ventricular hypertrophy after bilateral nephrectomy, Nephrol Dial Transplant, 2006, vol. 21, pp. 1089-1091.

Ghoname, El-sayed A. et al., Percutaneous electrical nerve stimulation: an alternative to TENS in the management of sciatica, Apr. 26, 1999, Pain 1999, vol. 83, 1999 International Association for the Study of Pain / Published by Elsevier Science B.V., pp. 193-199.

Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.

Goldberger, Jeffrey J. et al., New technique for vagal nerve stimulation, Jun. 2, 1999, Journal of Neuroscience Methods 91, 1999, Elsevier Science B.V. 1999, pp. 109-114.

Gorbunov, F.E. et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).

Gottschalk, C.W., Renal nerves and sodium excretion, Ann. Rev. Physiol., 1979, 41:229-240.

Greenwell, T.J. et al., The outcome of renal denervation for managing loin pain haematuria syndrome. BJU International, 2004; 4 pgs.

Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.

Guimaraes, Sarfim. Vascular Adrenoceptors: An Update. pp. 319-356, Jun. 1, 2001.

Haissaguerre, M. et al., Spontaneous initiation of atrial fibrillation by ectopic beats orginating in the pulmonary veins, New England Journal of Medicine, 1998, 339: 659-666.

Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.

Hammer, Leah W. Differential Inhibition of Functional Dilation of Small Arterioles by Indomethacin and Glibenclamide. Hypertension. Feb. 2001 Part II. pp. 599-603.

Hampers, C.L. et al., A hemodynamic evaluation of bilateral nephrectomy and hemodialysis in hypertensive man, Circulation. 1967;35:272-288.

Hamza, M.D., Mohamed A. et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.

Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.

Hansen, J.M. et al., The transplanted human kidney does not achieve functional reinnervation, Clin Science, 1994, vol. 87, pp. 13-20.

Hasking, G.J. et al., Norepinephrine spillover to plasma in patients with congestive heart failure: evidence of increased overall and cardiorenal sympathetic nervous activity. Circulation. 1986;73:615-21.

Hausberg, M. et al., Sympathetic nerve activity in end-stage renal disease, Circulation, 2002, 106: 1974-1979.

Heart Arrhythmia Heart and Vascular Health on Yahoo! Health. 13 pgs. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.

Heart Disease and Stroke Statistics—2004 Update, American Heart Association, American Stroke Association, Dallas, Texas, 2003 American Heart Association, 52 pgs.

Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.

Heuer, G.J., The surgical treatment of essential hypertension, Annals of Surgery, 1936; 104 (4): 771-786.

Higuchi, Yoshinori, M.D., Ph.D. et al, Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.

Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.

Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.

Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997. Abstract. 2 pgs.

Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.

Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.

Horwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.

Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.

Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.

Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.

Hypertension and Renal Disease: Mechanisms, Slide Show by www.hypertensiononline.org, 22 pages Mar. 30, 2001.

Hypertension Incidence and Prevalence, Age-Specific Rates, by Gender, B.C., 2001/2002, Graph, Chronic Disease Management, May 2003, British Columbia Ministry of Health Services, 1 page.

Implantable Pump—The Medtronic MiniMed 2007 Implantable Insulin Pump System, Medtronic MiniMed 2004, 2 pgs.

International Search Report and Written Opinion for PCT/US2009/069334; Applicant: Ardian, Inc.; Mailing Date: Mar. 1, 2010, 10 pgs.

International Search Report and Written Opinion, PCT/US05/35693, Mailed on Mar. 8, 2006, Applicant: Ardian, Inc., 29 pgs.

International Search Report and Written Opinion, PCT/US05/35757, Mailed on Dec. 27, 2006, Applicant: Ardian, Inc., 8 pgs.
International Search Report and Written Opinion, PCT/US06/36120, Mailed on Jun. 25, 2008, Applicant: Ardian, Inc., 10 pgs.
International Search Report and Written Opinion, PCT/US06/41889, Mailed on Oct. 20, 2008, Applicant: Ardian, Inc., 7 pgs.
International Search Report and Written Opinion, PCT/US06/48822, Mailed on Aug. 15, 2008, Applicant: Ardian, Inc., 12 pgs.
International Search Report and Written Opinion, PCT/US07/63322, Mailed on Mar. 3, 2008, Applicant: Ardian, Inc., 13 pgs.
International Search Report and Written Opinion, PCT/US07/63324, Mailed on Oct. 10, 2008, Applicant: Ardian, Inc., 13 pgs.
International Search Report and Written Opinion, PCT/US07/66539, Mailed on Jan. 28, 2008, Applicant: Ardian, Inc., 8 pgs.
International Search Report and Written Opinion, PCT/US07/70799, Mailed on Jul. 2, 2008, Applicant: Ardian, Inc., 7 pgs.
International Search Report and Written Opinion, PCT/US07/72396, Mailed on Aug. 27, 2008, Applicant: Ardian, Inc., 9 pgs.
International Search Report and Written Opinion, PCT/US07/84701, Mailed on Aug. 21, 2008, Applicant: Ardian, Inc., 11 pgs.
International Search Report and Written Opinion, PCT/US07/84705, Mailed on Jul. 28, 2008, Applicant: Ardian, Inc., 12 pgs.
International Search Report and Written Opinion, PCT/US07/84708, Mailed on Aug. 11, 2008, Applicant: Ardian, Inc., 9 pgs.
International Search Report, PCT/US02/0039, Mailed Sep. 11, 2002, Applicant: Advanced Neuromodulation Systems, Inc.
International Search Report, PCT/US02/25712, Mailed on Apr. 23, 2003, Applicant: Cyberonics, Inc.
International Search Report, PCT/US03/08014, Mailed on Sep. 23, 2003, Applicant: The General Hospital Corporation.
International Search Report, PCT/US03/09764, Mailed on Oct. 28, 2003, Applicant: CVRX, Inc.
International Search Report, PCT/US04/38498, Mailed Feb. 18, 2005, Applicant: G & L Consulting, LLC, 4 pgs.
Introduction to Autonomic Pharmacology, Chapter 3, Part 2 Autonomic Pharmacology, pp. 18-26, May 24, 2002.
Isovue: Data Sheet. Regional Health Limited. 8 pgs. Mar. 11, 2003.
Israili, Z.H., Clinical pharmacokinetics of angiotensin II (AT) receptor blockers in hypertension, Journal of Human Hypertension, 2000, Macmillan Publishers Ltd., vol. 14, pp. S73-S86.
Janda, J., Impact of the electrical stimulation apparatus rebox on the course of ischemic renal damage in rats, British Library—The world's knowledge pp. 252-254 (translated and untranslated versions) 1996.
Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.
Jia, Jianping et al., Cold injury to nerves is not due to ischaemia alone, Brain. 121;pp. 989-1001. 1998.
Jia, Jianping et al.., The pathogenesis of non-freezing cold nerve injury: Observations in the rat, Brain. 120; pp. 631-646. 1997.
Jin, Yuanzhe et al., Pulmonary Vein Stenosis and Remodeling After Electrical Isolation for Treatment of Atrial Fibrillation: Short- and Medium-Term Follow-Up, PACE, vol. 27. pp. 1362-1370. Oct. 2004.
Johansson, Bjorn, Electrical Membrane Breakdown, a Possible Mediator of the Actions of Electroconvulsive Therapy, Medical Hypotheses 1987, vol. 24, Longman Group UK Ltd 1987, pp. 313-324.
Joles, J.A. et al., Causes and Consequences of Increased Sympathetic Activity in Renal Disease. Hypertension. 2004;43:699-706.
Jorgensen, William A. et al., Electrochemical Therapy of Pelvic Pain: Effects of Pulsed Electromagnetic Fields (PEMF) on Tissue Trauma, Eur J Surg 1994, Suppl 574, vol. 160, 1994 Scandinavian University Press, pp. 83-86.
Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, pp. 052901-1-052901-4.
Joshi, R. P. et al., Improved energy model for membrane electroporation in biological cells subjected to electrical pulses, Apr. 9, 2002, Physical Review E, vol. 65, 041920-1, 2002 The American Physical Society, 8 pages.
Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.
Joye, James D.et al., In Vivo Study of Endovascular Cryotherapy for the Prevention of Restenosis, 4 pages, 2003.
Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II):II-166-II-174.
Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.
Katholi, Richard E., Renal nerves in the pathogenesis of hypertension in experimental animals and humans, Am. J. Physiol. vol. 245, 1983, the American Physiological Society 1983, pp. F1-F14.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+]in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by The American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha1- and alpha2-adrenoceptors on renal sensory nerve fibers. Am J Physiol Regul Integr Comp Physiol. 2007;293:R1561-72.
Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.

Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.

Kumagai, K. et al. New Approach to Pulmonary Vein Isolation for Atrial Fibrillation Using a Multielectrode Basket Catheter. Circulation Journal. 2006;70:88-93.

Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.

Lavie, Peretz, Ph.D. and Victor Hoffstein, M.D., Sleep Apnea Syndrome: A Possible Contributing Factor to Resistant Hypertension, Jun. 2001, SLEEP 2001, vol. 24, No. 6, pp. 721-725.

Le Noble, J.L. et al., Pharmacological evidence for rapid destruction of efferent renal nerves in rats by intrarenal infusion of 6-hydroxydopamine. J Hypertens Suppl. 1985;3:S137-40.

Lee, Michael A. (editor). SPORTSMed. Connecticut State Medical Society Committee on the Medical Aspects of Sports. Fall/Winter 2005. 10 pgs.

Lee, Raphael C. et al., Biophysical Injury Mechanisms in Electronic Shock Trauma, Annu. Rev. Biomed. Eng., 2000, vol. 2, Copyright © 2000 by Annual Reviews, pp. 477-509.

Lee, Raphael C. et al., Clinical Sequelae Manifested in Electrical Shock Survivors, Presentation by the Electrical Trauma Research Program, The University of Chicago, 37 pages Dec. 24, 2004.

Lee, Raphael C. et al., Membrane Biology and Biophysics, Chapter 25, Surgical Research, 2001 Academic Press, pp. 297-305.

Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.

Lenoble, L.M. et al., Selective efferent chemical sympathectomy of rat kidneys. Am J Physiol. 1985;249:R496-501.

Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.

Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.

Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.

Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.

Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.

Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.

Lohmeier, Thomas E. et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.

Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.

Lohmeier, Thomas E., Interactions Between Angiotensin II and Baroreflexes in Long-Term Regulation of Renal Sympathetic Nerve Activity, Circulation Research, Jun. 27, 2003, American Heart Association, Inc.2003, pp. 1282-1284.

Luff, S.E. et al., Two types of sympathetic axon innervating the juxtaglomerular arterioles of the rabbit and rat kidney differ structurally from those supplying other arteries, May 1, 1991, Journal of Neurocytology 1991, vol. 20, 1991 Chapman and Hall Ltd., pp. 781-795.

Luippold, G. et al., Chronic renal denervation prevents glomerular hyperfiltration in diabetic rats, Nephrol Dial Transplant (2004) 19:342-347.

Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.

Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.

Malpas, Simon C., What sets the long-term level of sympathetic nerve activity: is there a role for arterial baroreceptors?, Invited Review, Am J Physiol Regul Integr Comp Physiol 2004, vol. 286, 2004 the American Physiological Society, pp. R1-R12.

Mancia, G., Grassi, G., Giannattasio, C., Seravalle, G., Sympathetic actrivation of pathogenesis of hypertension and progression of organ damage, Hypertension 1999, 34 (4 Pt 2): 724-728.

Marenzi, Giancarlo, M.D. et al., The Prevention of Radiocontrast-Agent-Induced Nephropathy by Hemofiltration, New England Joumal of Medicine, Oct. 2, 2003, vol. 349 (14), 2003 Massachusetts Medical Society, pp. 1333-1340.

Market for infusion pumps grows with an aging population, NWL 97-01, The BBI Newsletter, vol. 20, No. 2, Feb. 1, 1997, American Health Consultants, Inc., 6 pages.

Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.

Mathur, Vandana S., Intra-Renal Drug Delivery for Fluid Overload, FlowMedica. Transcatheter Cardiovascular Therapeutics 2005. 31 slides.

McCreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.

McCullough, Peter A., M.D., MPH et al., Acute Renal Failure after Coronary Intervention: Incidence, Risk Factors and Relationship to Mortality, Apr. 14, 1997, Am J Med. 1997, vol. 103, 1997 Excerpta Medica, Inc., pp. 368-375.

McMurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.

McRobbie, D. and M.A. Foster, Thresholds for biological effects of time-varying magnetic fields, Dec. 16, 1983, Clin. Phys. Physiol. Meas. 1984, vol. 5, No. 2, 1984 The Institute of Physics, pp. 67-78.

Medtronic Inc., MiniMed 2007, Implantable Insulin Pump System (Shoreview, MN) 4 pgs.

Medtronic Neurostimulation Systems, Expanding the Array of Pain Control Solutions, informational pamphlet, 1999 Medtronic, Inc., 6 pages.

Medtronic, Spinal Cord Stimulation, Patient Management Guidelines for Clinicians, Medtronic, Inc. 1999, 115 pages.

Medtronic, SynchroMed Infusion System—Clinical Reference Guide for Pain Therapy, Medtronic, Inc. 1998, 198 pages.

Mehran, Roxana, Renal insufficiency and contrast nephropathy: The most common, least understood risk factor, Cardiovascular Research Foundation. Columbia University Medical Center. 2005. 86 slides.

Mess, Sarah A., M.D. et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.

Micro ETS Hyperhidrosis USA Hyperhidrosis USA. 2 pgs. <URL: http://www.hyperhidrosis-usa.com/Index.html>. Nov. 6, 2006.

Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.

Miklavčič, D. et al, A Validated Model of in Vivo Electric Field Distribution in Tissues for Electrochemotherapy and for DNA Electrotransfer for Gene Therapy, Biochimica et Biophysica Acta, 1523, 2000, pp. 73-83, <http:www.elsevier.com/locate/bba>.

Mitchell, G. A. G., The Nerve Supply of the Kidneys, Aug. 20, 1949, Acta Anatomica, vol. X, Fasc. ½, 1950, pp. 1-37.

Morrisey, D.M. et al., Sympathectomy in the treatment of hypertension: Review of 122 cases, Lancet. 1953;1:403-408.

Moss, Nicholas G., Renal function and renal afferent and efferent nerve activity, Am. J. Physiol. 1982, vol. 243, 1982 the American Physiological Society, pp. F425-F433.

Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.

Naropin (ropivacaine HCl) Injection, RX only Description, AstraZeneca 2001, 3 pages.

National High Blood Pressure Education Program, 1995 Update of the Working Group Reports on Chronic Renal Failure and Renovascular Hypertension, presentation, 13 pages.

National Kidney Foundation, Are You At Increased Risk for Chronic Kidney Disease?, 2002 National Kidney Foundation, Inc., 14 pages.

Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.

Nikolsky, Eugenia, M.D. et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.

Non-Final Office Action; U.S. Appl. No. 10/408,665; Mailed on Mar. 21, 2006, 14 pgs.

Non-Final Office Action; U.S. Appl. No. 11/129,765; Mailed on May 18, 2007, 10 pgs.

Non-Final Office Action; U.S. Appl. No. 11/129,765; Mailed on Sep. 10, 2007, 5 pgs.

Non-Final Office Action; U.S. Appl. No. 11/129,765; Mailed on Oct. 6, 2006, 30 pgs.

Non-Final Office Action; U.S. Appl. No. 11/133,925; Mailed on Oct. 8, 2008, 41 pgs.

Non-Final Office Action; U.S. Appl. No. 11/144,173; Mailed on Apr. 5, 2007, 33 pgs.

Non-Final Office Action; U.S. Appl. No. 11/144,173; Mailed on Sep. 10, 2007, 5 pgs.

Non-Final Office Action; U.S. Appl. No. 11/144,298; Mailed Oct. 29, 2009, 8 pgs.

Non-Final Office Action; U.S. Appl. No. 11/144,298; Mailed on Apr. 5, 2007, 33 pgs.

Non-Final Office Action; U.S. Appl. No. 11/144,298; Mailed on Sep. 10, 2007, 5 pgs.

Non-Final Office Action; U.S. Appl. No. 11/144,298; Mailed on Dec. 29, 2008, 7 pgs.

Non-Final Office Action; U.S. Appl. No. 11/145,122; Mailed on Apr. 11, 2007, 33 pgs.

Non-Final Office Action; U.S. Appl. No. 11/145,122; Mailed on Sep. 10, 2007, 5 pgs.

Non-Final Office Action; U.S. Appl. No. 11/189,563; Mailed on May 28, 2009, 5 pgs.

Non-Final Office Action; U.S. Appl. No. 11/233,814; Mailed on Jun. 17, 2008, 12 pgs.

Non-Final Office Action; U.S. Appl. No. 11/252,462; Mailed on Feb. 22, 2010, 6 pgs.

Non-Final Office Action; U.S. Appl. No. 11/266,993; Mailed on Jul. 8, 2009, 5 pgs.

Non-Final Office Action; U.S. Appl. No. 11/266,993; Mailed on Dec. 30, 2008, 7 pgs.

Non-Final Office Action; U.S. Appl. No. 11/363,867; Mailed on Sep. 25, 2008, 10 pgs.

Non-Final Office Action; U.S. Appl. No. 11/368,553; Mailed on May 18, 2010, 4 pgs.

Non-Final Office Action; U.S. Appl. No. 11/368,553; Mailed on Oct. 7, 2009, 5 pgs.

Non-Final Office Action; U.S. Appl. No. 11/368,809; Mailed on Dec. 3, 2009, 4 pgs.

Non-Final Office Action; U.S. Appl. No. 11/368,949; Mailed on Jun. 11, 2010, 6 pgs.

Non-Final Office Action; U.S. Appl. No. 11/368,971; Mailed on Aug. 24, 2010, 9 pgs.

Non-Final Office Action; U.S. Appl. No. 11/451,728; Mailed on Jun. 12, 2008, 41 pgs.

Non-Final Office Action; U.S. Appl. No. 11/451,728; Mailed on Jul. 2, 2009, 5 pgs.

Non-Final Office Action; U.S. Appl. No. 11/451,728; Mailed on Dec. 28, 2009, 7 pgs.

Non-Final Office Action; U.S. Appl. No. 11/504,117; Mailed on Mar. 31, 2009, 10 pgs.

Non-Final Office Action; U.S. Appl. No. 11/599,649; Mailed on Mar. 30, 2009, 10 pgs.

Non-Final Office Action; U.S. Appl. No. 11/599,649; Mailed on Jun. 23, 2008, 9 pgs.

Non-Final Office Action; U.S. Appl. No. 11/599,723; Mailed on Jun. 26, 2009, 17 pgs.

Non-Final Office Action; U.S. Appl. No. 11/599,723; Mailed on Oct. 15, 2010, 16 pgs.

Non-Final Office Action; U.S. Appl. No. 11/599,882; Mailed on Jul. 6, 2009, 13 pgs.

Non-Final Office Action; U.S. Appl. No. 11/688,178; Mailed on Jun. 28, 2010, 5 pgs.

Non-Final Office Action; U.S. Appl. No. 11/840,142; Mailed on Apr. 3, 2009, 13 pgs.

Non-Final Office Action; U.S. Appl. No. 12/567,521; Mailed on Sep. 3, 2010, 9 pgs.

Non-Final Office Action; U.S. Appl. No. 12/616,708; Mailed Sep. 16, 2010, 10 pgs.

Non-Final Office Action; U.S. Appl. No. 12/725,375; Mailed on Oct. 12, 2010, 14 pgs.

Nozawa, T.et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.

O'Hagan, K.P. et al., Renal denervation decreases blood pressure in DOCA-treated miniature swine with established hypertension, Am J Hypertens., 1990, 3:62-64.

Onesti, G. et al., Blood pressure regulation in end-stage renal disease and anephric man, Circ Res Suppl., 1975, 36 & 37: 145-152.

Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).

Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.

Page, I.H. et al., The Effect of Renal Denervation on the Level of Arterial Blood Pressure and Renal Function in Essential Hypertension. J Clin Invest. 1935;14:27-30.

Page, I.H., et al., The Effect of Renal Efficiencyof Lowering Arterial Blood Pressure in Cases of Essential Nephritis, Hospital of the Rockefeller Institue, Jul. 12, 1934, 7 pgs.

Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.

Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.

Pappone, Carlo et al., [2004][759] Pulmonary Vein Denervation Benefits Paroxysmal Atrial Fibrillation Patients after Circumferential Ablation, Abstract only. 1 page, Jan. 5, 2004.

Pappone, Carol and Santinelli, Vincenzo. Multielectrode basket catheter: A new tool for curing atrial fibrillation? Heart Rhythm, vol. 3, Issue 4, pp. 385-386. Apr. 2006.

Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.

Petersson, M. et al., Long-term outcome in relation to renal sympathetic activity in patients with chronic heart failure. Eur Heart J. 2005;26:906-13.

Pettersson, A. et al., Renal interaction between sympathetic activity and ANP in rats with chronic ischaemic heart failure, Nov. 25, 1988, Acta Physiol Scand 1989, 135, pp. 487-492.

PHCL 762 Pharmacology of the Autonomic Nervous System, Chapter 2 and 6.8 in Mosby, http://www.kumc.edu/research/medicine/pharmacology/CAI/phcl762.html, last accessed Aug. 24, 2004, 14 pgs.

Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.

Pliquett, U., Joule heating during solid tissue electroporation, Oct. 22, 2002, Med. Biol. Eng. Comput., 2003, vol. 41, pp. 215-219.

Podhajsky R.J. et al, The Histologic Effects of Pulsed and Continuous Radiofrequency Lesions at 42 C to Rat Dorsal Root Ganglion and Sciatic Nerve, SPINE, vol. 30, No. 9, pp. 1008-1013, 2005, Lippincott Williams & Wilkins Inc.

Pope, Jill. Fixing a Hole: Treating Injury by Repairing Cells. The New York Academy of Sciences. Jul. 6, 2006. 6 pgs.

Popovic, Jennifer R. and Margaret J. Hall, 1999 National Hospital Discharge Survey, Apr. 24, 2001, Advance Data, No. 319, CDC, pp. 1-17 & 20.

Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.

Programmable Infusion System, Pumps and Pump Selection, Medtronic Pain Therapies, Medtronic, Inc. Sep. 5, 2001, 2 pgs.

Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.

Pulmonary Concepts in Critical Care Breath Sounds, http://rnbob.tripod.com/breath.htm, last accessed Aug. 23, 2004, 5 pages.

Pulmonary Function Testing, http://ian.ucc.nau.edu/~daa/lecture/pft.htm, last accessed Aug. 23, 2004, 8 pages.

Purerfellner, Helmut and Martinek, Martin. Pulmonary vein stenosis following catheter ablation of atrial fibrillation. Current Opinion in Cardiology. 20; pp. 484-490. 2005.

Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.

Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.

Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.

Ravalia, A. et al., Tachyphylaxis and epidural anaesthesia, Edgware General Hospital, Correspondence, p. 529, Jun. 1989.

Renal Parenchymal Disease, Ch. 26, 5th Edition Heart Disease, A Textbook of Cardiovascular Medicine vol. 2, Edited by Eugene Braunwald, WB Saunders Company, pp. 824-825 1997.

Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.

Richebe, Philippe, M.D. et al., Immediate Early Genes after Pulsed Radiofrequency Treatment: Neurobiology in Need of Clinical Trials, Oct. 13, 2004, Anesthesiology Jan. 2005, vol. 102, No. 1, 2004 American Society of Anesthesiologists, Inc. Lippincott Williams & Wilkins, Inc., pp. 1-3.

Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.

Rosen, S.M. et al., Relationship of Vascular Reactivity to Plasma Renin Concentration in Patients with Terminal Renal Failure, Proc. Dialysis Transplant Forum 1974, pp. 45-47.

Roth, Bradley J. and Peter J. Basser, A Model of the Stimulation of a Nerve Fiber by Electromagnetic Induction, IEEE Transactions on Biomedical Engineering, vol. 37, No. 6, Jun. 1990, pp. 588-597.

Rudin, Asa, M.D. et al., Postoperative Epidural or Intravenous Analgesia after Major Abdominal or Thoraco-Abdominal Surgery, The Journal of the American Society of Anesthesiologists, Inc., Anesthesiology 2001, vol. 95, A-970, 1 page.

Rudnick, Michael R. et al., Contrast-induced nephropathy: How it develops, how to prevent it, Cleveland Clinic Journal of Medicine Jan. 2006, vol. 73, No. 1, pp. 75-87.

Rump, L.C., The Role of Sympathetic Nervous Activity in Chronic Renal Failure, J Clinical Basic Cardiology 2001, vol. 4, pp. 179-182.

Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.

Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.

Sabbah, Hani N., Animal Models for Heart Failure and Device Development, Henry Ford Health System. 24 slides, Oct. 17, 2005.

Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.

Schauerte, P et al., Catheter ablation of cardiac autonomic nerves for prevention of vagal atrial fibrillation, Circulation. 102(22). Nov. 28, 2000. Abstract only. 2 pgs.

Schauerte, P et al., Transvenous parasympathetic nerve stimulation in the inferior vena cava and atrioventricular conduction, Journal of Cardiovascular Electrophysiology. 11(1). Jan. 2000. Abstract only. 2 pgs.

Scheiner, Avram, Ph.D., The design, development and implementation of electrodes used for functional electrial stimulation, Thesis paper, Case Western Reserve University, May 1992, 220 pages.

Scherlag, BJ and Po, S., The intrinsic cardiac nervous system and atrial fibrillation, Current Opinion in Cardiology. 21(1):51-54, Jan. 2006. Abstract only. 2 pgs.

Schlaich, M.P. et al., Relation between cardiac sympathetic activity and hypertensive left ventricular hypertrophy. Circulation. 2003;108:560-5.

Schlaich, M.P. et al., Sympathetic augmentation in hypertension: role of nerve firing, norepinephrine reuptake, and angiotensin neuromodulation, Hypertension, 2004, 43:169-175.

Schmitt, Joseph et al., Intravascular Optical Coherence Tomography—Opening a Window into Coronary Artery Disease, LightLab Imaging, Inc. Business Briefing: European Cardiology 2005.

Schoenbach, Karl H. et al, Intracellular Effect of Ultrashort Electrical Pulses, Dec. 26, 2000, Bioelectromagnetics, vol. 22, 2001, Wiley-Liss, Inc. 2001, pp. 440-448.

Schrier, Robert et al., Cardiac and Renal Effects of Standard Versus Rigorous Blood Pressure Control in Autosomal-Dominant Polycistic Kidney Disease, Mar. 23, 2002, Journal of the American Society of Nephrology, American Society of Nephrology 2002, pp. 1733-1739.

Scremin, Oscar U., M.D., Ph.D. and Daniel P. Holschneider, M.D., 31 & 32.. An Implantable Bolus Infusion Pump for the Neurosciences, FRP, 3 pages, Apr. 2005, 3 pages.

Sensorcaine—MPF Spinal Injection, informational document, AstraZeneca 2001, 2 pgs.

Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.

Shannon, J.L. et al., Studies on the innervation of human renal allografts, J Pathol. 1998, vol. 186, pp. 109-115.

Shlipak, M.G. et al., The clinical challenge of cardiorenal syndrome. Circulation. 2004;110:1514-7.

Shupak, Naomi M., Therapeutic Uses of Pulsed Magnetic-Field Exposure: A Review, Radio Science Bulletin Dec. 2003, No. 307, pp. 9-32.

Shu-Qing, Liu et al., Old spinal cord injury treated by pulsed electric stimulation, General Hospital of Beijing Command, Beijing, 5 pages (full article in Chinese; abstract on last page) Dec. 6, 1990.

Siegel, RJ et al., Clinical demonstration that catheter-delivered ultrasound energy reverses arterial vasoconstriction, Journal of the American College of Cardiology. 1992. 20; 732-735. Summary only. 2 pgs.

Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.

Sisken, B.F. et al., 229.17 Influence of Non-Thermal Pulsed Radiofrequency Fields (PRF) on Neurite Outgrowth, Society for Neuroscience, vol. 21, 1995, 2 pages.

Skeie, B. et al., Effect of chronic bupivacaine infusion on seizure threshold to bupivacaine, Dec. 28, 1986, Acta Anaesthesiol Scand 1987, vol. 31, pp. 423-425.

Skopec, M., A Primer on Medical Device Interactions with Magnetic Resonance Imaging Systems, Feb. 4 1997, CDRH Magnetic Resonance Working Group, U.S. Department of Heatlh and Human Services, Food and Drug Administration, Center for Devices and Radiological Health, Updated May 23, 1997, 17 pages, http://www.fda.gov/cdrh/ode/primerf6.html, (last accessed Jan. 23, 2006.

Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.

Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.

Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.

Sluijter, M.D., Ph.D., Radiofrequency Part 2: Thoracic and Cervical Region, Headache and Facial Pain, various pages from, FlivoPress SA, Meggen (LU), Switzerland, 13 pages 2002.

Sluijter, M.D., Ph.D., The Role of Radiofrequency in Failed Back Surgery Patients, Current Review of Pain 2000, vol. 4, 2000 by Current Science Inc., pp. 49-53.

Smithwick, R.H. et al., Hypertension and associated cardiovascular disease: comparison of male and female mortality rates and their influence on selection of therapy, JAMA, 1956, 160:1023-1033.

Smithwick, R.H. et al., Splanchnicectomy for essential hypertension, Journal Am Med Assn, 1953;152:1501-1504.

Smithwick, R.H., Surgical treatment of hypertension, Am J Med 1948, 4:744-759.

Sobotka, Paul A., Treatment Strategies for Fluid Overload, CHF Patients, CHF Solutions. Transcatheter Cardiovascular Therapeutics 2005. 20 slides.

Solis-Herruzo, J.A. et al., Effects of lumbar sympathetic block on kidney function in cirrhotic patients with hepatorenal syndrome, Journal of Hepatology, 1987; 5: 167-173.

Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.

Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.

Steffen, W. et al., Catheter-delivered high intensity, low frequency ultrasound induces vasodilation in vivo, European Heart Journal. 1994. 15;pp. 369-376.

Steg, PG et al., Pulsed ultraviolet laser irradiation produces endothelium-independent relaxation of vascular smooth muscle, Circulation: Journal of the American Heart Association. 1989. pp. 189-197.

Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.

Strojek, K. et al., Lowering of microalbuminuria in diabetic patients by a sympathicoplegic agent: novel approach to prevent progression of diabetic nephropathy? J Am Soc Nephrol. 2001;12:602-5.

Summary, Critical Reviews in Biomedical Engineering, vol. 17, Issue 5, 1989, pp. 515-529.

Sung, Duk Hyun, M.D. et al., Phenol Block of Peripheral Nerve Conduction: Titrating for Optimum Effect, Jun. 27, 2000, Arch. Phys. Med. Rehabil. vol. 82, May 2001, pp. 671-676.

Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.

Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.

Tamborero, David et al., Incidence of Pulmonary Vein Stenosis in Patients Submitted to Atrial Fibrillation Ablation: A Comparison of the Selective Segmental Ostial Ablation vs. the Circumferential Pulmonary Veins Ablation, Journal of Intervocational Cardiac Electrophysiology. 14; pp. 41-25. 2005.

Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.

Terashima, Mitsuyasu et al. Feasibility and Safety of a Novel CryoPlasty™ System. Poster. 1 page, Mar. 15, 2002.

Thatipelli et al., CT Angiography of Renal Artery Anatomy for Evaluating Embolic Protection Devices, Journal of Vascular and Interventional Radiology, Jul. 2007, pp. 842-846.

The Antihypertensive and Lipid-Lowering Treatment to Prevent Heart Attack Trial, ALLHAT Research Group, JAMA, 2002, vol. 288, pp. 2981-2997.

Thomas, John R. and Oakley, E. Howard N. Chapter 15: Nonfreezing Cold Injury Medical Aspects of Harsh Environments, vol. 1. pp. 467-490, 2001.

Thompson, Gregory W., et al., Bradycardia Induced by Intravascular Versus Direct Stimulation of the Vagus Nerve, Aug. 24, 1997, The Society of Thoracic Surgeons 1998, pp. 637-642.

Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.

Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.

Trapani, Angelo J. et al., Neurohumoral interactions in conscious dehydrated rabbit, Am. J. Physiol. 254, 1988, the American Physiological Society 1988, pp. R338-R347.

Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.

Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.

Trumble, Dennis R. and James A. MaGovern, Comparison of Dog and Pig Models for Testing Substernal Cardiac Compression Devices, Nov. 2003, ASAIO Journal 2004, pp. 188-192.

Tsai, E., Intrathecal drug delivery for pain indications, technique, results, Pain Lecture presentation, Jun. 8, 2001, 31 pages.

Uematsu, Toshihiko, M.D., Ph.D., F.I.C.A. et al., Extrinsic Innervation of the Canine Superior Vena Cava, Pulmonary, Portal and Renal Veins, Angiology—Journal of Vascular Diseases, Aug. 1984, pp. 486-493.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.

Valente, John F. et al., Laparoscopic renal denervation for intractable ADPKD-related pain, Aug. 24, 2000, Nephrol Dial Transplant 2001, vol. 16, European Renal Association-European Dialysis and Transplant Association, p. 160.

Van Antwerp, Bill and Poonam Gulati, Protein Delivery from Mechanical Devices Challenges and Opportunities, Medtronic presentation, 19 pages, Jul. 2003.

Velazquez, Eric J., An international perspective on heart failure and left ventricular systolic dysfunction complicating myocardial infarction: the VALIANT registry, Aug. 5, 2004, European Heart Journal vol. 25, 2004 Elsevier, pp. 1911-1919.

Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.

Villarreal, Daniel et al., Effects of renal denervation on postprandial sodium excretion in experimental heart failure, Oct. 29, 1993, Am J Physiol 266, 1994, pp. R1599-R1604.

Villarreal, Daniel et al., Neurohumoral modulators and sodium balance in experimental heart failure, Nov. 6, 1992, Am. J. Physiol, vol. 264, 1993, pp. H1187-H1193.

Vonend, O. et al., Moxonidine treatment of hypertensive patients with advanced renal failure. J Hypertens. 2003;21:1709-17.

Wagner, C.D. et al., Very low frequency oscillations in arterial blood pressure after autonomic blockade in conscious dogs, Feb. 5, 1997, Am J Physiol Regul Integr Comp Physiol 1997, vol. 272, 1997 the American Physiological Society, pp. 2034-2039.

Wald, Jan D., Ph.D, et al., Cardiology Update: 2003, Sep. 11, 2003, AG Edwards 2003, 120 pages.

Wang, Xi et al., Alterations of adenylyl cyclase and G proteins in aortocaval shunt-induced heart failure, Jul. 2004, Am J Physiol Heart Circ Physiol vol. 287, 2004 the American Physiological Society, pp. H118-H125.

Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.

Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.

Weiner, Richard L., M.D., Peripheral nerve neurostimulation, Neurosurg. Clin. N. Am. vol. 14, 2003, Elsevier, Inc. 2003, pp. 401-408.

Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.

Whitelaw, G.P., Kinsey, D., Smithwick, R.H., Factors influencing the choice of treatment in essential hypertension: surgical, medical, or a combination of both, Am J Surg, 1964, 107:220-231.

Wilson, D.H. et al., The Effects of Pulsed Electromagnetic Energy on Peripheral Nerve Regeneration, Annals New York Academy of Sciences, pp. 575-585, Oct. 1974.

Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.

Wyss, J. Michael et al., Neuronal control of the kidney: Contribution to hypertension, Apr. 8, 1991, Can. J. Physiol. Pharmacol. 1992;70: 759-770.

Yamaguchi, Jun-ichi, M.D. et al., Prognostic Significance of Serum Creatinine Concentration for In-Hospital Mortality in Patients with Acute Myocardial Infarction Who Underwent Successful Primary Percutaneous Coronary Intervention (from the Heart Institute of Japan Acute Myocardial Infarction [HIJAMI] Registry), Feb. 24, 2004, The American Journal of Cardiology vol. 93, Jun. 15, 2004, 2004 by Excerpta Medica, Inc., pp. 1526-1528.

Ye, Richard D., M.D., Ph.D., Pharmacology of the Peripheral Nervous System, E-425 MSB, 6 pages, Jan. 2000.

Ye, S. et al., A limited renal injury may cause a permanent form of neurogenic hypertension. Am J Hypertens. 1998;11:723-8.

Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.

Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.

Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.

Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001. pp. 887-892.

Zanchetti, A. et al., Neural Control of the Kidney—Are There Reno-Renal Reflexes?, Clin. And Exper. Hyper. Theory and Practice, A6 (1&2), 1984, Marcel Dekker, Inc. 1984, pp. 275-286.

Zanchetti, A. et al., Practice Guidelines for Primary Care Physicians: 2003 ESH/ESC Hypertension Guidelines, Journal of Hypertension, vol. 21, No. 10, 2003, pp. 1779-1786.

Zanchetti, A.S., Neural regulation of renin release: Experimental evidence and clinical implications in arterial hypertension, Circulation, 1977, 56(5) 691-698.

Zimmermann, Ulrich, Electrical Breakdown, Electropermeabilization and Electrofusion, Rev. Physiol. Biochem. Pharmacol., vol. 105, Springer-Verlag 1986, pp. 175-256.

Zoccali, C. et al., Plasma norepinephrine predicts survival and incident cardiovascular events in patients with end-stage renal disease. Circulation. 2002;105:1354-9.

Zucker, Irving H. et al., The origin of sympathetic outflow in heart failure: the roles of angiotensin II and nitric oxide, Progress in Biophysics & Molecular Biology, vol. 84, 2004, Elsevier Ltd. 2003, pp. 217-232.

Zundert, Jan Van, M.D. Fipp and Alex Cahana, M.D. Daapm, Pulsed Radiofrequency in Chronic Pain Management: Looking for the Best Use of Electrical Current, Pain Practice 2005, vol. 5, Issue 2, 2005 World Institute of Pain, pp. 74-76.

Schneider, Peter A.., "Endovascular Skills—Guidewires, Catheters, Arteriography, Balloon Angioplasty, Stents", pp. 70-71, 101 and 188-190 (1998).

Kandarpa, Krishna et al., "Handbook of Interventional Radiologic Procedures", Third Edition, pp. 194-210 (2002).

ThermoCool Irrigated Catheter and Integrated Ablation System, Biosense Webster (2006).

ClinicalTrials.gov, Renal Denervation in Patients with uncontrolled Hypertension in Chinese (2011), www.clinicaltrials.gov/ct2/show/NCT01390831.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Blessing, Erwin et al., Cardiac Ablation and Renal Denervation Systems Have Distinct Purposes and Different Technical Requirements, JACC Cardiovascular Interventions, vol. 6, No. 3, 2013.

Mount Sinai School of Medicine clinical trial for Impact of Renal Sympathetic Denervation of Chronic Hypertenion, Mar. 2013, http://clinicaltrials.gov/ct2/show/NCT01628198.

Prochnau, Dirk et al., Catheter-based renal denervation for drug-resistant hypertension by using a standard electrophysiology catheter; EuroIntervention 2012, vol. 7, pp. 1077-1080.

Implantable Neurostimulation Systems, Medtronic Neurological, http://medtronic.com/neuro/paintherapies/pain_treatment_ladder/pdf/implantable_brochure.pd; Jan. 18, 1999.

European Search Report dated Jan. 30, 2013; European Application No. 12180426.4; Applicant: Medtronic Ardian Luxembourg S.a.r.l.; 6 pages.

European Search Report dated Feb. 28, 2013; European Application No. 12180427.2; Applicant: Medtronic Ardian Luxembourg S.a.r.l.; 4 pages.

European Search Report dated Jan. 30, 2013; Application No. 12180428.0; Applicant: Medtronic Ardian Luxembourg S.a.r.l.; 6 pages.

European Search Report dated Jan. 30, 2013; Application No. 12180430.6; Applicant: Medtronic Ardian Luxembourg S.a.r.l.; 6 pages.

European Search Report dated Feb. 22, 2013; Application No. 12180432.2; Applicant: Medtronic Ardian Luxembourg S.a.r.l.; 6 pages.

European Search Report dated Jan. 30, 2013; Application No. 12180431.4; Applicant: Medtronic Ardian Luxembourg S.a.r.l.; 6 pages.

European Search Report dated May 3, 2012; European Patent Application No. 11192514.5; Applicant: Ardian, Inc.; 7 pages.

Gelfand, M., et al., "Treatment of renal failure and hypertension." U.S. Provisional Patent Application No. 60-442,970.

Hall, W. H., et al. "Combined embolization and percutaneous radiofrequency ablation of a solid renal tumor." Am. J. Roentgenol,174: 1592-1594 (2000).

Hendee, W. R. et al. "Use of Animals in Biomedical Research: The Challenge and Response." American Medical Association White Paper (1988).

Medical-Dictionary.com, Definition of "Animal Model," http:--medical-dictionary.com (search "Animal Model"), 2005.

Medtronic, Inc., Annual Report (Form 10-K) (Jun. 28, 2011).

Ong, K. L., et al. "Prevalence, Awareness, Treatment, and Control of Hypertension Among United States Adults 1999-2004." Hypertension, 49: 69-75 (2007) (originally published online Dec. 11, 2006).

Renal Denervation (RDN), Symplicity RDN System Common Q&A (2011), http:--www.medtronic.com-rdn-mediakit-RDN%20FAQ.pdf.

"Implantable Neurostimulation Systems," Medtronic Neurological, http://medtronic.com/neuro/paintherapies/pain_treatment_ladder/pdf/implantable_brochure.pdf; Jan. 18, 1999.

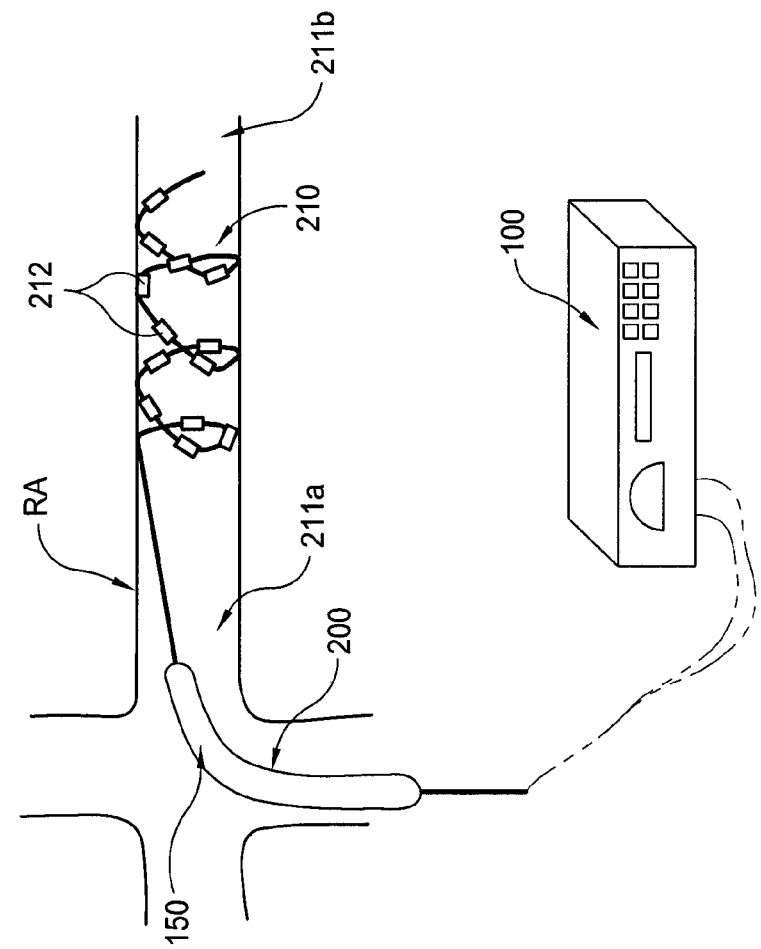
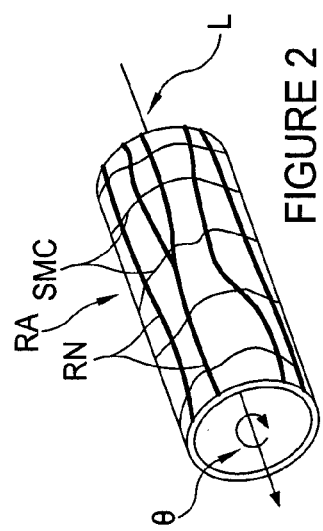
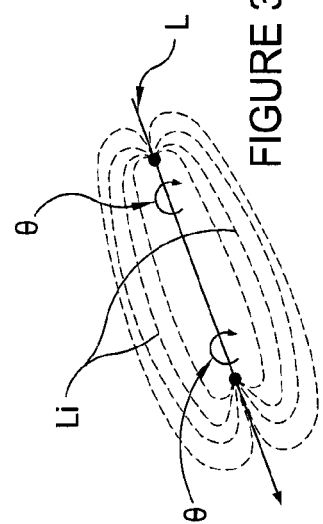
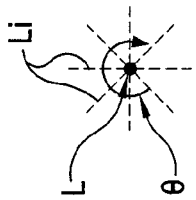

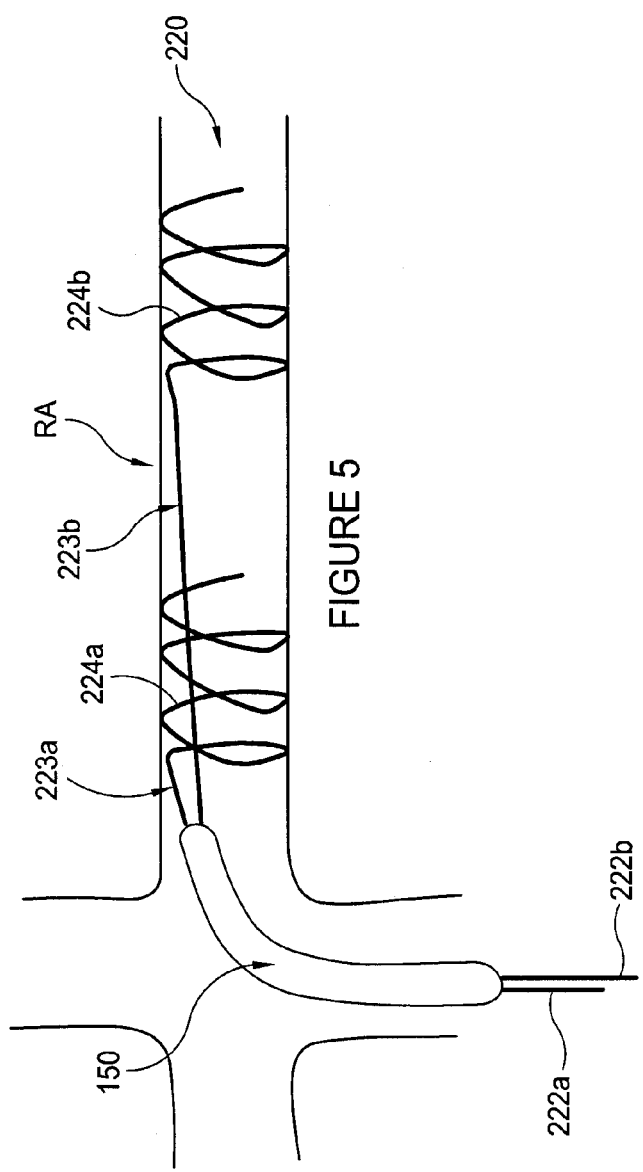
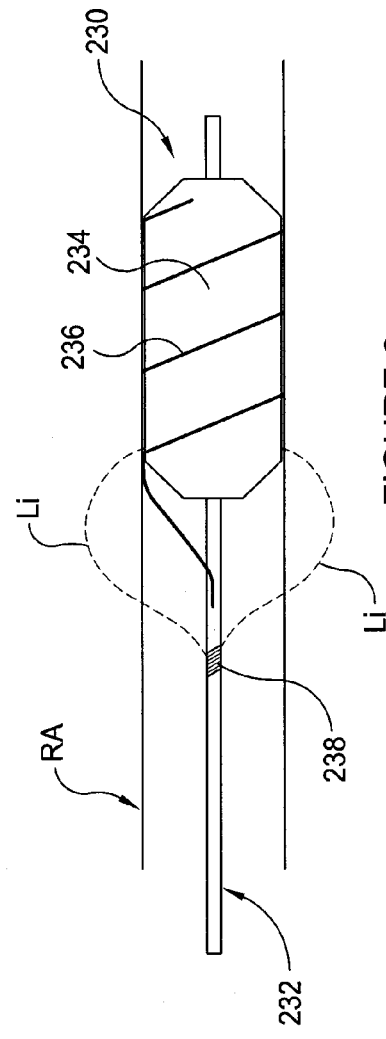

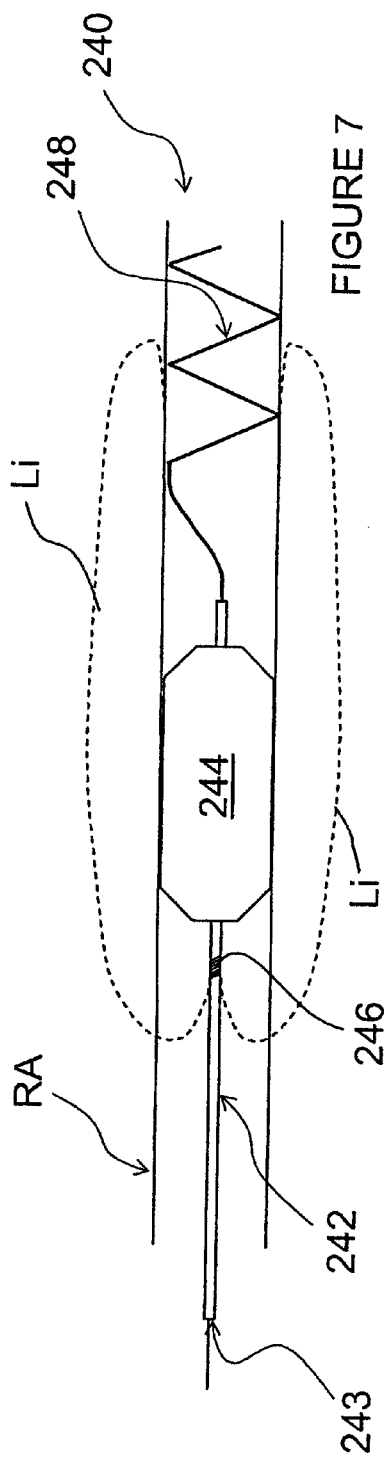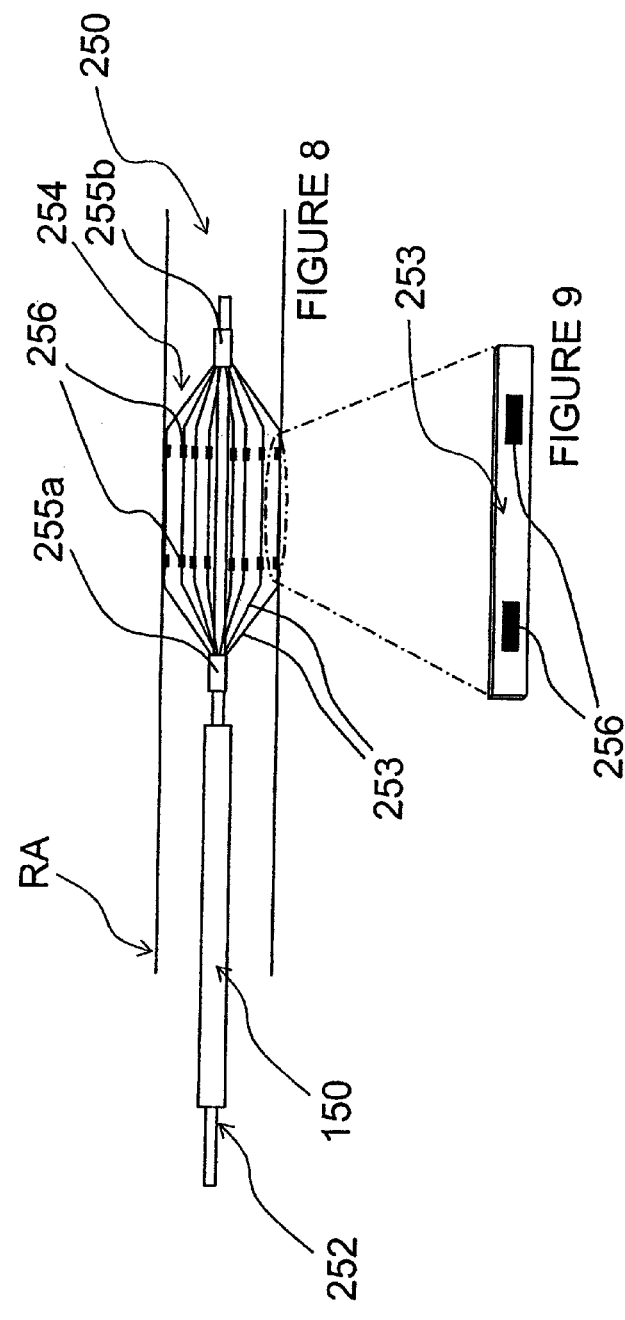

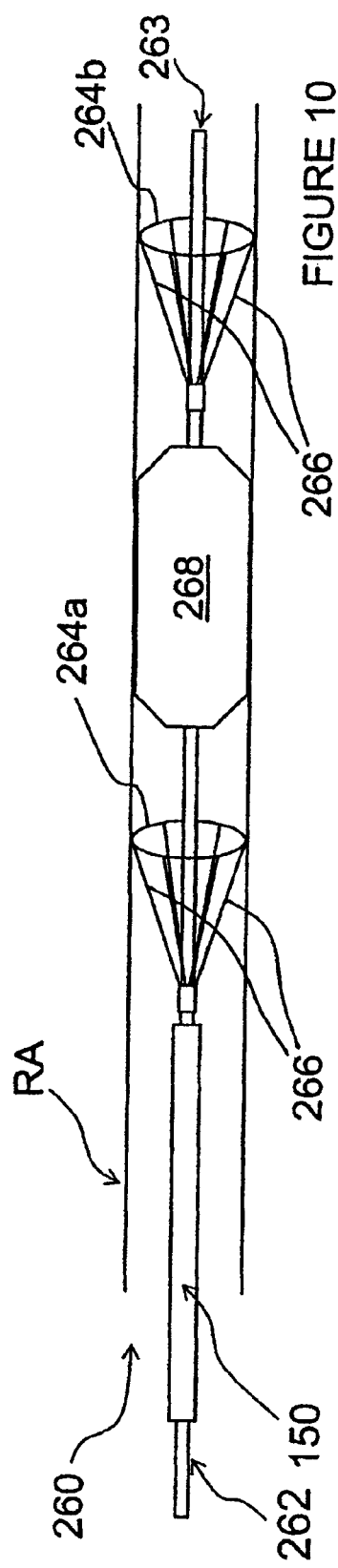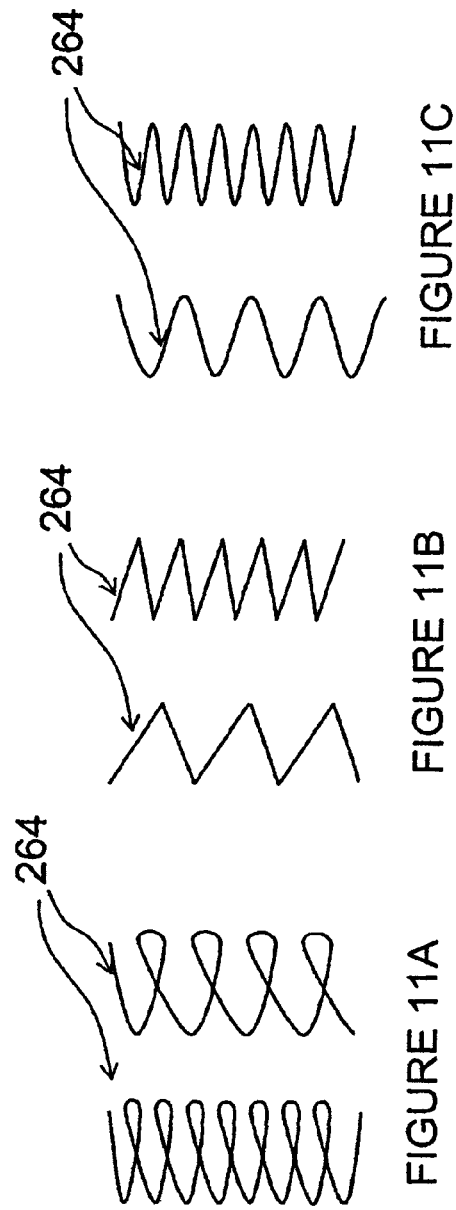

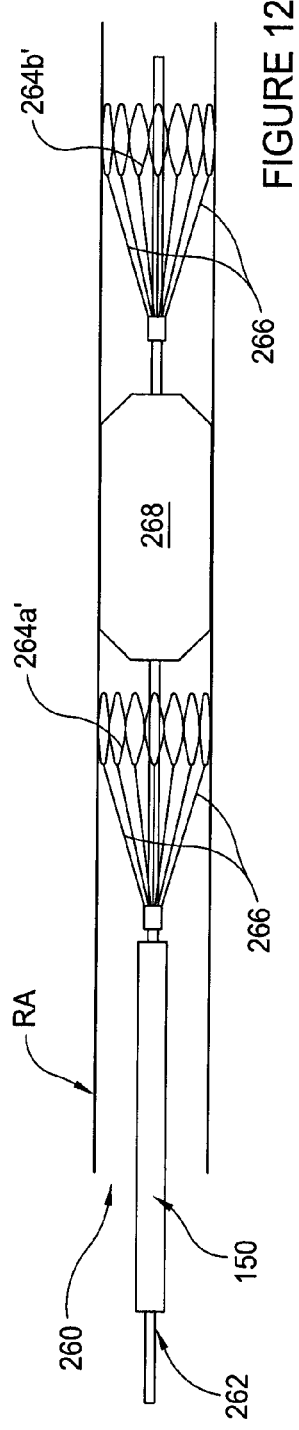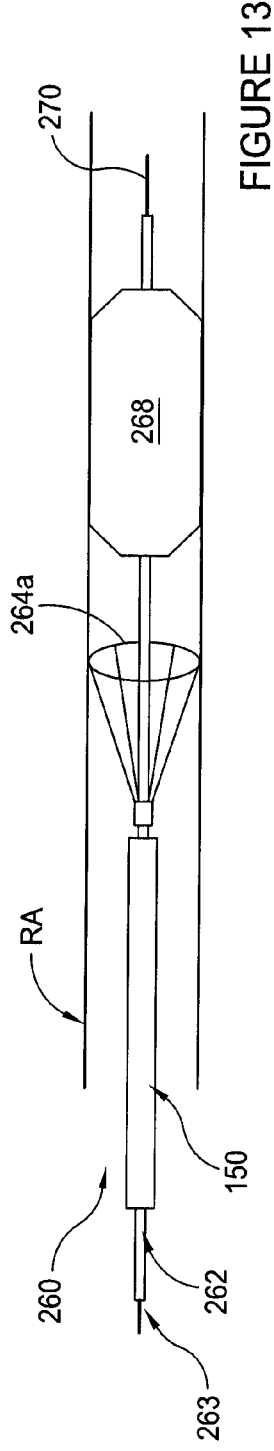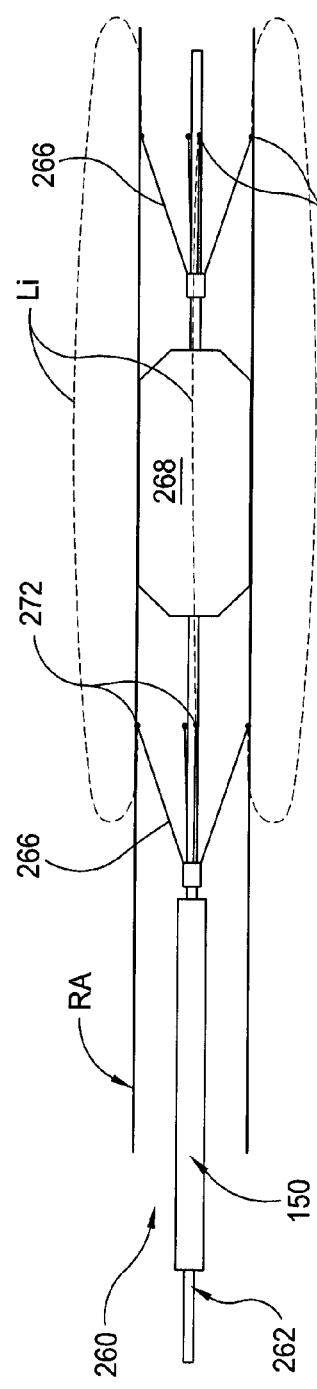

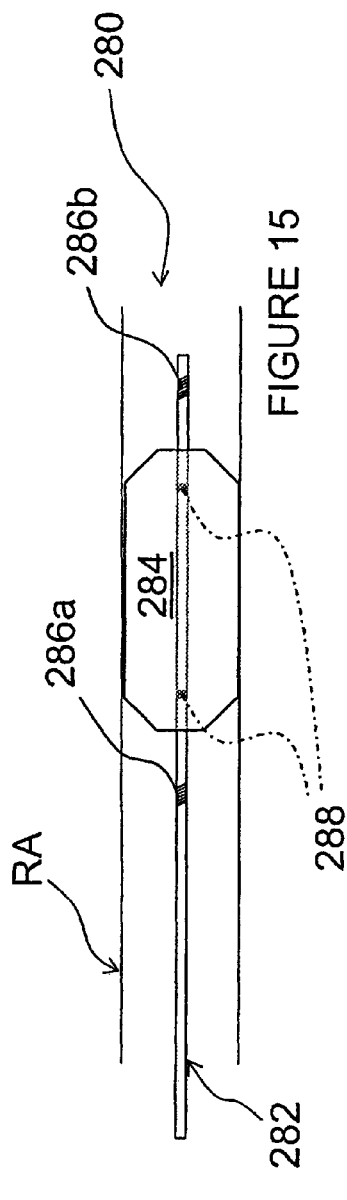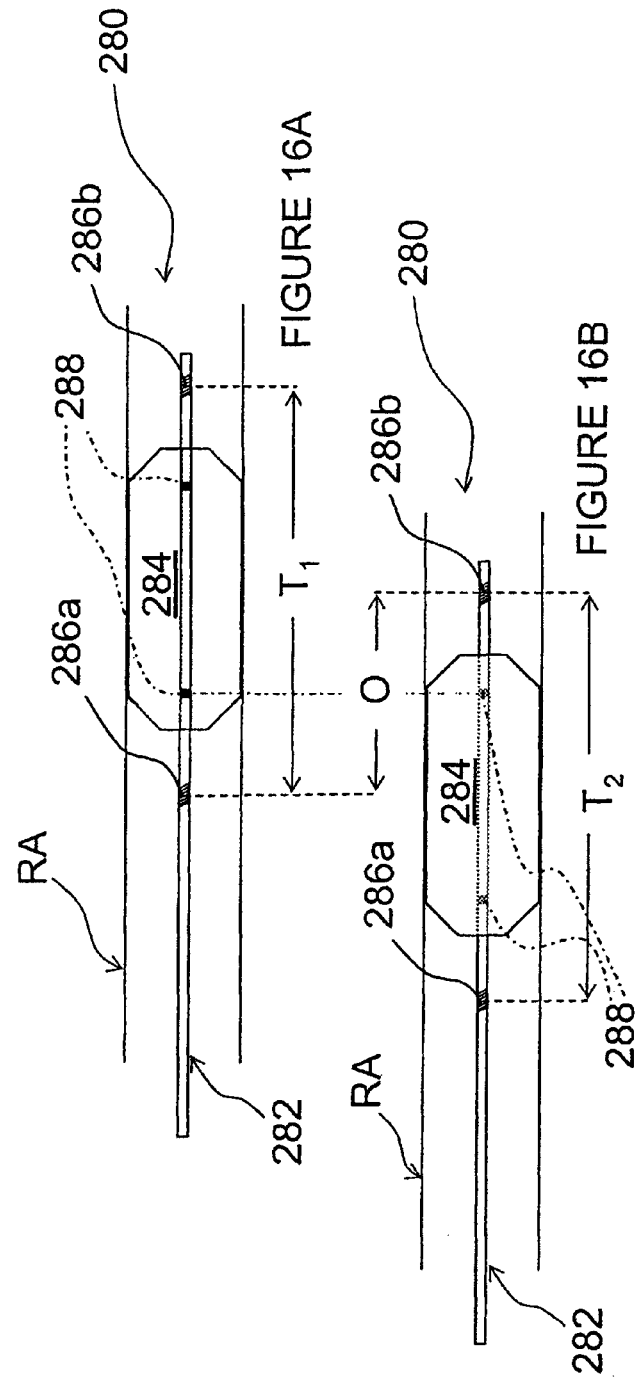

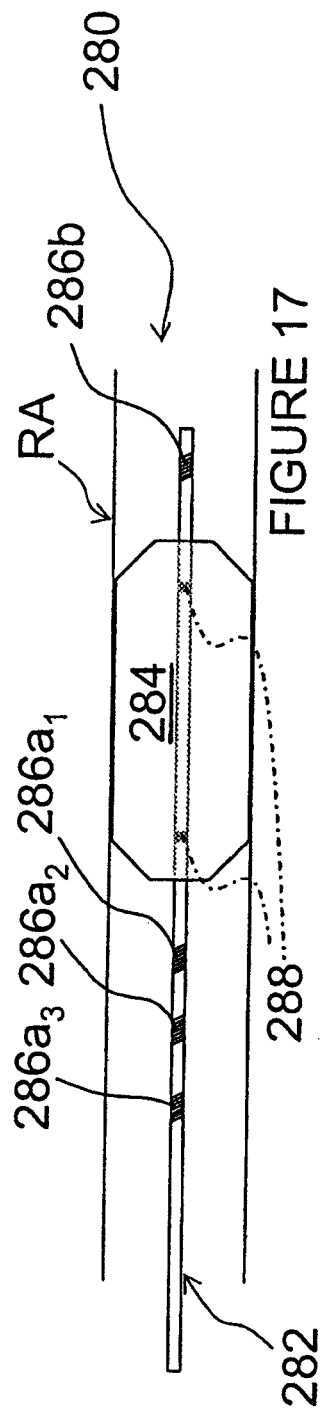
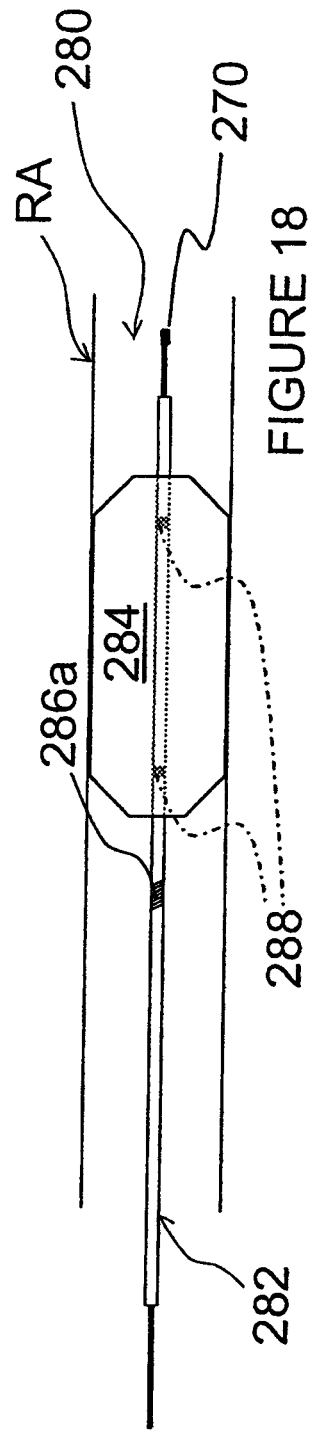

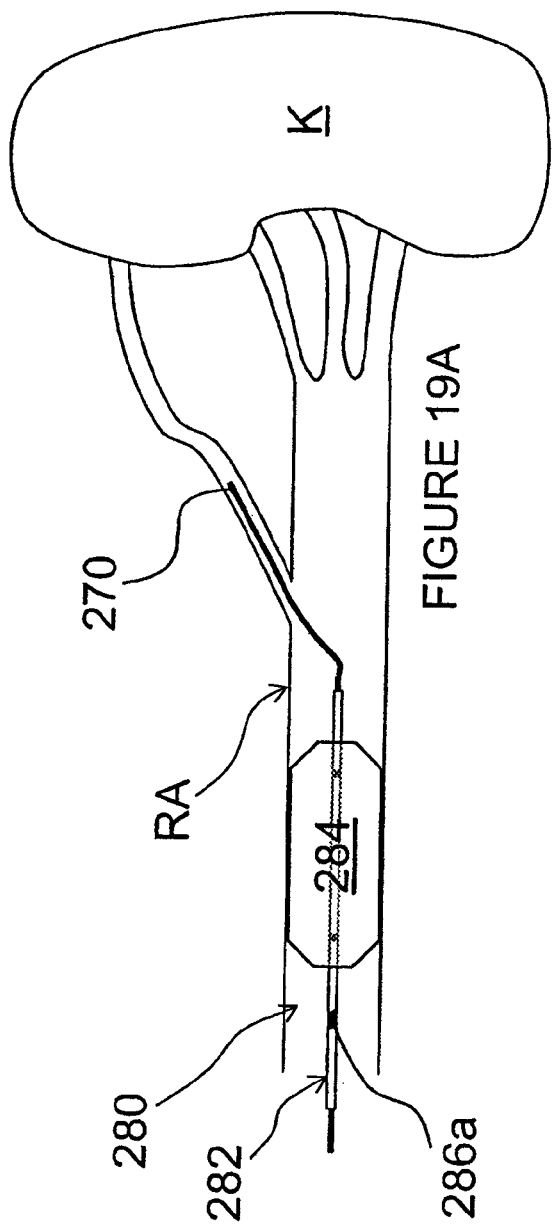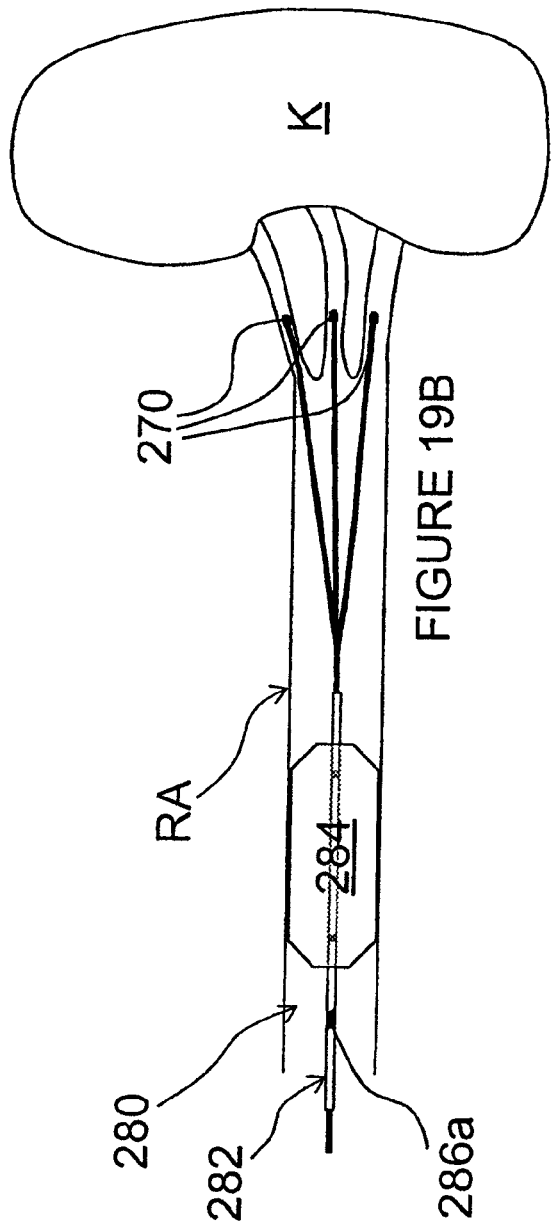

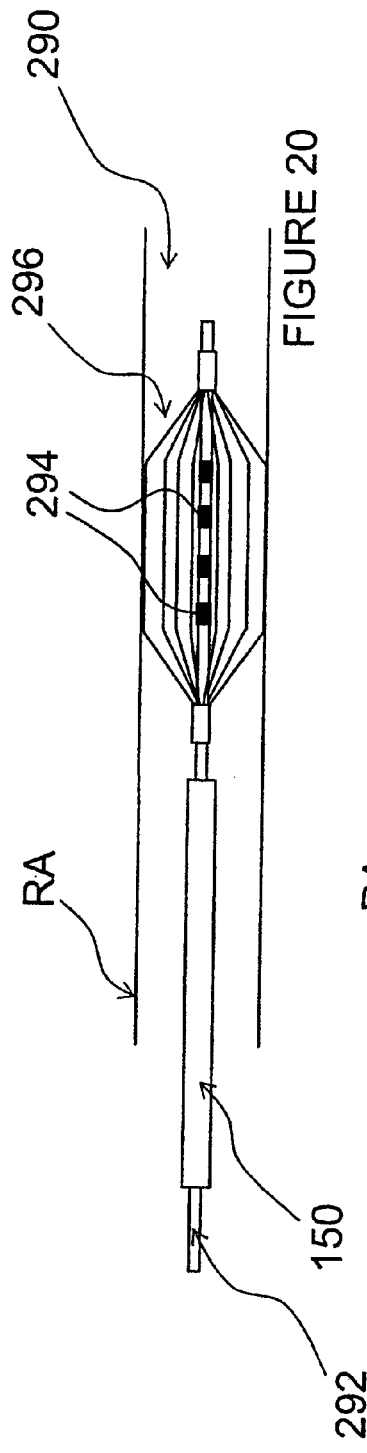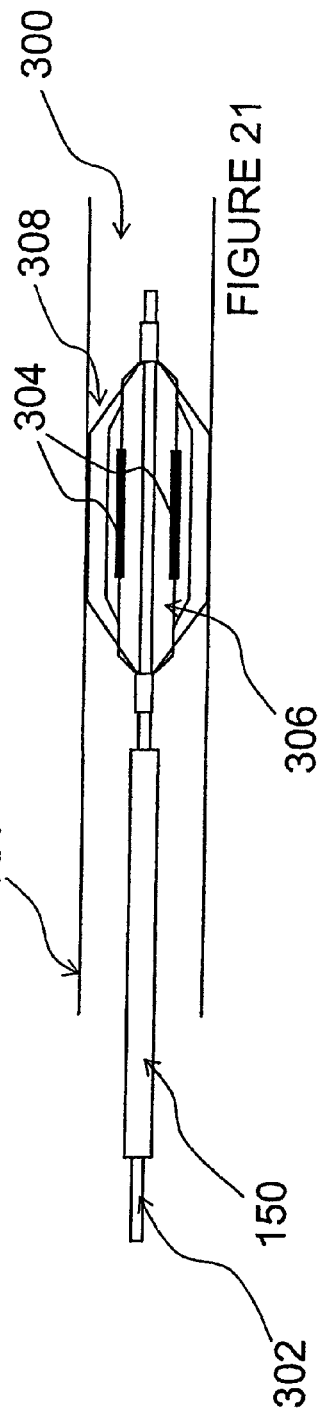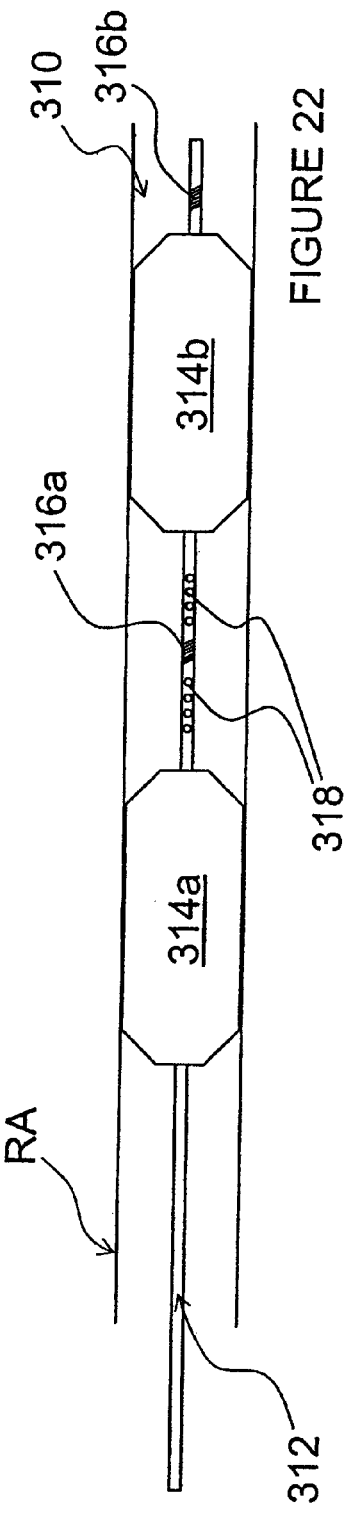

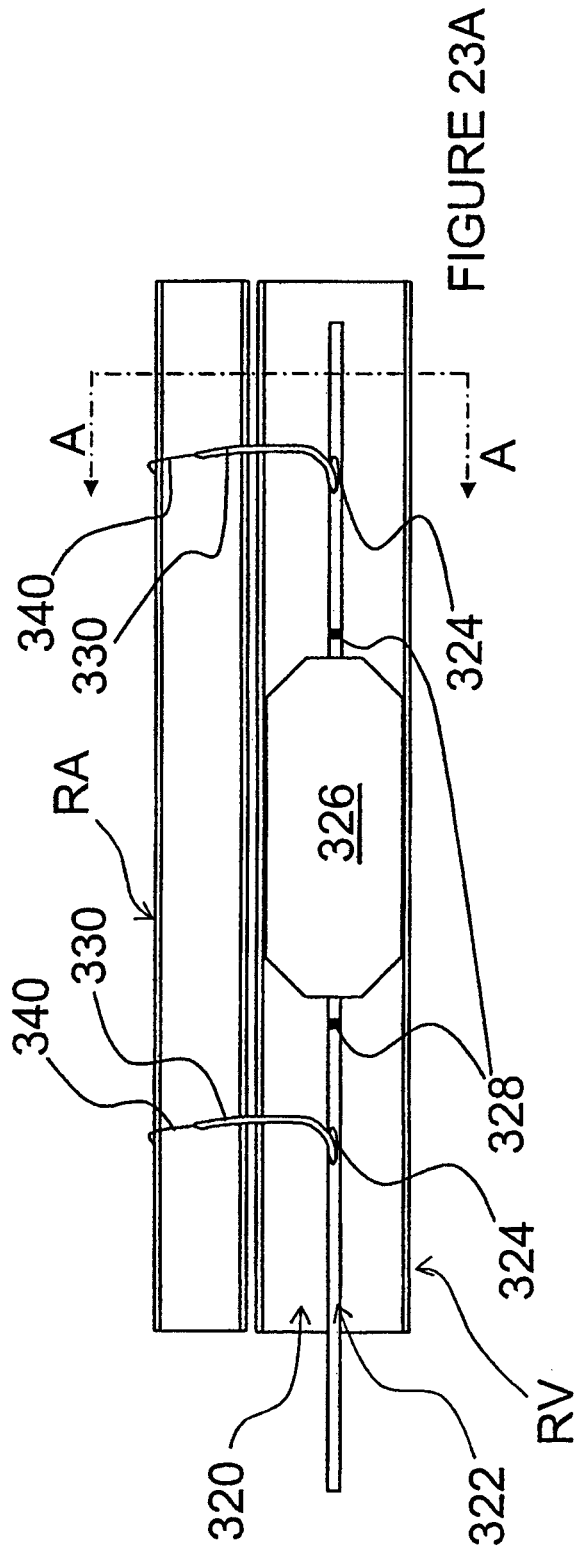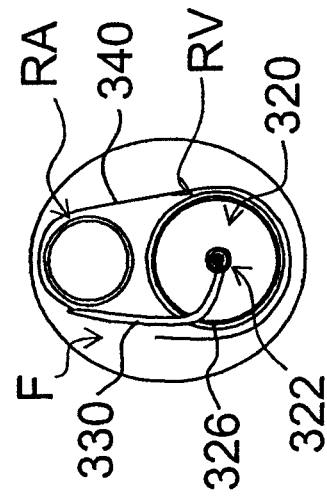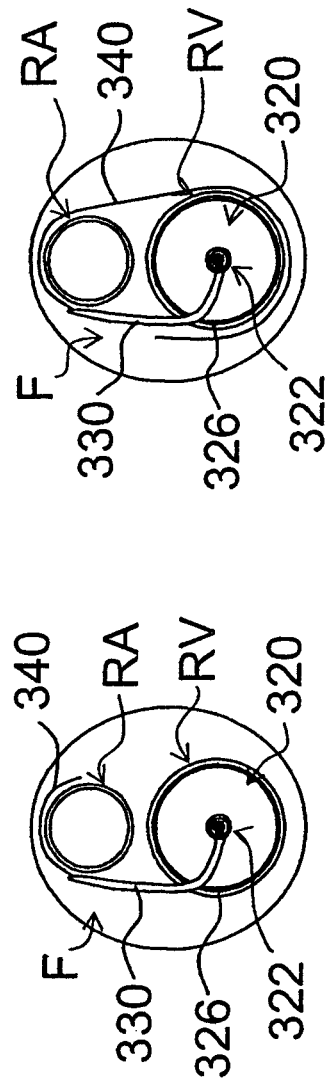
FIGURE 23A
FIGURE 23B
FIGURE 23C

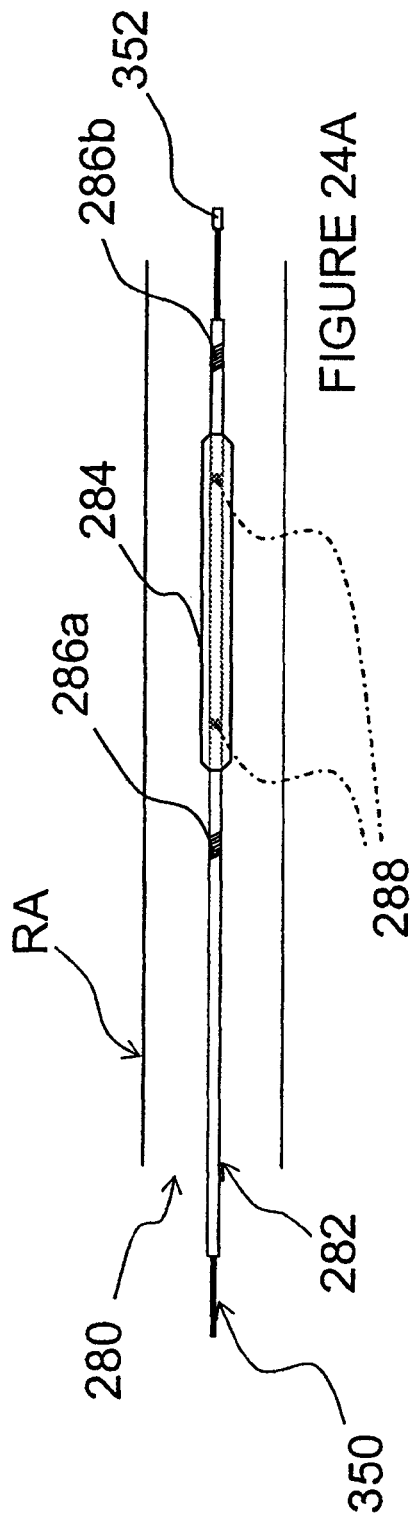
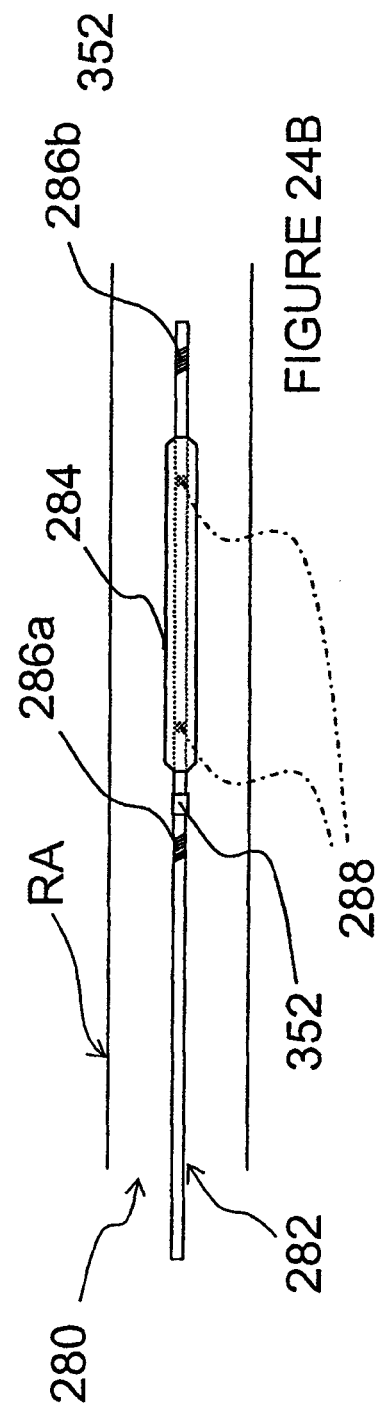

APPARATUSES FOR RENAL NEUROMODULATION AND ASSOCIATED SYSTEMS AND METHODS

CROSS-REFERENCE TO RELATED APPLICATIONS

The present application is a continuation of U.S. patent application Ser. No. 12/777,892, filed May 11, 2010, which is a continuation of U.S. patent application Ser. No. 11/782,451, filed Jul. 24, 2007, now abandoned, which is a divisional of U.S. patent application Ser. No. 11/129,765, filed May 13, 2005, now U.S. Pat. No. 7,653,438, which claims the benefit of U.S. Provisional Patent Application No. 60/616,254, filed Oct. 5, 2004; and U.S. Provisional Patent Application No. 60/624,793, filed Nov. 2, 2004.

U.S. patent application Ser. No. 11/129,765, filed May 13, 2005, now U.S. Pat. No. 7,653,438 is also a continuation-in-part of U.S. patent application Ser. No. 10/408,665, filed Apr. 8, 2003, now U.S. Pat. No. 7,162,303, which claims the benefit of U.S. Provisional Patent Application Nos. (a) 60/370,190, filed Apr. 8, 2002; (b) 60/415,575, filed Oct. 3, 2002; and (c) 60/442,970, filed Jan. 29, 2003. The disclosures of these applications are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for renal neuromodulation. More particularly, the present invention relates to methods and apparatus for achieving renal neuromodulation via a pulsed electric field and/or electroporation or electrofusion.

BACKGROUND

Congestive Heart Failure ("CHF") is a condition that occurs when the heart becomes damaged and reduces blood flow to the organs of the body. If blood flow decreases sufficiently, kidney function becomes impaired and results in fluid retention, abnormal hormone secretions and increased constriction of blood vessels. These results increase the workload of the heart and further decrease the capacity of the heart to pump blood through the kidney and circulatory system.

This reduced capacity further reduces blood flow to the kidney, which in turn further reduces the capacity of the heart. It is believed that progressively decreasing perfusion of the kidney is a principal non-cardiac cause perpetuating the downward spiral of CHF. Moreover, the fluid overload and associated clinical symptoms resulting from these physiologic changes are predominant causes for excessive hospital admissions, terrible quality of life and overwhelming costs to the health care system due to CHF.

While many different diseases may initially damage the heart, once present, CHF is split into two types: Chronic CHF and Acute (or Decompensated-Chronic) CHF. Chronic Congestive Heart Failure is a longer term, slowly progressive, degenerative disease. Over years, chronic congestive heart failure leads to cardiac insufficiency. Chronic CHF is clinically categorized by the patient's ability to exercise or perform normal activities of daily living (such as defined by the New York Heart Association Functional Class). Chronic CHF patients are usually managed on an outpatient basis, typically with drugs.

Chronic CHF patients may experience an abrupt, severe deterioration in heart function, termed Acute Congestive Heart Failure, resulting in the inability of the heart to maintain sufficient blood flow and pressure to keep vital organs of the body alive. These Acute CHF deteriorations can occur when extra stress (such as an infection or excessive fluid overload) significantly increases the workload on the heart in a stable chronic CHF patient. In contrast to the stepwise downward progression of chronic CHF, a patient suffering acute CHF may deteriorate from even the earliest stages of CHF to severe hemodynamic collapse. In addition, Acute CHF can occur within hours or days following an Acute Myocardial Infarction ("AMI"), which is a sudden, irreversible injury to the heart muscle, commonly referred to as a heart attack.

As mentioned, the kidneys play a significant role in the progression of CHF, as well as in Chronic Renal Failure ("CRF"), End-Stage Renal Disease ("ESRD"), hypertension (pathologically high blood pressure) and other cardio-renal diseases. The functions of the kidney can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions resulting from reduced renal function or renal failure (kidney failure) are believed to increase the workload of the heart. In a CHF patient, renal failure will cause the heart to further deteriorate as the water build-up and blood toxins accumulate due to the poorly functioning kidneys and, in turn, cause the heart further harm.

The primary functional unit of the kidneys that is involved in urine formation is called the "nephron". Each kidney consists of about one million nephrons. The nephron is made up of a glomerulus and its tubules, which can be separated into a number of sections: the proximal tubule, the medullary loop (loop of Henle), and the distal tubule. Each nephron is surrounded by different types of cells that have the ability to secrete several substances and hormones (such as renin and erythropoietin). Urine is formed as a result of a complex process starting with the filtration of plasma water from blood into the glomerulus. The walls of the glomerulus are freely permeable to water and small molecules but almost impermeable to proteins and large molecules. Thus, in a healthy kidney, the filtrate is virtually free of protein and has no cellular elements. The filtered fluid that eventually becomes urine flows through the tubules. The final chemical composition of the urine is determined by the secretion into, and re-absorption of substances from, the urine required to maintain homeostasis.

Receiving about 20% of cardiac output, the two kidneys filter about 125 ml of plasma water per minute. Filtration occurs because of a pressure gradient across the glomerular membrane. The pressure in the arteries of the kidney pushes plasma water into the glomerulus causing filtration. To keep the Glomerulur Filtration Rate ("GFR") relatively constant, pressure in the glomerulus is held constant by the constriction or dilatation of the afferent and efferent arterioles, the muscular walled vessels leading to and from each glomerulus.

In a CHF patient, the heart will progressively fail, and blood flow and pressure will drop in the patient's circulatory system. During acute heart failure, short-term compensations serve to maintain perfusion to critical organs, notably the brain and the heart that cannot survive prolonged reduction in blood flow. However, these same responses that initially aid survival during acute heart failure become deleterious during chronic heart failure.

A combination of complex mechanisms contribute to deleterious fluid overload in CHF. As the heart fails and blood pressure drops, the kidneys cannot function and become impaired due to insufficient blood pressure for perfusion. This impairment in renal function ultimately leads to the decrease in urine output. Without sufficient urine output, the body retains fluids, and the resulting fluid overload causes peripheral edema (swelling of the legs), shortness of breath (due to fluid in the lungs), and fluid retention in the abdomen, among other undesirable conditions in the patient.

In addition, the decrease in cardiac output leads to reduced renal blood flow, increased neurohormonal stimulus, and release of the hormone renin from the juxtaglomerular apparatus of the kidney. This results in avid retention of sodium and, thus, volume expansion. Increased renin results in the formation of angiotensin, a potent vasoconstrictor. Heart failure and the resulting reduction in blood pressure also reduce the blood flow and perfusion pressure through organs in the body other than the kidneys. As they suffer reduced blood pressure, these organs may become hypoxic, resulting in a metabolic acidosis that reduces the effectiveness of pharmacological therapy and increases a risk of sudden death.

This spiral of deterioration that physicians observe in heart failure patients is believed to be mediated, at least in part, by activation of a subtle interaction between heart function and kidney function, known as the renin-angiotensin system. Disturbances in the heart's pumping function results in decreased cardiac output and diminished blood flow. The kidneys respond to the diminished blood flow as though the total blood volume was decreased, when in fact the measured volume is normal or even increased. This leads to fluid retention by the kidneys and formation of edema, thereby causing the fluid overload and increased stress on the heart.

Systemically, CHF is associated with an abnormally elevated peripheral vascular resistance and is dominated by alterations of the circulation resulting from an intense disturbance of sympathetic nervous system function. Increased activity of the sympathetic nervous system promotes a downward vicious cycle of increased arterial vasoconstriction (increased resistance of vessels to blood flow) followed by a further reduction of cardiac output, causing even more diminished blood flow to the vital organs.

In CHF via the previously explained mechanism of vasoconstriction, the heart and circulatory system dramatically reduce blood flow to the kidneys. During CHF, the kidneys receive a command from higher neural centers via neural pathways and hormonal messengers to retain fluid and sodium in the body. In response to stress on the heart, the neural centers command the kidneys to reduce their filtering functions. While in the short term, these commands can be beneficial, if these commands continue over hours and days they can jeopardize the person's life or make the person dependent on artificial kidney for life by causing the kidneys to cease functioning.

When the kidneys do not fully filter the blood, a huge amount of fluid is retained in the body, which results in bloating (fluid retention in tissues) and increases the workload of the heart. Fluid can penetrate into the lungs, and the patient becomes short of breath. This odd and self-destructive phenomenon is most likely explained by the effects of normal compensatory mechanisms of the body that improperly perceive the chronically low blood pressure of CHF as a sign of temporary disturbance, such as bleeding.

In an acute situation, the body tries to protect its most vital organs, the brain and the heart, from the hazards of oxygen deprivation. Commands are issued via neural and hormonal pathways and messengers. These commands are directed toward the goal of maintaining blood pressure to the brain and heart, which are treated by the body as the most vital organs. The brain and heart cannot sustain low perfusion for any substantial period of time. A stroke or a cardiac arrest will result if the blood pressure to these organs is reduced to unacceptable levels. Other organs, such as the kidneys, can withstand somewhat longer periods of ischemia without suffering long-term damage. Accordingly, the body sacrifices blood supply to these other organs in favor of the brain and the heart.

The hemodynamic impairment resulting from CHF activates several neurohormonal systems, such as the renin-angiotensin and aldosterone system, sympatho-adrenal system and vasopressin release. As the kidneys suffer from increased renal vasoconstriction, the GFR drops, and the sodium load in the circulatory system increases. Simultaneously, more renin is liberated from the juxtaglomerular of the kidney. The combined effects of reduced kidney functioning include reduced glomerular sodium load, an aldosterone-mediated increase in tubular reabsorption of sodium, and retention in the body of sodium and water. These effects lead to several signs and symptoms of the CHF condition, including an enlarged heart, increased systolic wall stress, an increased myocardial oxygen demand, and the formation of edema on the basis of fluid and sodium retention in the kidney. Accordingly, sustained reduction in renal blood flow and vasoconstriction is directly responsible for causing the fluid retention associated with CHF.

CHF is progressive, and as of now, not curable. The limitations of drug therapy and its inability to reverse or even arrest the deterioration of CHF patients are clear. Surgical therapies are effective in some cases, but limited to the end-stage patient population because of the associated risk and cost. Furthermore, the dramatic role played by kidneys in the deterioration of CHF patients is not adequately addressed by current surgical therapies.

The autonomic nervous system is recognized as an important pathway for control signals that are responsible for the regulation of body functions critical for maintaining vascular fluid balance and blood pressure. The autonomic nervous system conducts information in the form of signals from the body's biologic sensors such as baroreceptors (responding to pressure and volume of blood) and chemoreceptors (responding to chemical composition of blood) to the central nervous system via its sensory fibers. It also conducts command signals from the central nervous system that control the various innervated components of the vascular system via its motor fibers.

Experience with human kidney transplantation provided early evidence of the role of the nervous system in kidney function. It was noted that after transplant, when all the kidney nerves were totally severed, the kidney increased the excretion of water and sodium. This phenomenon was also observed in animals when the renal nerves were cut or chemically destroyed. The phenomenon was called "denervation diuresis" since the denervation acted on a kidney similar to a diuretic medication. Later the "denervation diuresis" was found to be associated with vasodilatation of the renal arterial system that led to increased blood flow through the kidney.

This observation was confirmed by the observation in animals that reducing blood pressure supplying the kidneys reversed the "denervation diuresis".

It was also observed that after several months passed after the transplant surgery in successful cases, the "denervation diuresis" in transplant recipients stopped and the kidney function returned to normal. Originally, it was believed that the "renal diuresis" was a transient phenomenon and that the nerves conducting signals from the central nervous system to the kidney were not essential to kidney function. Later discoveries suggested that the renal nerves had a profound ability to regenerate and that the reversal of "denervation diuresis" could be attributed to the growth of new nerve fibers supplying the kidneys with necessary stimuli.

Another body of research focused on the role of the neural control of secretion of the hormone renin by the kidney. As was discussed previously, renin is a hormone responsible for the "vicious cycle" of vasoconstriction and water and sodium retention in heart failure patients. It was demonstrated that an increase or decrease in renal sympathetic nerve activity produced parallel increases and decreases in the renin secretion rate by the kidney, respectively.

In summary, it is known from clinical experience and the large body of animal research that an increase in renal sympathetic nerve activity leads to vasoconstriction of blood vessels supplying the kidney, decreased renal blood flow, decreased removal of water and sodium from the body, and increased renin secretion. It is also known that reduction of sympathetic renal nerve activity, e.g., via denervation, may reverse these processes.

It has been established in animal models that the heart failure condition results in abnormally high sympathetic stimulation of the kidney. This phenomenon was traced back to the sensory nerves conducting signals from baroreceptors to the central nervous system. Baroreceptors are present in the different locations of the vascular system. Powerful relationships exist between baroreceptors in the carotid arteries (supplying the brain with arterial blood) and sympathetic nervous stimulus to the kidneys. When arterial blood pressure was suddenly reduced in experimental animals with heart failure, sympathetic tone increased. Nevertheless, the normal baroreflex likely is not solely responsible for elevated renal nerve activity in chronic CHF patients. If exposed to a reduced level of arterial pressure for a prolonged time, baroreceptors normally "reset", i.e., return to a baseline level of activity, until a new disturbance is introduced. Therefore, it is believed that in chronic CHF patients, the components of the autonomic-nervous system responsible for the control of blood pressure and the neural control of the kidney function become abnormal. The exact mechanisms that cause this abnormality are not fully understood, but its effects on the overall condition of the CHF patients are profoundly negative.

End-Stage Renal Disease is another condition at least partially controlled by renal neural activity. There has been a dramatic increase in patients with ESRD due to diabetic nephropathy, chronic glomerulonephritis and uncontrolled hypertension. Chronic Renal Failure slowly progresses to ESRD. CRF represents a critical period in the evolution of ESRD. The signs and symptoms of CRF are initially minor, but over the course of 2-5 years, become progressive and irreversible. While some progress has been made in combating the progression to, and complications of, ESRD, the clinical benefits of existing interventions remain limited.

It has been known for several decades that renal diseases of diverse etiology (hypotension, infection, trauma, autoimmune disease, etc.) can lead to the syndrome of CRF characterized by systemic hypertension, proteinuria (excess protein filtered from the blood into the urine) and a progressive decline in GFR ultimately resulting in ESRD. These observations suggest that CRF progresses via a common pathway of mechanisms and that therapeutic interventions inhibiting this common pathway may be successful in slowing the rate of progression of CRF irrespective of the initiating cause.

To start the vicious cycle of CRF, an initial insult to the kidney causes loss of some nephrons. To maintain normal GFR, there is an activation of compensatory renal and systemic mechanisms resulting in a state of hyperfiltration in the remaining nephrons. Eventually, however, the increasing numbers of nephrons "overworked" and damaged by hyperfiltration are lost. At some point, a sufficient number of nephrons are lost so that normal GFR can no longer be maintained. These pathologic changes of CRF produce worsening systemic hypertension, thus high glomerular pressure and increased hyperfiltration. Increased glomerular hyperfiltration and permeability in CRF pushes an increased amount of protein from the blood, across the glomerulus and into the renal tubules. This protein is directly toxic to the tubules and leads to further loss of nephrons, increasing the rate of progression of CRF. This vicious cycle of CRF continues as the GFR drops with loss of additional nephrons leading to further hyperfiltration and eventually to ESRD requiring dialysis. Clinically, hypertension and excess protein filtration have been shown to be two major determining factors in the rate of progression of CRF to ESRD.

Though previously clinically known, it was not until the 1980s that the physiologic link between hypertension, proteinuria, nephron loss and CRF was identified. In 1990s the role of sympathetic nervous system activity was elucidated. Afferent signals arising from the damaged kidneys due to the activation of mechanoreceptors and chemoreceptors stimulate areas of the brain responsible for blood pressure control. In response, the brain increases sympathetic stimulation on the systemic level, resulting in increased blood pressure primarily through vasoconstriction of blood vessels. When elevated sympathetic stimulation reaches the kidney via the efferent sympathetic nerve fibers, it produces major deleterious effects in two forms. The kidneys are damaged by direct renal toxicity from the release of sympathetic neurotransmitters (such as norepinephrine) in the kidneys independent of the hypertension. Furthermore, secretion of renin that activates Angiotensin II is increased, which increases systemic vasoconstriction and exacerbates hypertension.

Over time, damage to the kidneys leads to a further increase of afferent sympathetic signals from the kidney to the brain. Elevated Angiotensin II further facilitates internal renal release of neurotransmitters. The feedback loop is therefore closed, which accelerates deterioration of the kidneys.

In view of the foregoing, it would be desirable to provide methods and apparatus for the treatment of congestive heart failure, renal disease, hypertension and/or other cardio-renal diseases via renal neuromodulation and/or denervation.

SUMMARY

The present invention provides methods and apparatus for renal neuromodulation (e.g., denervation) using a pulsed electric field (PEF). Several aspects of the invention apply a pulsed electric field to effectuate electroporation and/or electrofusion in renal nerves, other neural fibers that contribute to renal neural function, or other neural features. Several embodiments of the invention are intravascular devices for inducing renal neuromodulation. The apparatus and methods described herein may utilize any suitable electrical signal or field parameters that achieve neuromodulation, including denervation, and/or otherwise create an electroporative and/or electrofusion effect. For example, the electrical signal may incorporate a nanosecond pulsed electric field (nsPEF) and/or a PEF for effectuating electroporation. One specific embodiment comprises applying a first course of PEF electroporation followed by a second course of nsPEF electroporation to induce apoptosis in any cells left intact after the PEF treatment, or vice versa. An alternative embodiment comprises fusing nerve cells by applying a PEF in a manner that is expected to reduce or eliminate the ability of the nerves to conduct electrical impulses. When the methods and apparatus are applied to renal nerves and/or other neural fibers that contribute to renal neural functions, this present inventors believe that urine output will increase and/or blood pressure will be controlled in a manner that will prevent or treat CHF, hypertension, renal system diseases, and other renal anomalies.

Several aspects of particular embodiments can achieve such results by selecting suitable parameters for the PEFs and/or nsPEFs. Pulsed electric field parameters can include, but are not limited to, field strength, pulse width, the shape of the pulse, the number of pulses and/or the interval between pulses (e.g., duty cycle). Suitable field strengths include, for example, strengths of up to about 10,000 V/cm. Suitable pulse widths include, for example, widths of up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, combinations thereof, etc. Suitable numbers of pulses include, for example, at least one pulse. Suitable pulse intervals include, for example, intervals less than about 10 seconds. Any combination of these parameters may be utilized as desired. These parameters are provided for the sake of illustration and should in no way be considered limiting. Additional and alternative waveform parameters will be apparent.

Several embodiments are directed to percutaneous intravascular systems for providing long-lasting denervation to minimize acute myocardial infarct ("AMI") expansion and for helping to prevent the onset of morphological changes that are affiliated with congestive heart failure. For example, one embodiment of the invention comprises treating a patient for an infarction, e.g., via coronary angioplasty and/or stenting, and performing an intra-arterial pulsed electric field renal denervation procedure under fluoroscopic guidance. Alternatively, PEF therapy could be delivered in a separate session soon after the AMI had been stabilized. Renal neuromodulation also may be used as an adjunctive therapy to renal surgical procedures. In these embodiments, the anticipated increase in urine output and/or control of blood pressure provided by the renal PEF therapy is expected to reduce the load on the heart to inhibit expansion of the infarct and prevent CHF.

Several embodiments of intravascular pulsed electric field systems described herein may denervate or reduce the activity of the renal nervous supply immediately post-infarct, or at any time thereafter, without leaving behind a permanent implant in the patient. These embodiments are expected to increase urine output and/or control blood pressure for a period of several months during which the patient's heart can heal. If it is determined that repeat and/or chronic neuromodulation would be beneficial after this period of healing, renal PEF treatment can be repeated as needed.

In addition to efficaciously treating AMI, several embodiments of systems described herein are also expected to treat CHF, hypertension, renal failure, and other renal or cardiorenal diseases influenced or affected by increased renal sympathetic nervous activity. For example, the systems may be used to treat CHF at any time by advancing the PEF system to a treatment site via a vascular structure and then delivering a PEF therapy to the treatment site. This may, for example, modify a level of fluid offload.

Embodiments of intravascular PEF systems described herein may be used similarly to angioplasty or electrophysiology catheters which are well known in the art. For example, arterial access may be gained through a standard Seldinger Technique, and an arterial sheath optionally may be placed to provide catheter access. A guidewire may be advanced through the vasculature and into the renal artery of the patient, and then an intravascular PEF may be advanced over the guidewire and/or through the sheath into the renal artery. The sheath optionally may be placed before inserting the PEF catheter or advanced along with the PEF catheter such that the sheath partially or completely covers the catheter. Alternatively, the PEF catheter may be advanced directly through the vasculature without the use of a guide wire and/or introduced and advanced into the vasculature without a sheath.

In addition to arterial placement, the PEF system may be placed within a vein. Venous access may, for example, be achieved via a jugular approach. PEF systems may be utilized, for example, within the renal artery, within the renal vein or within both the renal artery and the renal vein to facilitate more complete denervation.

After the PEF catheter is positioned within the vessel at a desired location with respect to the target neurons, it is stabilized within the vessel (e.g., braced against the vessel wall) and energy is delivered to the target nerve or neurons. In one variation, pulsed RF energy is delivered to the target to create a non-thermal nerve block, reduce neural signaling, or otherwise modulate neural activity. Alternatively or additionally, cooling, cryogenic, thermal RF, thermal or non-thermal microwave, focused or unfocused ultrasound, thermal or non-thermal DC, as well as any combination thereof, may be employed to reduce or otherwise control neural signaling.

In still other embodiments of the invention, other non-renal neural structures may be targeted from within arterial or venous conduits in addition to or in lieu of renal neural structures. For instance, a PEF catheter can be navigated through the aorta or the vena cava and brought into apposition with various neural structures to treat other conditions or augment the treatment of renal-cardiac conditions. For example, nerve bodies of the lumbar sympathetic chain may be accessed and modulated, blocked or ablated, etc., in this manner.

Several embodiments of the PEF systems may completely block or denervate the target neural structures, or the PEF systems may otherwise modulate the renal nervous activity. As opposed to a full neural blockade such as denervation, other neuromodulation produces a less-than-complete change in the level of renal nervous activity between the kidney(s) and the rest of the body. Accordingly, varying the pulsed electric field parameters will produce different effects on the nervous activity.

In one embodiment of an intravascular pulsed electric field system, the device includes one or more electrodes that are configured to physically contact a target region of a renal vasculature for delivery of a pulsed electric field. For example, the device can comprise a catheter having an expandable helical section and one or more electrodes at the helical section. The catheter may be positioned in the renal vasculature while in a low profile configuration. The expandable section can then be expanded to contact the inner surface of the vessel wall. Alternatively, the catheter can have one or more expandable helical electrodes. For example, first and second expandable electrodes may be positioned within the vessel at a desired distance from one another to provide an active electrode and a return electrode. The expandable electrodes may comprise shape-memory materials, inflatable balloons, expandable meshes, linkage systems and other types of devices that can expand in a controlled manner. Suitable expandable linkage systems include expandable baskets, having a plurality of shape-memory wires or slotted hypotubes, and/or expandable rings. Additionally, the expandable electrodes may be point contact electrodes arranged along a balloon portion of a catheter.

Other embodiments of pulsed electric field systems include electrodes that do not physically contact the vessel wall. RF energy, both traditional thermal energy and relatively non-thermal pulsed RF, are examples of pulsed electric fields that can be conducted into tissue to be treated from a short distance away from the tissue itself. Other types of pulsed electric fields can also be used in situations in which the electrodes do not physically contact the vessel wall. As such, the pulsed electric fields can be applied directly to the nerve via physical contact between the electrode contacts and the vessel wall or other tissue, or the pulsed electric fields can be applied indirectly to the nerve without physically contacting the electrode contacts with the vessel wall. The term "nerve contact" accordingly includes physical contact of a system element with the nerve and/or tissue proximate to the nerve, and also electrical contact alone without physically contacting the nerve or tissue. To indirectly apply the pulsed electrical field, the device has a centering element configured to position the electrodes in a central region of the vessel or otherwise space the electrodes apart from the vessel wall. The centering element may comprise, for example, a balloon or an expandable basket. One or more electrodes may be positioned on a central shaft of the centering element—either longitudinally aligned with the element or positioned on either side of the element. When utilizing a balloon catheter, the inflated balloon may act as an insulator of increased impedance for orienting or directing a pulsed electric field along a desired electric flow path. As will be apparent, alternative insulators may be utilized.

In another embodiment of the system, a combination apparatus includes an intravascular catheter having a first electrode configured to physically contact the vessel wall and a second electrode configured to be positioned within the vessel but spaced apart from the vessel wall. For example, an expandable helical electrode may be used in combination with a centrally-disposed electrode to provide such a bipolar electrode pair.

In yet another embodiment, a radial position of one or more electrodes relative to a vessel wall may be altered dynamically to focus the pulsed electric field delivered by the electrode(s). In still another variation, the electrodes may be configured for partial or complete passage across the vessel wall. For example, the electrode(s) may be positioned within the renal vein, then passed across the wall of the renal vein into the perivascular space such that they at least partially encircle the renal artery and/or vein prior to delivery of a pulsed electric field.

Bipolar embodiments of the present invention may be configured for dynamic movement or operation relative to a spacing between the active and ground electrodes to achieve treatment over a desired distance, volume or other dimension. For example, a plurality of electrodes may be arranged such that a bipolar pair of electrodes can move longitudinally relative to each other for adjusting the separation distance between the electrodes and/or for altering the location of treatment. One specific embodiment includes a first electrode coupled to a catheter and a moveable second electrode that can move through a lumen of the catheter. In alternative embodiments, a first electrode can be attached to a catheter and a second electrode can be attached to an endoluminally-delivered device such that the first and second electrodes may be repositioned relative to one another to alter a separation distance between the electrodes. Such embodiments may facilitate treatment of a variety of renal vasculature anatomies.

Any of the embodiments of the present invention described herein optionally may be configured for infusing agents into the treatment area before, during or after energy application. The infused agents can be selected to enhance or modify the neuromodulatory effect of the energy application. The agents can also protect or temporarily displace non-target cells, and/or facilitate visualization.

Several embodiments of the present invention may comprise detectors or other elements that facilitate identification of locations for treatment and/or that measure or confirm the success of treatment. For example, the system can be configured to also deliver stimulation waveforms and monitor physiological parameters known to respond to stimulation of the renal nerves. Based on the results of the monitored parameters, the system can determine the location of renal nerves and/or whether denervation has occurred. Detectors for monitoring of such physiological responses include, for example, Doppler elements, thermocouples, pressure sensors, and imaging modalities (e.g., fluoroscopy, intravascular ultrasound, etc.). Alternatively, electroporation may be monitored directly using, for example, Electrical Impedance Tomography ("EIT") or other electrical impedance measurements. Additional monitoring techniques and elements will be apparent. Such detector(s) may be integrated with the PEF systems or they may be separate elements.

Still other specific embodiments include electrodes configured to align the electric field with the longer dimension of the target cells. For instance, nerve cells tend to be elongate structures with lengths that greatly exceed their lateral dimensions (e.g., diameter). By aligning an electric field so that the directionality of field propagation preferentially affects the longitudinal aspect of the cell rather than the lateral aspect of the cell, it is expected that lower field strengths can to be used to kill or disable target cells. This is expected to conserve the battery life of implantable devices, reduce collateral effects on adjacent structures, and otherwise enhance the ability to modulate the neural activity of target cells.

Other embodiments of the invention are directed to applications in which the longitudinal dimensions of cells in tissues overlying or underlying the nerve are transverse (e.g., orthogonal or otherwise at an angle) with respect to the longitudinal direction of the nerve cells. Another aspect of these embodiments is to align the directionality of the PEF such that the field aligns with the longer dimensions of the target cells and the shorter dimensions of the non-target cells. More specifically, arterial smooth muscle cells are typically elongate cells which surround the arterial circumference in a generally spiraling orientation so that their longer dimensions are circumferential rather than running longitudinally along the artery. Nerves of the renal plexus, on the other hand, run along the outside of the artery generally in the longitudinal direction of the artery. Therefore, applying a PEF which is generally aligned with the longitudinal direction of the artery is expected to preferentially cause electroporation in the target nerve cells without affecting at least some of the non-target arterial smooth muscle cells to the same degree. This may enable preferential denervation of nerve cells (target cells) in the adventitia or periarterial region from an intravascular device without affecting the smooth muscle cells of the vessel to an undesirable extent.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which:

FIG. 2 is a schematic detail view showing the location of the renal nerves relative to the renal artery.

FIGS. 3A and 3B are schematic side- and end-views, respectively, illustrating a direction of electrical current flow for selectively affecting renal nerves.

FIG. 4 is a schematic side-view, partially in section, of an intravascular catheter having a plurality of electrodes in accordance with one embodiment of the invention.

FIG. 5 is a schematic side-view, partially in section, of an intravascular device having a pair of expanding helical electrodes arranged at a desired distance from one another in accordance with another embodiment of the invention.

FIG. 6 is a schematic side-view, partially in section, of an intravascular device having a first electrode on an expandable balloon, and a second electrode on a catheter shaft in accordance with another embodiment of the invention.

FIG. 7 is a schematic side-view, partially in section, of an intravascular device having an expanding first electrode delivered through the lumen of a catheter and a complementary second electrode carried by the catheter in accordance with another embodiment of the invention.

FIG. 8 is a schematic side-view, partially in section, of an intravascular device having an expandable basket and a plurality of electrodes at the basket in accordance with another embodiment of the invention.

FIG. 9 is a schematic detail view of the apparatus of FIG. 8 illustrating one embodiment of the electrodes in accordance with another embodiment of the invention.

FIG. 10 is a schematic side-view, partially in section, of an intravascular device having expandable ring electrodes for contacting the vessel wall and an optional insulation element in accordance with another embodiment of the invention.

FIGS. 11A-11C are schematic detail views of embodiments of different windings for the ring electrodes of FIG. 10.

FIG. 12 is a schematic side-view, partially in section, of an intravascular device having ring electrodes of FIG. 10 with the windings shown in FIGS. 11A-11C.

FIG. 13 is a schematic side-view, partially in section, of an intravascular device having a ring electrode and a luminally-delivered electrode in accordance with another embodiment of the invention.

FIG. 14 is a schematic side-view, partially in section, of an intravascular device having a balloon catheter and expandable point contact electrodes arranged proximally and distally of the balloon in accordance with another embodiment of the invention.

FIG. 15 is a schematic side-view of an intravascular device having a balloon catheter and electrodes arranged proximally and distally of the balloon in accordance with another embodiment of the invention.

FIGS. 16A and 16B are schematic side-views, partially in section, illustrating stages of a method of using the apparatus of FIG. 15 in accordance with an embodiment of the invention.

FIG. 17 is a schematic side-view of an intravascular device having a balloon catheter and a plurality of dynamically operable electrodes in accordance with another embodiment of the invention.

FIG. 18 is a schematic side-view of an intravascular device having a distal electrode deployed through a lumen of the balloon catheter in accordance with another embodiment of the invention.

FIGS. 19A and 19B are side-views, partially in section, illustrating methods of using the intravascular device shown in FIG. 18 to modulate renal neural activity in patients with various renal vasculatures.

FIG. 20 is a side view, partially in section, illustrating an intravascular device having a plurality of electrodes arranged along the shaft of, and in line with, a centering element in accordance with another embodiment of the invention.

FIG. 21 is a side-view, partially in section, illustrating an intravascular device having electrodes configured for dynamic radial repositioning to facilitate focusing of a pulsed electric field in accordance with another embodiment of the invention.

FIG. 22 is a side-view, partially in section, of an intravascular device having an infusion/aspiration catheter in accordance with another embodiment of the invention.

FIGS. 23A-23C are, respectively, a side-view, partially in section, and cross-sectional views along section line A-A of FIG. 23A, illustrating a method of using an intravascular device in accordance with an embodiment of the invention configured for passage of electrode(s) at least partially across the vessel wall.

FIGS. 24A and 24B are side-views, partially in section, illustrating an intravascular device having detectors for measuring or monitoring treatment efficacy in accordance with another embodiment of the invention.

DETAILED DESCRIPTION

A. Overview

Figure 1:
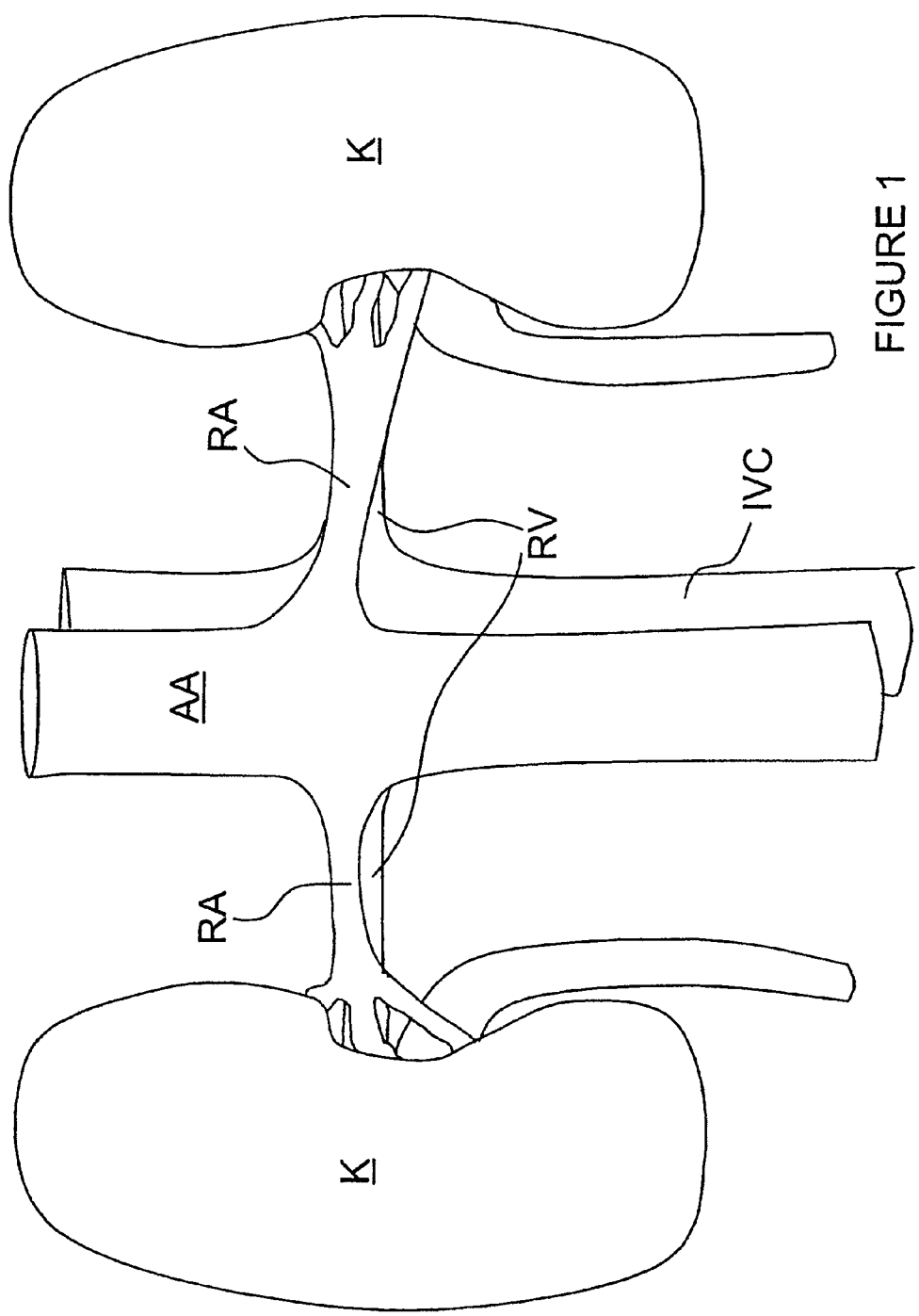
FIG. 1 is a schematic view illustrating human renal anatomy.

The present invention relates to methods and apparatus for renal neuromodulation and/or other neuromodulation. More particularly, the present invention relates to methods and apparatus for renal neuromodulation using a pulsed electric field to effectuate electroporation or electrofusion. As used herein, electroporation and electropermeabilization are methods of manipulating the cell membrane or intracellular apparatus. For example, short high-energy pulses cause pores to open in cell membranes. The extent of porosity in the cell membrane (e.g., size and number of pores) and the duration of the pores (e.g., temporary or permanent) are a function of the field strength, pulse width, duty cycle, field orientation, cell type and other parameters. In general, pores will generally close spontaneously upon termination of lower strength fields or shorter pulse widths (herein defined as "reversible electroporation"). Each cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes. Certain types of electroporation energy parameters also appropriate for use in renal neuromodulation are high voltage pulses with a duration in the sub-microsecond range (nanosecond pulsed electric fields, or nsPEF) which may leave the cellular membrane intact, but alter the intracellular apparatus or function of the cell in ways which cause cell death or disruption. Certain applications of nsPEF have been shown to cause cell death by inducing apoptosis, or programmed cell death, rather than acute cell death. Also, the term "comprising" is used throughout to mean including at least the recited feature such that any greater number of the same feature and/or additional types features are not precluded.

Several embodiments of the present invention provide intravascular devices for inducing renal neuromodulation, such as a temporary change in target nerves that dissipates over time, continuous control over neural function, and/or denervation. The apparatus and methods described herein may utilize any suitable electrical signal or field parameters, e.g., any electric field, that will achieve the desired neuromodulation (e.g., electroporative effect). To better understand the structures of the intravascular devices and the methods of using these devices for neuromodulation, it is useful to understand the renal anatomy in humans.

B. Selected Embodiments of Methods for Neuromodulation

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference spiral around the angular axis θ of the artery, i.e., around the circumference of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Referring to FIGS. 3A and 3B, the cellular misalignment of the renal nerves and the smooth muscle cells may be exploited to selectively affect renal nerve cells with reduced effect on smooth muscle cells. More specifically, because larger cells require less energy to exceed the irreversibility threshold of electroporation, several embodiments of electrodes of the present invention are configured to align at least a portion of an electric field generated by the electrodes with or near the longer dimensions of the cells to be affected. In specific embodiments, the intravascular device has electrodes configured to create an electrical field aligned with or near the lengthwise dimension of the renal artery RA to affect renal nerves RN. By aligning an electric field so that the field preferentially affects the lengthwise aspect of the cell rather than the diametric or radial aspect of the cell, lower field strengths may be used to necrose cells. As mentioned above, this is expected to reduce power consumption and mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning the PEF with the lengthwise or longer dimensions of the target cells, the PEF may propagate along the lateral or shorter dimensions of the non-target cells (i.e. such that the PEF propagates at least partially out of alignment with non-target smooth muscle cells SMC). Therefore, as seen in FIGS. 3A and 3B, applying a PEF with propagation lines Li generally aligned with the longitudinal dimension L of the renal artery RA is expected to preferentially cause electroporation, electrofusion, denervation or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

Embodiments of the method shown in FIGS. 3A and 3B may have particular application with the intravascular methods and apparatus of the present invention. For instance, a PEF catheter placed within the renal artery may propagate an electric field having a longitudinal portion that is aligned to run with the longitudinal dimension of the artery in the region of the renal nerves RN and the smooth muscle cell SMC of the vessel wall so that the wall of the artery remains at least substantially intact while the outer nerve cells are destroyed.

C. Embodiments of Systems and Additional Methods for Neuromodulation

FIG. 4 shows one embodiment of an intravascular pulsed electric field apparatus 200 in accordance with the present invention that includes one or more electrodes configured to physically contact a target region within the renal vasculature and deliver a pulsed electric field across a wall of the vasculature. The apparatus 200 is shown within a patient's renal artery RA, but it can be positioned in other intravascular locations (e.g., the renal vein). This embodiment of the apparatus 200 comprises an intravascular catheter 210 having a proximal section 211a, a distal section 211b, and a plurality of distal electrodes 212 at the distal section 211b. The proximal section 211a generally has an electrical connector to couple the catheter 210 to a pulse generator, and the distal section 211b in this embodiment has a helical configuration. The apparatus 200 is electrically coupled to a pulsed electric field generator 100 located proximal and external to the patient; the electrodes 212 are electrically coupled to the generator via catheter 210. The generator 100 may be utilized with any embodiment of the present invention described hereinafter for delivery of a PEF with desired field parameters. It should be understood that electrodes of embodiments described hereinafter may be connected to the generator, even if the generator is not explicitly shown or described with each variation.

The helical distal section 211b of catheter 210 is configured to appose the vessel wall and bring electrodes 212 into close proximity to extra-vascular neural structures. The pitch of the helix can be varied to provide a longer treatment zone, or to minimize circumferential overlap of adjacent treatments zones in order to reduce a risk of stenosis formation. This pitch change can be achieved by combining a plurality of catheters of different pitches to form catheter 210, or by adjusting the pitch of catheter 210 through the use of internal pull wires, adjusting mandrels inserted into the catheter, shaping sheaths placed over the catheter, or by any other suitable means for changing the pitch either in-situ or before introduction into the body.

The electrodes 212 along the length of the pitch can be individual electrodes, a common but segmented electrode, or a common and continuous electrode. A common and continuous electrode may, for example, comprise a conductive coil formed into or placed over the helical portion of catheter 210. A common but segmented electrode may, for example, be formed by providing a slotted tube fitted onto or into the helical portion of the catheter, or by electrically connecting a series of individual electrodes.

Individual electrodes or groups of electrodes 212 may be configured to provide a bipolar signal, or all or a subset of the electrodes may be used together in conjunction with a separate external patient ground for monopolar use (the ground pad may, for example, be placed on the patient's leg). Electrodes 212 may be dynamically assignable to facilitate monopolar and/or bipolar energy delivery between any of the electrodes and/or between any of the electrodes and an external ground.

Catheter 210 may be delivered to renal artery RA in a low profile delivery configuration within sheath 150. Once positioned within the artery, the catheter may self-expand or may be expanded actively, e.g., via a pull wire or a balloon, into contact with an interior wall of the artery. A pulsed electric field then may be generated by the PEF generator 100, transferred through catheter 210 to electrodes 212, and delivered via the electrodes 212 across the wall of the artery. In many applications, the electrodes are arranged so that the pulsed electric field is aligned with the longitudinal dimension of the artery to modulate the neural activity along the renal nerves (e.g., denervation). This may be achieved, for example, via irreversible electroporation, electrofusion and/or inducement of apoptosis in the nerve cells.

FIG. 5 illustrates an apparatus 220 for neural modulation in accordance with another embodiment of the invention. The apparatus 220 includes a pair of catheters 222a and 222b having expandable distal sections 223a and 223b with helical electrodes 224a and 224b, respectively. The helical electrodes 224a and 224b are spaced apart from each other by a desired distance within a patient's renal vasculature. Electrodes 224a-b may be actuated in a bipolar fashion such that one electrode is an active electrode and the other is a return electrode. The distance between the electrodes may be altered as desired to change the field strength and/or the length of nerve segment modulated by the electrodes. The expandable helical electrodes may comprise shape-memory properties that facilitate self-expansion, e.g., after passage through sheath 150, or the electrodes may be actively expanded into contact with the vessel wall, e.g., via an inflatable balloon or via pull wires, etc. The catheters 222a-b preferably are electrically insulated in areas other than the distal helices of electrodes 224a-b.

FIG. 6 illustrates an apparatus 230 comprising a balloon catheter 232 having expandable balloon 234, a helical electrode 236 arranged about the balloon 234, and a shaft electrode 238 on the shaft of catheter 232. The shaft electrode 238 can be located proximal of expandable balloon 234 as shown, or the shaft electrode 238 can be located distal of the expandable balloon 234.

When the apparatus 230 is delivered to a target vessel, e.g., within renal artery RA, the expandable balloon 234 and the helical electrode 236 are arranged in a low profile delivery configuration. As seen in FIG. 6, once the apparatus has been positioned as desired, expandable balloon 234 may be inflated to drive the helical electrode 236 into physical contact with the wall of the vessel. In this embodiment, the shaft electrode 238 does not physically contact the vessel wall.

It is well known in the art of both traditional thermal RF energy delivery and of relatively non-thermal pulsed RF energy delivery that energy may be conducted to tissue to be treated from a short distance away from the tissue itself. Thus, it may be appreciated that "nerve contact" comprises both physical contact of a system element with a nerve, as well as electrical contact alone without physical contact, or a combination of the two. A centering element optionally may be provided to place electrodes in a central region of the vessel. The centering element may comprise, for example, an expandable balloon, such as balloon 234 of apparatus 230, or an expandable basket as described hereinafter. One or more electrodes may be positioned on a central shaft of the centering element—either longitudinally aligned with the element or positioned on one or both sides of the element—as is shaft electrode 238 of apparatus 230. When utilizing a balloon catheter such as catheter 232, the inflated balloon may act as an insulator of increased impedance for directing a pulsed electric field along a desired electric flow path. As will be apparent, alternative insulators may be utilized.

As seen in FIG. 6, when the helical electrode 236 physically contacts the wall of renal artery RA, the generator 100 may generate a PEF such that current passes between the helical electrode 236 and the shaft electrode 238 in a bipolar fashion. The PEF travels between the electrodes along lines Li that generally extend along the longitudinal dimension of the artery. The balloon 234 locally insulates and/or increases the impedance within the patient's vessel such that the PEF travels through the wall of the vessel between the helical and shaft electrodes. This focuses the energy to enhance denervation and/or other neuromodulation of the patient's renal nerves, e.g., via irreversible electroporation.

FIG. 7 illustrates an apparatus 240 similar to those shown in FIGS. 4-6 in accordance with another embodiment of the invention. The apparatus 240 comprises a balloon catheter 242 having an expandable balloon 244 and a shaft electrode 246 located proximal of the expandable balloon 244. The apparatus 240 further comprises an expandable helical electrode 248 configured for delivery through a guidewire lumen 243 of the catheter 242. The helical electrode 248 shown in FIG. 7 is self-expanding.

As seen in FIG. 7, after positioning the catheter 242 in a target vessel (e.g. renal artery RA), the balloon 244 is inflated until it contacts the wall of the vessel to hold the shaft electrode 246 at a desired location within the vessel and to insulate or increase the impedance of the interior of the vessel. The balloon 244 is generally configured to also center the shaft electrode 246 within the vessel or otherwise space the shaft electrode apart from the vessel wall by a desired distance. After inflating the balloon 244, the helical electrode 248 is pushed through lumen 243 until the helical electrode 248 extends beyond the catheter shaft; the electrode 248 then expands or otherwise moves into the helical configuration to physically contact the vessel wall. A bipolar pulsed electric field may then be delivered between the helical electrode 248 and the shaft electrode 246 along lines Li. For example, the helical electrode 248 may comprise the active electrode and the shaft electrode 246 may comprise the return electrode, or vice versa.

With reference now to FIG. 8, apparatus comprising an expandable basket having a plurality of electrodes that may be expanded into contact with the vessel wall is described. Apparatus 250 comprises catheter 252 having expandable distal basket 254 formed from a plurality of circumferential struts or members. A plurality of electrodes 256 are formed along the members of basket 254. Each member of the basket illustratively comprises a bipolar electrode pair configured to contact a wall of renal artery RA or another desired blood vessel.

Basket 254 may be fabricated, for example, from a plurality of shape-memory wires or ribbons, such as Nitinol, spring steel or elgiloy wires or ribbons, that form basket members 253. When the basket members comprise ribbons, the ribbons may be moved such that a surface area contacting the vessel wall is increased. Basket members 253 are coupled to catheter 252 at proximal and distal connections 255a and 255b, respectively. In such a configuration, the basket may be collapsed for delivery within sheath 150, and may self-expand into contact with the wall of the artery upon removal from the sheath. Proximal and/or distal connection 255a and 255b optionally may be configured to translate along the shaft of catheter 252 for a specified or unspecified distance in order to facilitate expansion and collapse of the basket.

Basket 254 alternatively may be formed from a slotted and/or laser-cut hypotube. In such a configuration, catheter 252 may, for example, comprise inner and outer shafts that are moveable relative to one another. Distal connection 255b of basket 254 may be coupled to the inner shaft and proximal connection 255a of the basket may be coupled to the outer shaft. Basket 254 may be expanded from a collapsed delivery configuration to the deployed configuration of FIG. 8 by approximating the inner and outer shafts of catheter 252, thereby approximating the proximal and distal connections 255a and 255b of the basket and expanding the basket. Likewise, the basket may be collapsed by separating the inner and outer shafts of the catheter.

As seen in FIG. 9, individual electrodes may be arranged along a basket strut or member 253. In one embodiment, the strut is formed from a conductive material coated with a dielectric material, and the electrodes 256 may be formed by removing regions of the dielectric coating. The insulation optionally may be removed only along a radially outer surface of the member such that electrodes 256 remain insulated on their radially interior surfaces; it is expected that this will direct the current flow outward into the vessel wall.

In addition, or as an alternative, to the fabrication technique of FIG. 9, the electrodes may be affixed to the inside surface, outside surface or embedded within the struts or members of basket 254. The electrodes placed along each strut or member may comprise individual electrodes, a common but segmented electrode, or a common and continuous electrode. Individual electrodes or groups of electrodes may be configured to provide a bipolar signal, or all or a subset of the electrodes may be actuated together in conjunction with an external patient ground for monopolar use.

One advantage of having electrodes 256 contact the vessel wall as shown in the embodiment of FIG. 8 is that it may reduce the need for an insulating element, such as an expandable balloon, to achieve renal denervation or other neuromodulation. However, it should be understood that such an insulating element may be provided and, for example, expanded within the basket. Furthermore, having the electrodes contact the wall may provide improved field geometry, i.e., may provide an electric field more aligned with the longitudinal axis of the vessel. Such contacting electrodes also may facilitate stimulation of the renal nerves before, during or after neuromodulation to better position the catheter 252 before treatment or for monitoring the effectiveness of treatment.

In a variation of apparatus 250, electrodes 256 may be disposed along the central shaft of catheter 252, and basket 254 may simply center the electrodes within the vessel to facilitate more precise delivery of energy across the vessel wall. This configuration may be well suited to precise targeting of vascular or extra-vascular tissue, such as the renal nerves surrounding the renal artery. Correctly sizing the basket or other centering element to the artery provides a known distance between the centered electrodes and the arterial wall that may be utilized to direct and/or focus the electric field as desired. This configuration may be utilized in high-intensity focused ultrasound or microwave applications, but also may be adapted for use with any other energy modality as desired.

Referring now to FIG. 10, it is expected that electrodes forming a circumferential contact with the wall of the renal artery may provide for more complete renal denervation or renal neuromodulation. In FIG. 10, a variation of the present invention comprising ring electrodes is described. Apparatus 260 comprises catheter 262 having expandable ring electrodes 264a and 264b configured to contact the wall of the vessel. The electrodes may be attached to the shaft of catheter 262 via struts 266, and catheter 262 may be configured for delivery to renal artery RA through sheath 150 in a low profile configuration. Struts 266 may be self-expanding or may be actively or mechanically expanded. Catheter 262 comprises guidewire lumen 263 for advancement over a guidewire. Catheter 262 also comprises optional inflatable balloon 268 that may act as an insulating element of increased impedance for preferentially directing current flow that is traveling between electrodes 264a and 264b across the wall of the artery.

FIGS. 11A-11C illustrate various embodiments of windings for ring electrodes 264. As shown, the ring electrodes may, for example, be wound in a coil (FIG. 11A), a zigzag (FIG. 11B) or a serpentine configuration (FIG. 11C). The periodicity of the winding may be specified, as desired. Furthermore, the type of winding, the periodicity, etc., may vary along the circumference of the electrodes.

With reference to FIG. 12, a variation of apparatus 260 is described comprising ring electrodes 264a' and 264b' having a sinusoidal winding in one embodiment of the serpentine winding shown in FIG. 11C. Struts 266 illustratively are attached to apexes of the sinusoid. The winding of electrodes 264a' and 264b' may provide for greater contact area along the vessel wall than do electrodes 264a and 264b, while still facilitating sheathing of apparatus 260 within sheath 150 for delivery and retrieval.

FIG. 13 illustrates another variation of apparatus 260 comprising a proximal ring electrode 264a, and further comprising a distal electrode 270 delivered through guidewire lumen 263 of catheter 262. The distal electrode 270 is non-expanding and is centered within the vessel via catheter 262. The distal electrode 270 may be a standard guide wire which is connected to the pulsed electric field generator and used as an electrode. However, it should be understood that electrode 270 alternatively may be configured for expansion into contact with the vessel wall, e.g., may comprise a ring or helical electrode.

Delivering the distal electrode through the lumen of catheter 262 may reduce a delivery profile of apparatus 260 and/or may improve flexibility of the device. Furthermore, delivery of the distal electrode through the guidewire lumen may serve as a safety feature that ensures that the medical practitioner removes any guidewire disposed within lumen 263 prior to delivery of a PEF. It also allows for customization of treatment length, as well as for treatment in side branches, as described hereinafter.

Ring electrodes 264a and 264b and 264a' and 264b' optionally may be electrically insulated along their radially inner surfaces, while their radially outer surfaces that contact the vessel wall are exposed. This may reduce a risk of thrombus formation and also may improve or enhance the directionality of the electric field along the longitudinal axis of the vessel. This also may facilitate a reduction of field voltage necessary to disrupt neural fibers. Materials utilized to at least partially insulate the ring electrodes may comprise, for example, PTFE, ePTFE, FEP, chronoprene, silicone, urethane, Pebax, etc. With reference to FIG. 14, another variation of apparatus 260 is described, wherein the ring electrodes have been replaced with point electrodes 272 disposed at the ends of struts 266. The point electrodes may be collapsed with struts 266 for delivery through sheath 150 and may self-expand with the struts into contact with the vessel wall. In FIG. 14, catheter 262 illustratively comprises four point electrodes 272 on either side of balloon 268. However, it should be understood that any desired number of struts and point electrodes may be provided around the circumference of catheter 262.

In FIG. 14, apparatus 260 illustratively comprises four struts 266 and four point electrodes 272 on either side of balloon 268. By utilizing all of the distally disposed electrodes 272*b* as active electrodes and all proximal electrodes 272*a* as return electrodes, or vice versa, lines Li along which the electric field propagates may be aligned with the longitudinal axis of a vessel. A degree of line Li overlap along the rotational axis of the vessel may be specified by specifying the angular placement and density of point electrodes 272 about the circumference of the catheter, as well as by specifying parameters of the PEF.

With reference now to FIG. 15, another variation of an intravascular PEF catheter is described. Apparatus 280 comprises catheter 282 having optional inflatable balloon or centering element 284, shaft electrodes 286*a* and 286*b* disposed along the shaft of the catheter on either side of the balloon, as well as optional radiopaque markers 288 disposed along the shaft of the catheter, illustratively in line with the balloon. Balloon 284 serves as both a centering element for electrodes 286 and as an electrical insulator for directing the electric field, as described previously.

Apparatus 280 may be particularly well-suited for achieving precise targeting of desired arterial or extra-arterial tissue, since properly sizing balloon 284 to the target artery sets a known distance between centered electrodes 286 and the arterial wall that may be utilized when specifying parameters of the PEF. Electrodes 286 alternatively may be attached to balloon 284 rather than to the central shaft of catheter 282 such that they contact the wall of the artery. In such a variation, the electrodes may be affixed to the inside surface, outside surface or embedded within the wall of the balloon.

Electrodes 286 arranged along the length of catheter 282 can be individual electrodes, a common but segmented electrode, or a common and continuous electrode. Furthermore, electrodes 286 may be configured to provide a bipolar signal, or electrodes 286 may be used together or individually in conjunction with a separate patient ground for monopolar use.

Referring now to FIGS. 16A and 16B, a method of using apparatus 280 to achieve renal denervation is described. As seen in FIG. 16A, catheter 282 may be disposed at a desired location within renal artery RA, balloon or centering element 284 may be expanded to center electrodes 286*a* and 286*b* and to optionally provide electrical insulation, and a PEF may be delivered, e.g., in a bipolar fashion between the proximal and distal electrodes 286*a* and 286*b*. It is expected that the PEF will achieve renal denervation and/or neuromodulation along treatment zone one $T_1$. If it is desired to modulate neural activity in other parts of the renal artery, balloon 284 may be at least partially deflated, and the catheter may be positioned at a second desired treatment zone $T_2$, as in FIG. 16B. The medical practitioner optionally may utilize fluoroscopic imaging of radiopaque markers 288 to orient catheter 282 at desired locations for treatment. For example, the medical practitioner may use the markers to ensure a region of overlap O between treatment zones $T_1$ and $T_2$, as shown.

With reference to FIG. 17, a variation of apparatus 280 is described comprising a plurality of dynamically controllable electrodes 286*a* and 286*b* disposed on the proximal side of balloon 284. In one variation, any one of proximal electrodes 286*a* may be energized in a bipolar fashion with distal electrode 286*b* to provide dynamic control of the longitudinal distance between the active and return electrodes. This alters the size and shape of the zone of treatment. In another variation, any subset of proximal electrodes 286*a* may be energized together as the active or return electrodes of a bipolar electric field established between the proximal electrodes and distal electrode 286*b*.

Although the apparatus 280 shown in FIG. 17 has three proximal electrodes $286a_1$, $286a_2$ and $286a_3$, it should be understood that the apparatus 280 can have any alternative number of proximal electrodes. Furthermore, the apparatus 280 can have a plurality of distal electrodes 286*b* in addition, or as an alternative, to multiple proximal electrodes. Additionally, one electrode of a pair may be coupled to the catheter 282, and the other electrode may be delivered through a lumen of the catheter, e.g., through a guidewire lumen. The catheter and endoluminally-delivered electrode may be repositioned relative to one another to alter a separation distance between the electrodes. Such a variation also may facilitate treatment of a variety of renal vasculature anatomies.

In the variations of apparatus 280 described thus far, distal electrode 286*b* is coupled to the shaft of catheter 282 distal of balloon 284. The distal electrode may utilize a lumen within catheter 282, e.g., for routing of a lead wire that acts as ground. Additionally, the portion of catheter 282 distal of balloon 284 is long enough to accommodate the distal electrode.

Catheters commonly are delivered over metallic and/or conductive guidewires. In many interventional therapies involving catheters, guidewires are not removed during treatment. As apparatus 280 is configured for delivery of a pulsed electric field, if the guidewire is not removed, there may be a risk of electric shock to anyone in contact with the guidewire during energy delivery. This risk may be reduced by using polymer-coated guidewires.

With reference to FIG. 18, another variation of apparatus 280 is described wherein distal electrode 286*b* of FIGS. 16 and 17 has been replaced with a distal electrode 270 configured to be moved through a lumen of the catheter as described previously with respect to FIG. 13. As will be apparent, proximal electrode 286*a* alternatively may be replaced with the luminally-delivered electrode, such that electrodes 286*b* and 270 form a bipolar electrode pair. Electrode 270 does not utilize an additional lumen within catheter 282, which may reduce profile. Additionally, the length of the catheter distal of the balloon need not account for the length of the distal electrode, which may enhance flexibility. Furthermore, the guidewire must be exchanged for electrode 270 prior to treatment, which reduces a risk of inadvertent electrical shock. In one variation, electrode 270 optionally may be used as the guidewire over which catheter 282 is advanced into position prior to delivery of the PEF, thereby obviating a need for exchange of the guidewire for the electrode. Alternatively, a standard metallic guidewire may be used as the electrode 270 simply by connecting the standard guidewire to the pulsed electric field generator. The distal electrode 270 may be extended any desired distance beyond the distal end of catheter 282. This may provide for dynamic alteration of the length of a treatment zone. Furthermore, this might facilitate treatment within distal vasculature of reduced diameter.

With reference to FIGS. 19A and 19B, it might be desirable to perform treatments within one or more vascular branches that extend from a main vessel, for example, to perform treatments within the branches of the renal artery in the vicinity of the renal hilum. Furthermore, it might be desirable to perform treatments within abnormal or less common branchings of the renal vasculature, which are observed in a minority of patients. As seen in FIG. 19A, distal electrode 270 may be placed in such a branch of renal artery RA, while catheter 282 is positioned within the main branch of the artery. As seen in FIG. 19B, multiple distal electrodes 270 might be provided and placed in various common or uncommon branches of the renal artery, while the catheter remains in the main arterial branch.

Referring to FIG. 20, yet another variation of an intravascular PEF catheter is described. Apparatus 290 comprises catheter 292 having a plurality of shaft electrodes 294 disposed in line with centering element 296. Centering element 296 illustratively comprises an expandable basket, such as previously described expandable basket 254 of FIG. 8. However, it should be understood that the centering element alternatively may comprise a balloon or any other centering element. Electrodes 294 may be utilized in a bipolar or a monopolar fashion.

Referring now to FIG. 21, another variation of the invention is described comprising electrodes configured for dynamic radial repositioning of one or more of the electrodes relative to a vessel wall, thereby facilitating focusing of a pulsed electric field delivered by the electrodes. Apparatus 300 comprises catheter 302 having electrodes 304 disposed in line with nested expandable elements. The nested expandable elements comprise an inner expandable element 306 and an outer expandable centering element 308. Electrodes 304 are disposed along the inner expandable element, while the outer expandable centering element is configured to center and stabilize catheter 302 within the vessel. Inner element 306 may be expanded to varying degrees, as desired by a medical practitioner, to dynamically alter the radial positions of electrodes 304. This dynamic radial repositioning may be utilized to focus energy delivered by electrodes 304 such that it is delivered to target tissue.

Nested elements 306 and 308 may comprise a balloon-in-balloon arrangement, a basket-in-basket arrangement, some combination of a balloon and a basket, or any other expandable nested structure. In FIG. 21, inner expandable element 306 illustratively comprises an expandable basket, while outer expandable centering element 308 illustratively comprises an expandable balloon. Electrodes 302 are positioned along the surface of inner balloon 306.

Any of the variations of the present invention described herein optionally may be configured for infusion of agents into the treatment area before, during or after energy application, for example, to enhance or modify the neurodestructive or neuromodulatory effect of the energy, to protect or temporarily displace non-target cells, and/or to facilitate visualization. Additional applications for infused agents will be apparent. If desired, uptake of infused agents by cells may be enhanced via initiation of reversible electroporation in the cells in the presence of the infused agents. Infusion may be especially desirable when a balloon centering element is utilized. The infusate may comprise, for example, saline or heparinized saline, protective agents, such as Poloxamer-188, or anti-proliferative agents. Variations of the present invention additionally or alternatively may be configured for aspiration. For example, infusion ports or outlets may be provided on a catheter shaft adjacent a centering device, the centering device may be porous (for instance, a "weeping" balloon), or basket struts may be made of hollow hypotubes and slotted or perforated to allow infusion or aspiration.

With reference to FIG. 22, a variation of the present invention comprising an infusion/aspiration PEF catheter is described. Apparatus 310 comprises catheter 312 having proximal and distal inflatable balloons 314a and 314b, respectively. Proximal shaft electrode 316a is disposed between the balloons along the shaft of catheter 312, while distal electrode 316b is disposed distal of the balloons along the catheter shaft. One or more infusion or aspiration holes 318 are disposed along the shaft of catheter 312 between the balloons in proximity to proximal electrode 316a.

Apparatus 310 may be used in a variety of ways. In a first method of use, catheter 312 is disposed within the target vessel, such as renal artery RA, at a desired location. One or both balloons 314 are inflated, and a protective agent or other infusate is infused through hole(s) 318 between the balloons in proximity to electrode 316a. A PEF suitable for initiation of reversible electroporation is delivered across electrodes 316 to facilitate uptake of the infusate by non-target cells within the vessel wall. Delivery of the protective agent may be enhanced by first inflating distal balloon 314b, then infusing the protective agent, which displaces blood, then inflating proximal balloon 314a.

Remaining infusate optionally may be aspirated such that it is unavailable during subsequent PEF application when irreversible electroporation of nerve cells is initiated. Aspiration may be achieved by at least partially deflating one balloon during aspiration. Alternatively, aspiration may be achieved with both balloons inflated, for example, by infusing saline in conjunction with the aspiration to flush out the vessel segment between the inflated balloons. Such blood flushing may reduce a risk of clot formation along proximal electrode 316a during PEF application. Furthermore, flushing during energy application may cool the electrode and/or cells of the wall of the artery. Such cooling of the wall cells might protect the cells from irreversible electroporative damage, possibly reducing a need for infusion of a protective agent.

After infusion and optional aspiration, a PEF suitable for initiation of irreversible electroporation in target nerve cells may be delivered across electrodes 316 to denervate or to modulate neural activity. In an alternative method, infusion of a protective agent may be performed during or after initiation of irreversible electroporation in order to protect non-target cells. The protective agent may, for example, plug or fill pores formed in the non-target cells via the irreversible electroporation.

In another alternative method, a solution of chilled (i.e., less than body temperature) heparinized saline may be simultaneously infused and aspirated between the inflated balloons to flush the region between the balloons and decrease the sensitivity of vessel wall cells to electroporation. This is expected to further protect the cells during application of the PEF suitable for initiation of irreversible electroporation. Such flushing optionally may be continuous throughout application of the pulsed electric field. A thermocouple or other temperature sensor optionally may be positioned between the balloons such that a rate of chilled infusate infusion may be adjusted to maintain a desired temperature. The chilled infusate preferably does not cool the target tissue, e.g., the renal nerves. A protective agent, such as Poloxamer-188, optionally may be infused post-treatment as an added safety measure.

Infusion alternatively may be achieved via a weeping balloon catheter. Further still, a cryoballoon catheter having at least one electrode may be utilized. The cryoballoon may be inflated within a vessel segment to locally reduce the temperature of the vessel segment, for example, to protect the segment and/or to induce thermal apoptosis of the vessel wall during delivery of an electric field. The electric field may, for example, comprise a PEF or a thermal, non-pulsed electric field, such as a thermal RF field.

Referring now to FIGS. 23A, 23B and 23C, a variation of a PEF catheter configured for passage of electrode(s) at least partially across the vessel wall is described. For example, the electrode(s) may be positioned within the renal vein and then passed across the wall of the renal vein such that they are disposed in Gerota's or renal fascia and near or at least partially around the renal artery. In this manner, the electrode(s) may be positioned in close proximity to target renal nerve fibers prior to delivery of a pulsed electric field.

As seen in FIG. 23A, apparatus 320 comprises catheter 322 having needle ports 324 and centering element 326, illustratively an inflatable balloon. Catheter 322 also optionally may comprise radiopaque markers 328. Needle ports 324 are configured for passage of needles 330 therethrough, while needles 330 are configured for passage of electrodes 340.

Renal vein RV runs parallel to renal artery RA. An imaging modality, such as intravascular ultrasound, may be used to identify the position of the renal artery relative to the renal vein. For example, intravascular ultrasound elements optionally may be integrated into catheter 322. Catheter 322 may be positioned within renal vein RV using well-known percutaneous techniques, and centering element 326 may be expanded to stabilize the catheter within the vein. Needles 330 then may be passed through catheter 322 and out through needle ports 324 in a manner whereby the needles penetrate the wall of the renal vein and enter into Gerota's or renal fascia F. Radiopaque markers 328 may be visualized with fluoroscopy to properly orient needle ports 324 prior to deployment of needles 330.

Electrodes 340 are deployed through needles 330 to at least partially encircle renal artery RA, as in FIGS. 23A and 23B. Continued advancement of the electrodes may further encircle the artery, as in FIG. 23C. With the electrodes deployed, stimulation and/or PEF electroporation waveforms may be applied to denervate or modulate the renal nerves. Needles 330 optionally may be partially or completely retracted prior to treatment such that electrodes 340 encircle a greater portion of the renal artery. Additionally, a single electrode 340 may be provided and/or actuated in order to provide a monopolar PEF.

Infusate optionally may be infused from needles 330 into fascia F to facilitate placement of electrodes 340 by creating a space for placement of the electrodes. The infusate may comprise, for example, fluids, heated or chilled fluids, air, $CO_2$, saline, contrast agents, gels, conductive fluids or any other space-occupying material—be it gas, solid or liquid. Heparinized saline also may be injected. Saline or hypertonic saline may enhance conductivity between electrodes 340. Additionally or alternatively, drugs and/or drug delivery elements may be infused or placed into the fascia through the needles.

After treatment, electrodes 340 may be retracted within needles 330, and needles 330 may be retracted within catheter 322 via needle ports 324. Needles 330 preferably are small enough that minimal bleeding occurs and hemostasis is achieved fairly quickly. Balloon centering element 326 optionally may remain inflated for some time after retrieval of needles 330 in order to block blood flow and facilitate the clotting process. Alternatively, a balloon catheter may be advanced into the renal vein and inflated after removal of apparatus 320.

Referring to FIGS. 24A and 24B, variations of the invention comprising detectors or other elements for measuring or monitoring treatment efficacy are described. Variations of the invention may be configured to deliver stimulation electric fields, in addition to denervating or modulating PEFs. These stimulation fields may be utilized to properly position the apparatus for treatment and/or to monitor the effectiveness of treatment in modulating neural activity. This may be achieved by monitoring the responses of physiologic parameters known to be affected by stimulation of the renal nerves. Such parameters comprise, for example, renin levels, sodium levels, renal blood flow and blood pressure. Stimulation also may be used to challenge the denervation for monitoring of treatment efficacy: upon denervation of the renal nerves, the known physiologic responses to stimulation should no longer occur in response to such stimulation.

Efferent nerve stimulation waveforms may, for example, comprise frequencies of about 1-10 Hz, while afferent nerve stimulation waveforms may, for example, comprise frequencies of up to about 50 Hz, Waveform amplitudes may, for example, range up to about 50V, while pulse durations may, for example, range up to about 20 milliseconds. When the nerve stimulation waveforms are delivered intravascularly, as in several embodiments of the present invention, field parameters such as frequency, amplitude and pulse duration may be modulated to facilitate passage of the waveforms through the wall of the vessel for delivery to target nerves. Furthermore, although exemplary parameters for stimulation waveforms have been described, it should be understood that any alternative parameters may be utilized as desired.

The electrodes used to deliver PEFs in any of the previously described variations of the present invention also may be used to deliver stimulation waveforms to the renal vasculature. Alternatively, the variations may comprise independent electrodes configured for stimulation. As another alternative, a separate stimulation apparatus may be provided.

One way to use stimulation to identify renal nerves is to stimulate the nerves such that renal blood flow is affected—or would be affected if the renal nerves had not been denervated or modulated. Stimulation acts to reduce renal blood flow, and this response may be attenuated or abolished with denervation. Thus, stimulation prior to neural modulation would be expected to reduce blood flow, while stimulation after neural modulation would not be expected to reduce blood flow to the same degree when utilizing similar stimulation parameters and location(s) as prior to neural modulation. This phenomenon may be utilized to quantify an extent of renal neuromodulation. Variations of the present invention may comprise elements for monitoring renal blood flow or for monitoring any of the other physiological parameters known to be affected by renal stimulation.

In FIG. 24A, a variation of apparatus 280 of FIG. 16 is described having an element for monitoring of renal blood flow. Guidewire 350 having Doppler ultrasound sensor 352 has been advanced through the lumen of catheter 282 for monitoring blood flow within renal artery RA. Doppler ultrasound sensor 352 is configured to measure the velocity of flow through the artery. A flow rate then may be calculated according to the formula:

$$Q=VA \qquad (1)$$

where Q equals flow rate, V equals flow velocity and A equals cross-sectional area. A baseline of renal blood flow may be determined via measurements from sensor 352 prior to delivery of a stimulation waveform, then stimulation may be delivered between electrodes 286a and 286b, preferably with balloon 284 deflated. Alteration of renal blood flow from the baseline, or lack thereof, may be monitored with sensor 352 to identify optimal locations for neuromodulation and/or denervation of the renal nerves.

FIG. 24B illustrates a variation of the apparatus of FIG. 24A, wherein Doppler ultrasound sensor 352 is coupled to the shaft of catheter 282. Sensor 352 illustratively is disposed proximal of balloon 284, but it should be understood that the sensor alternatively may be disposed distal of the balloon.

In addition or as an alternative to intravascular monitoring of renal blood flow via Doppler ultrasound, such monitoring optionally may be performed from external to the patient whereby renal blood flow is visualized through the skin (e.g., using an ultrasound transducer). In another variation, one or more intravascular pressure transducers may be used to sense local changes in pressure that may be indicative of renal blood flow. As yet another alternative, blood velocity may be determined, for example, via thermodilution by measuring the time lag for an intravascular temperature input to travel between points of known separation distance.

For example, a thermocouple may be incorporated into, or provided in proximity to, each electrode 286a and 286b, and chilled (i.e., lower than body temperature) fluid or saline may be infused proximally of the thermocouple(s). A time lag for the temperature decrease to register between the thermocouple(s) may be used to quantify flow characteristic(s). A baseline estimate of the flow characteristic(s) of interest may be determined prior to stimulation of the renal nerves and may be compared with a second estimate of the characteristic(s) determined after stimulation.

Commercially available devices optionally may be utilized to monitor treatment. Such devices include, for example, the SmartWire™, FloWire™ and WaveWire™ devices available from Volcano™ Therapeutics Inc., of Rancho Cordova, Calif., as well as the PressureWire® device available from RADI Medical Systems AB of Uppsala, Sweden. Additional commercially available devices will be apparent. An extent of electroporation additionally or alternatively may be monitored directly using Electrical Impedance Tomography ("EIT") or other electrical impedance measurements, such as an electrical impedance index.

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired. It is intended in the appended claims to cover all such changes and modifications that fall within the true spirit and scope of the invention.

We claim:

1. An apparatus for renal neuromodulation, the apparatus comprising:
   an electric field generator configured to deliver non-pulsed thermal RF energy to renal nerves that modulate renal neural activity of a human patient;
   a catheter having a distal portion configured for percutaneous placement within a renal blood vessel of the patient;
   an expandable balloon at the distal portion of the catheter, wherein the expandable balloon is selectively transformable between a low-profile, delivery configuration and a deployed configuration sized to fit within the renal blood vessel, and wherein the expandable balloon comprises a weeping balloon for infusion of a selected agent therefrom; and
   a helical conductor electrically connectable to the electric field generator and arranged about the expandable balloon such that, when the balloon is in the deployed configuration, the helical conductor is configured to deliver the thermal RF energy through an inner wall of the renal blood vessel to neural fibers that innervate a kidney of the patient to reduce renal sympathetic nerve activity.

2. The apparatus of claim 1 wherein, in the deployed configuration, the balloon is sized to occlude the renal blood vessel.

3. The apparatus of claim 1 wherein the energy from the helical conductor is sufficient to cause at least partial renal denervation.

4. The apparatus of claim 1 wherein the energy from the helical conductor is sufficient to cause at least partial ablation of at least one neural fiber.

5. The apparatus of claim 1 wherein the helical conductor is sized and shaped to physically contact the inner wall of the renal blood vessel when the balloon is in the deployed configuration.

6. The apparatus of claim 1 wherein, when the balloon is in the deployed configuration, the helical conductor is configured to deliver the energy through the inner wall of the renal blood vessel in a helical pattern.

7. The apparatus of claim 1, further comprising one or more sensors at the distal portion of the catheter for monitoring and/or controlling effects of the energy delivery.

8. The apparatus of claim 7 wherein at least one of the sensors comprises a thermocouple for monitoring temperature.

9. The apparatus of claim 1 wherein the catheter is configured for placement in the renal blood vessel over a guidewire.

10. The apparatus of claim 1 wherein the balloon is collapsed for delivery to the renal blood vessel within a sheath, and further wherein the balloon is configured to expand into contact with the wall of the renal blood vessel after exiting from the sheath.

11. The apparatus of claim 1 wherein the selected agent comprises saline.

12. The apparatus of claim 1 wherein the balloon, when in the low-profile delivery configuration, is sized to fit within a sheath, and further wherein the balloon is configured to expand into contact with the wall of the renal blood vessel after exiting from the sheath.

13. A renal neuromodulation system, comprising:
   an electric field generator configured to deliver a non-pulsed thermal RF field to renal nerves that modulate renal neural activity of a human patient; and
   a catheter comprising (a) a shaft having a lumen therethrough, (b) an expandable distal balloon, wherein the balloon comprises a weeping balloon for infusion of a selected agent therefrom, and (c) at least one electrode, the catheter being transformable between—
     a reduced delivery configuration for percutaneous intravascular placement within renal vasculature of the patient, and
     an expanded treatment configuration for delivering the thermal RF field to one or more of the renal nerves,
   wherein the at least one electrode is electrically connectable to the electric field generator and comprises a helical configuration arranged about and expandable by the balloon for delivering the thermal RF field to one or more renal nerves to thermally induce modulation of a function of the one or more renal nerves when the catheter is at least partially located within the renal vasculature.

14. The system of claim 13 wherein the at least one electrode is affixed to an outside surface of or embedded within a wall of the balloon.

15. The apparatus of claim 13 wherein, in the deployed configuration, the balloon is sized and shaped to physically contact a wall of the renal vasculature and is configured to act as an insulator to increase impedance within an interior of the renal vasculature and thereby direct an electric field along a desired electric flow path through the wall of the renal vasculature when the balloon is expanded into contact therewith.

16. The system of claim 13 wherein the catheter is configured for infusion of one or more agents into the renal vasculature before, during, or after delivery of the electric field to the one or more renal nerves.

17. The system of claim 16 wherein the one or more agents are chosen from the group consisting of saline, heparinized saline, poloxamer-188 or other protective agents, or antiproliferative agents.

18. The system of claim 13 wherein the at least one electrode comprises a first dynamically controllable electrode, and wherein the catheter further comprises at least one additional dynamically controllable electrode electrically connectable to the electric field generator.

19. The system of claim 13 wherein the at least one electrode is configured for monopolar use in conjunction with a separate external patient ground.

20. The system of claim 13 wherein the lumen is a guidewire lumen.

21. A method for performing renal neuromodulation, the method comprising:
   intravascularly positioning a catheter within a renal blood vessel and at least partially adjacent to a renal nerve of a human patient, wherein the catheter comprises a distal balloon with a helical conductor arranged thereon;
   expanding the distal balloon of the catheter;
   delivering an energy field via the helical conductor to modulate neural function of the renal nerve; and
   infusing one or more agents into the renal blood vessel before, during or after delivering the energy field, wherein the balloon comprises a weeping balloon and the one or more agents are infused therefrom.

22. The method of claim 21 wherein delivering an energy field via the helical conductor comprises delivering a non-pulsed thermal RF field.

23. The method of claim 21 wherein delivering an energy field via the helical conductor comprises delivering a bipolar electric field between at least one pair of electrodes arranged about the balloon.

24. The method of claim 21, further comprising monitoring at least one physiological parameter of the patient with a Doppler ultrasound sensor, a temperature sensor, a pressure sensor, an impedance detector, or a combination thereof.

25. The method of claim 21 wherein intravascularly positioning the catheter comprises delivering the catheter over a guidewire.

26. The method of claim 21 wherein infusing one or more agents into the renal blood vessel comprises infusing saline through one or more pores in the balloon.

27. The method of claim 21 wherein expanding the distal balloon comprises placing the helical conductor arranged on the balloon into physical contact with an inner wall of a renal blood vessel of the patient.

28. The method of claim 21 wherein intravascularly positioning the catheter comprises delivering the catheter via a sheath.

* * * * *